(12) United States Patent
Morton et al.

(10) Patent No.: US 9,968,748 B2
(45) Date of Patent: May 15, 2018

(54) INDICATING DEVICE WITH WARNING DOSAGE INDICATOR

(71) Applicant: TRUDELL MEDICAL INTERNATIONAL, London (CA)

(72) Inventors: Robert Morton, London (CA); Winston Z. Lu, Kitchener (CA)

(73) Assignee: TRUDELL MEDICAL INTERNATIONAL, London, Ontario (CA)

( * ) Notice: Subject to any disclaimer, the term of this patent is extended or adjusted under 35 U.S.C. 154(b) by 378 days.

(21) Appl. No.: 14/054,179

(22) Filed: Oct. 15, 2013

(65) Prior Publication Data

US 2014/0165998 A1 Jun. 19, 2014

Related U.S. Application Data

(63) Continuation of application No. 12/579,129, filed on Oct. 14, 2009, now Pat. No. 8,578,934, which is a
(Continued)

(51) Int. Cl.
 *A61M 15/00* (2006.01)
(52) U.S. Cl.
 CPC ...... *A61M 15/0076* (2014.02); *A61M 15/009* (2013.01); *A61M 15/0065* (2013.01); *A61M 15/0073* (2014.02); *A61M 15/0075* (2014.02)
(58) Field of Classification Search
 CPC .......... A61M 15/0065; A61M 15/0068; A61M 15/0071; A61M 15/0073; A61M 15/0075; A61M 15/0076
(Continued)

(56) References Cited

U.S. PATENT DOCUMENTS

| 165,054 A | 6/1875 | Baldwin |
| 498,851 A | 6/1893 | Jones |

(Continued)

FOREIGN PATENT DOCUMENTS

| AU | 598250 B2 | 6/1990 |
| CA | 0 535 518 A | 1/1957 |

(Continued)

OTHER PUBLICATIONS

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

(Continued)

*Primary Examiner* — Peter S Vasat
*Assistant Examiner* — Margaret Luarca
(74) *Attorney, Agent, or Firm* — Brinks Gilson & Lione

(57) ABSTRACT

An indicating device for indicating the number of dosages of a substance that have been dispensed from or remain in a container includes a first housing member having laterally spaced apart first and second guide members and a second housing member. The first and second housing members are moveable relative to each other along a longitudinal axis. The second housing member includes laterally spaced apart first and second guides shaped to receive the first and second guide members respectively, and wherein the first and second guides are not shaped to receive the second and first guide members respectively. A biasing member biases the second member relative to the first member along the longitudinal axis. An indicating member is disposed between the first and second housing members.

28 Claims, 45 Drawing Sheets

Related U.S. Application Data continuation of application No. 10/968,815, filed on Oct. 18, 2004, now Pat. No. 7,621,273.

(60) Provisional application No. 60/515,316, filed on Oct. 28, 2003.

(58) Field of Classification Search
USPC .................................... 128/200.14, 200.17
See application file for complete search history.

(56) References Cited

U.S. PATENT DOCUMENTS

| | | |
|---|---|---|
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Scheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,191,867 A | 6/1965 | Helms |
| 3,189,232 A | 9/1965 | Joffe |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 5/1970 | Hayes et al. |
| 3,511,409 A | 12/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newell-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |

(56) References Cited

U.S. PATENT DOCUMENTS

| | | |
|---|---|---|
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Ambrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | de la Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs et al. |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,988,496 A | 11/1999 | Bruna |
| 6,000,159 A | 12/1999 | Hornung |
| 6,012,450 A | 1/2000 | Rubsamen |
| 6,029,659 A | 2/2000 | O'Connor |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,186,364 B1 | 2/2001 | Dobbs |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | de la Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,907,876 B1 | 6/2005 | Clark et al. |
| 7,100,530 B2 | 9/2006 | Lu |
| 7,137,391 B2 | 11/2006 | Bruna |
| 7,143,764 B1 | 12/2006 | Dagsland et al. |
| 7,156,258 B2 | 1/2007 | Eckert |
| 7,681,572 B2* | 3/2010 | Fishman ............ A61M 16/0051 128/200.14 |
| 2002/0000225 A1 | 1/2002 | Schuler et al. |
| 2002/0047021 A1* | 4/2002 | Blacker ............... A61M 15/009 222/23 |
| 2002/0139812 A1 | 10/2002 | Scarrott et al. |
| 2002/0153005 A1 | 10/2002 | Scarrott et al. |
| 2003/0183225 A1 | 10/2003 | Knudsen |
| 2003/0200964 A1 | 10/2003 | Blakley et al. |
| 2003/0209239 A1 | 11/2003 | Rand et al. |
| 2004/0065326 A1 | 4/2004 | Macmichael et al. |
| 2004/0069301 A1 | 4/2004 | Bacon |
| 2004/0094147 A1 | 5/2004 | Schyra et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0221840 A1 | 11/2004 | Stockman-Lamb |
| 2004/0255935 A1 | 12/2004 | Bruna |

(56) References Cited

U.S. PATENT DOCUMENTS

| | | |
|---|---|---|
| 2004/0255936 A1 | 12/2004 | Urbanus |
| 2005/0011515 A1 | 2/2005 | Lee et al. |
| 2005/0056276 A1 | 3/2005 | Schuler et al. |
| 2005/0268905 A1 | 12/2005 | Rasmussen et al. |
| 2005/0284471 A1 | 12/2005 | Bruna |
| 2006/0096594 A1 | 5/2006 | Bonney et al. |
| 2006/0254581 A1 | 11/2006 | Genova et al. |

FOREIGN PATENT DOCUMENTS

| | | |
|---|---|---|
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| DE | 6 603 758 U | 7/1969 |
| DE | DT 27 02 539 A1 | 1/1977 |
| DE | 33 36 486 A1 | 4/1984 |
| DE | G 8 590 143.1 U1 | 10/1985 |
| DE | G 8 602 238.5 U1 | 5/1986 |
| EP | 0 028 929 A2 | 5/1981 |
| EP | 0 098 939 A2 | 1/1984 |
| EP | 0 114 617 A2 | 8/1984 |
| EP | 0 063 599 B1 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 0 949 584 A3 | 9/2001 |
| EP | 1 254 678 A2 | 11/2002 |
| EP | 1 369 139 A1 | 12/2003 |
| EP | 1 220 802 B1 | 2/2004 |
| FR | 2 743 055 A1 | 7/1997 |
| GB | 998 148 A | 7/1965 |
| GB | 1 058 636 A | 2/1967 |
| GB | 1 290 484 A | 9/1972 |
| GB | 1 317 315 A | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 414 187 A | 11/2005 |
| JP | 06-026891 U | 4/1994 |
| WO | WO 86/02275 A1 | 4/1986 |
| WO | WO 87/04354 A1 | 8/1987 |
| WO | WO 90/10470 A1 | 9/1990 |
| WO | WO 91/06334 A1 | 5/1991 |
| WO | WO 92/07600 A1 | 5/1992 |
| WO | WO 92/09324 A1 | 6/1992 |
| WO | WO 92/15353 A2 | 9/1992 |
| WO | WO 92/17231 A1 | 10/1992 |
| WO | WO 93/24167 A1 | 12/1993 |
| WO | WO 94/11272 A1 | 5/1994 |
| WO | WO 94/14492 A2 | 7/1994 |
| WO | WO 95/34874 A1 | 12/1995 |
| WO | WO 96/16686 A1 | 6/1996 |
| WO | WO 96/16687 A1 | 6/1996 |
| WO | WO 96/39337 A1 | 12/1996 |
| WO | WO 98/01822 A1 | 1/1998 |
| WO | WO 98/56444 A1 | 12/1998 |
| WO | WO 98/56445 A1 | 12/1998 |
| WO | WO 99/36115 A2 | 7/1999 |
| WO | WO 99/57019 A2 | 11/1999 |
| WO | WO 00/09187 A1 | 2/2000 |
| WO | WO 00/59806 A1 | 10/2000 |
| WO | WO 01/28887 A1 | 4/2001 |
| WO | WO 01/29765 A1 | 4/2001 |
| WO | WO 01/37909 A1 | 5/2001 |
| WO | WO 03/101514 A1 | 12/2003 |
| WO | WO 03/103759 A1 | 12/2003 |
| WO | WO 2004/089451 A1 | 10/2004 |
| WO | WO 2006/11080 A1 | 10/2006 |

OTHER PUBLICATIONS

International Search Report in International Application No. PCT/IB03/01032, dated Aug. 19, 2003, 10 pages.

Written Opinion of the International Searching Authority for International Application No. PCT/CA2004/001884, dated Mar. 4, 2005, 6 pages.

Supplemental European Search Report for European Application No. 04789791, dated Jul. 22, 2011, 2 pages.

\* cited by examiner

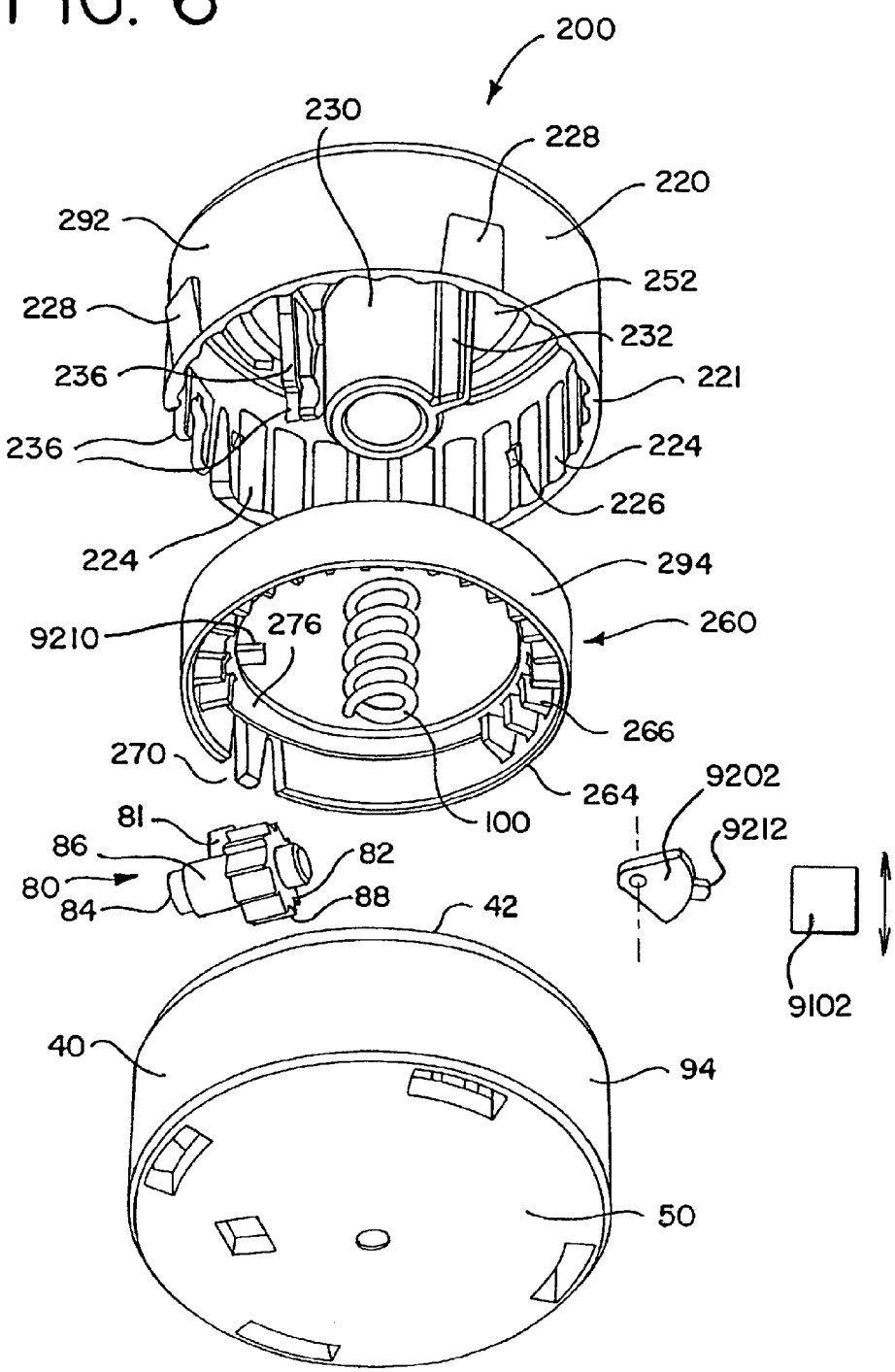

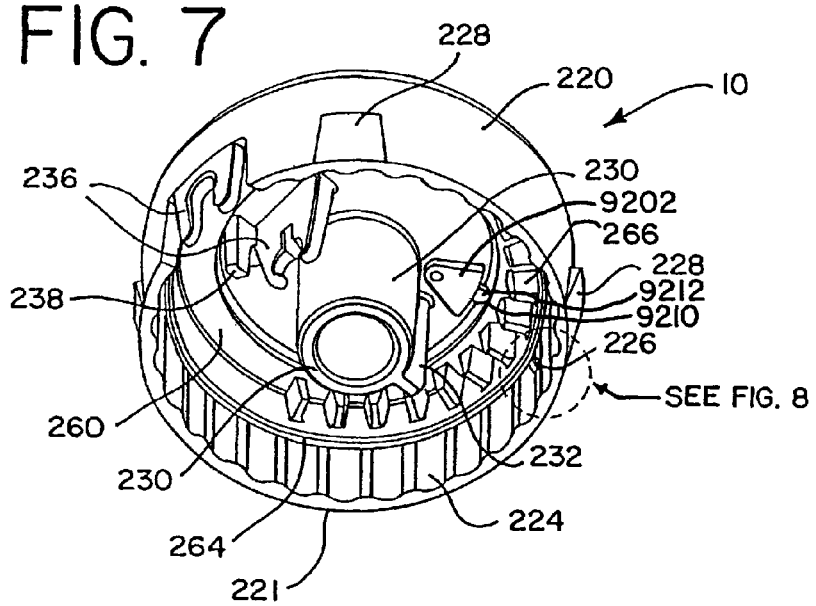
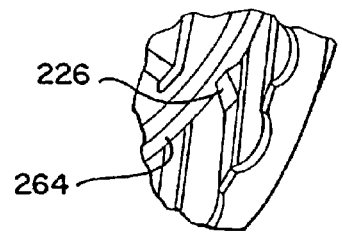
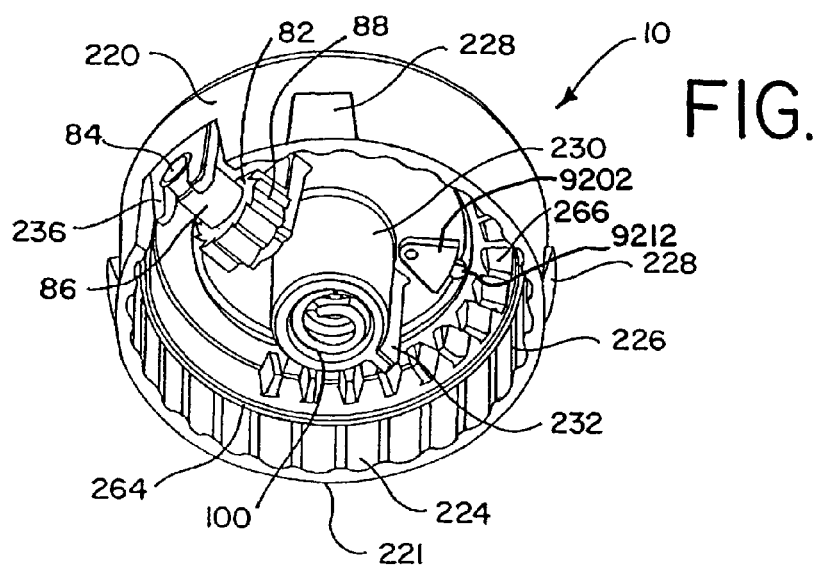

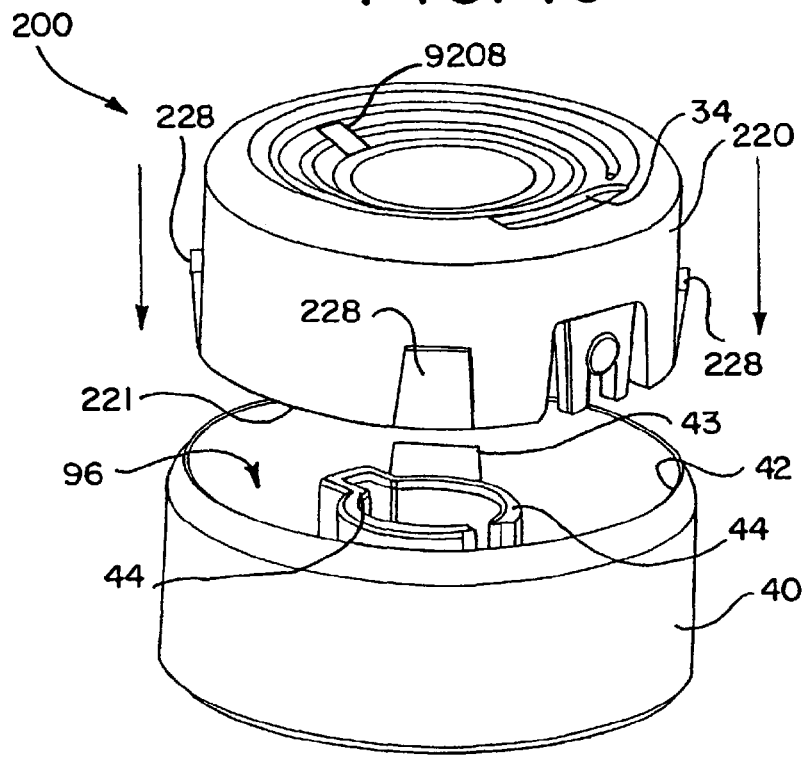
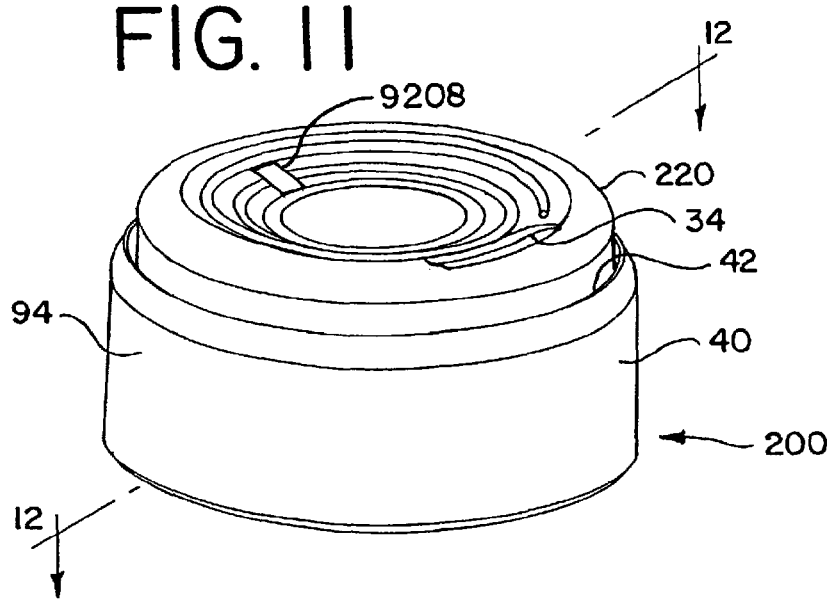

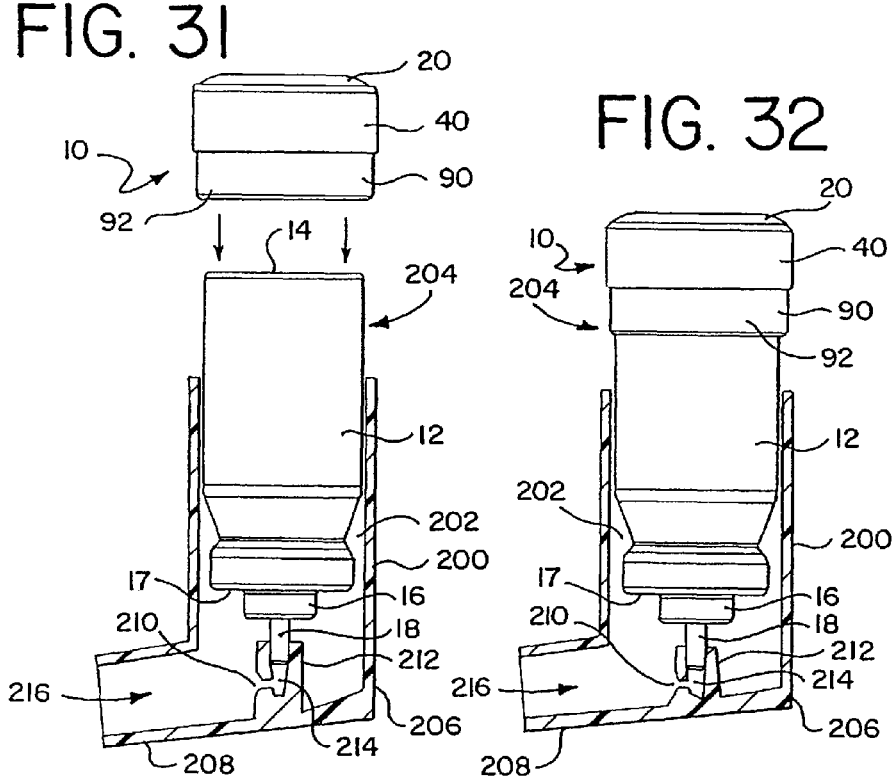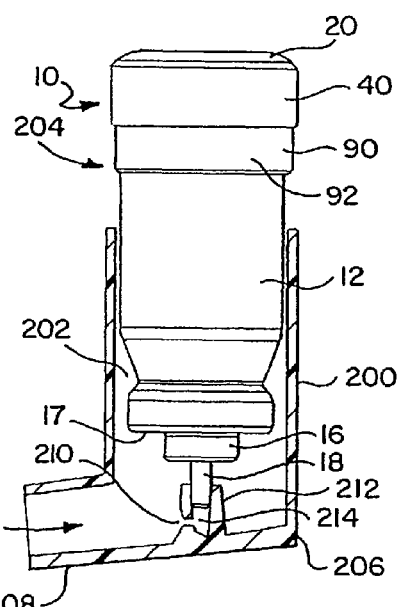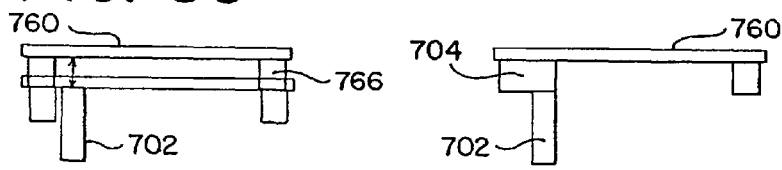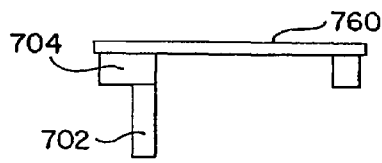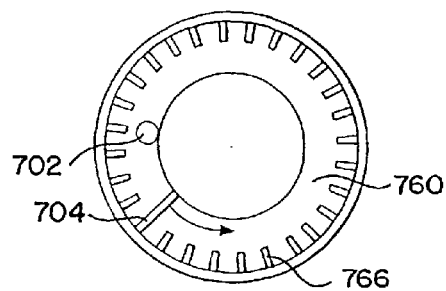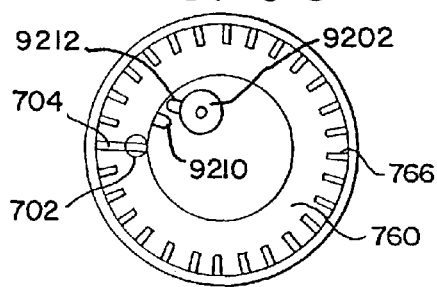

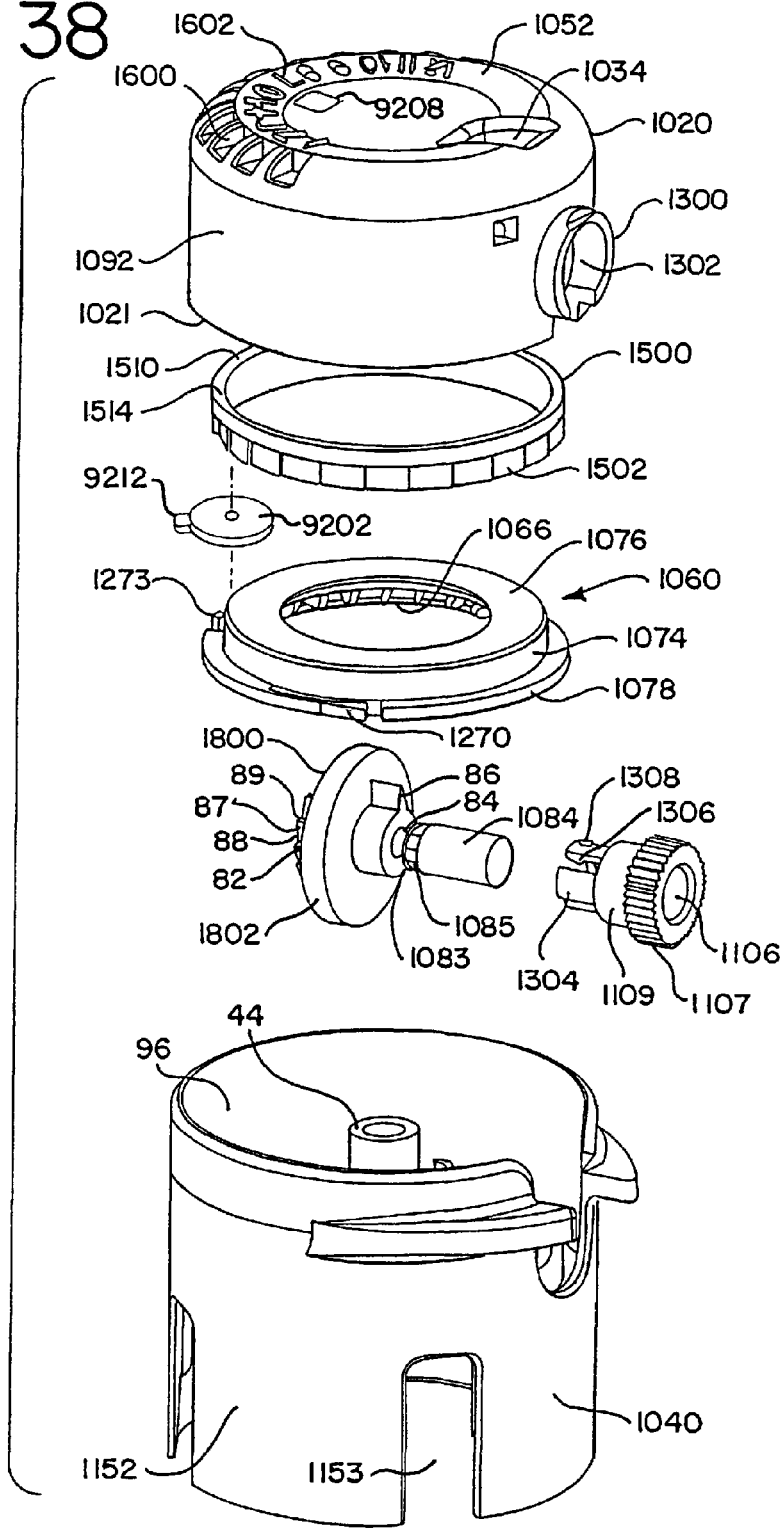

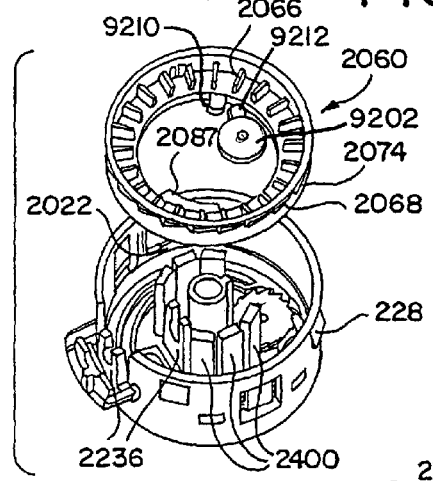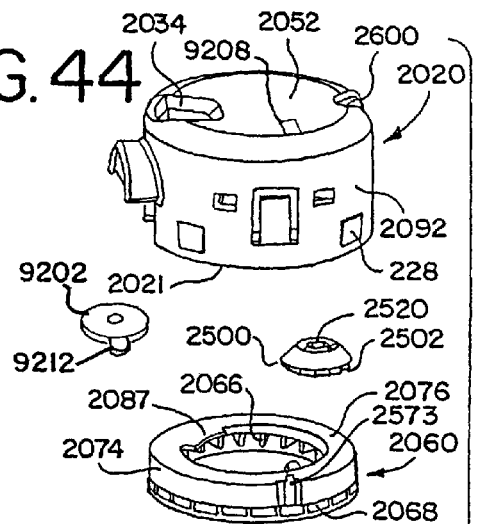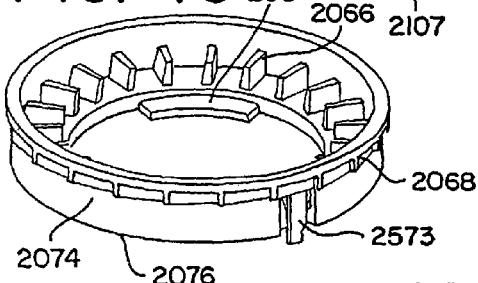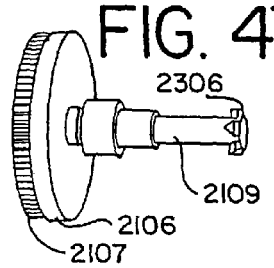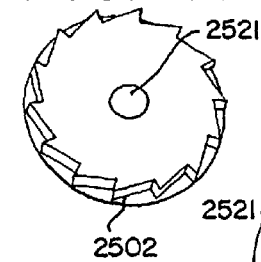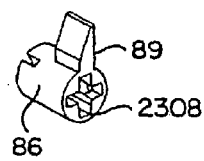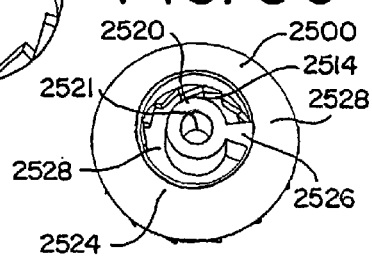

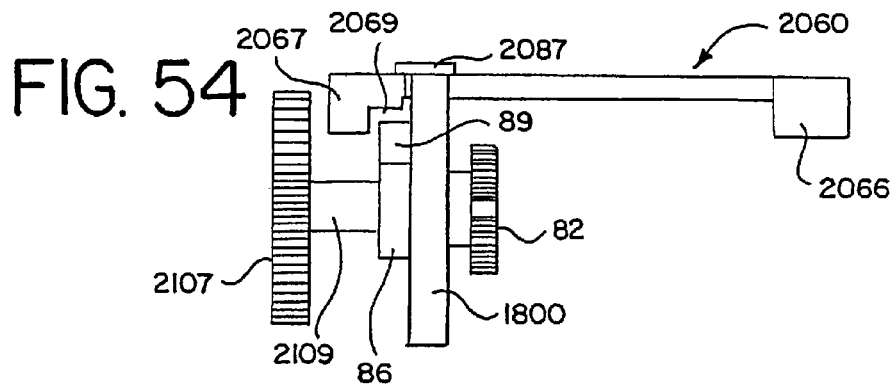
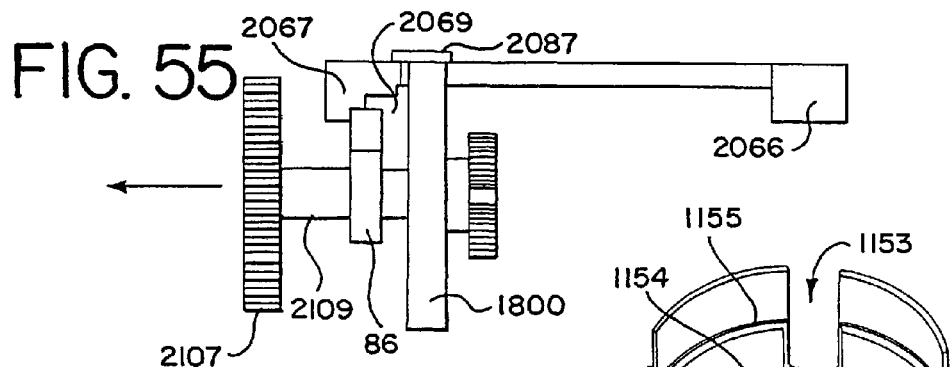
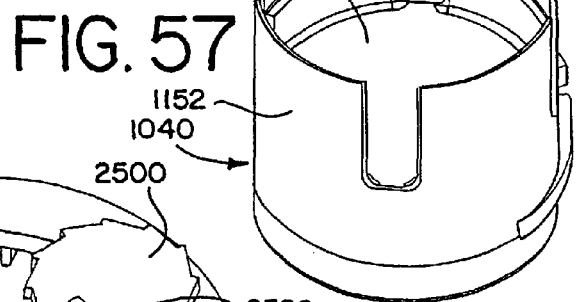
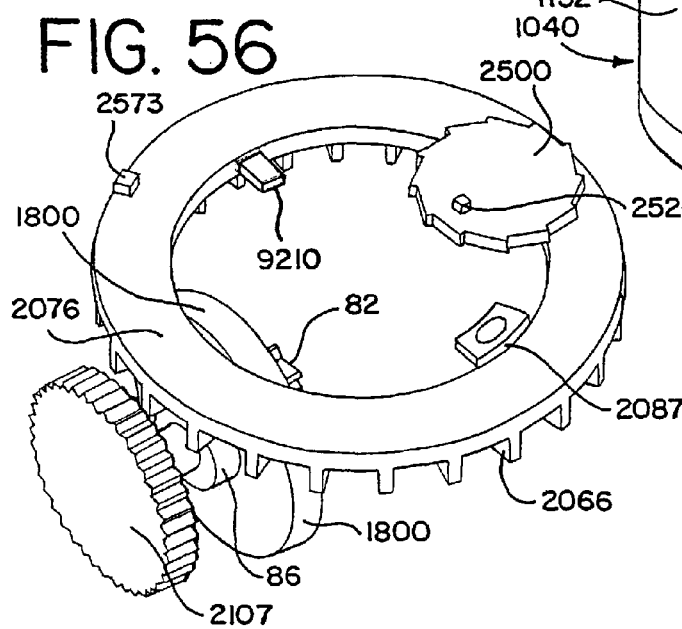

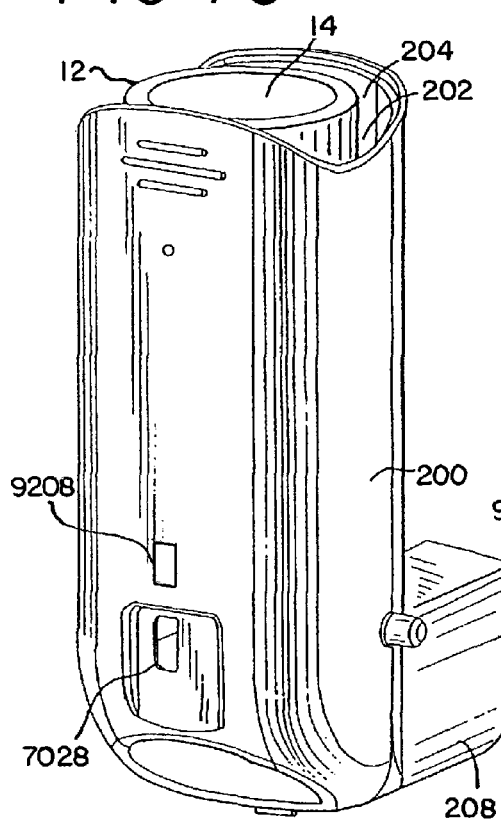
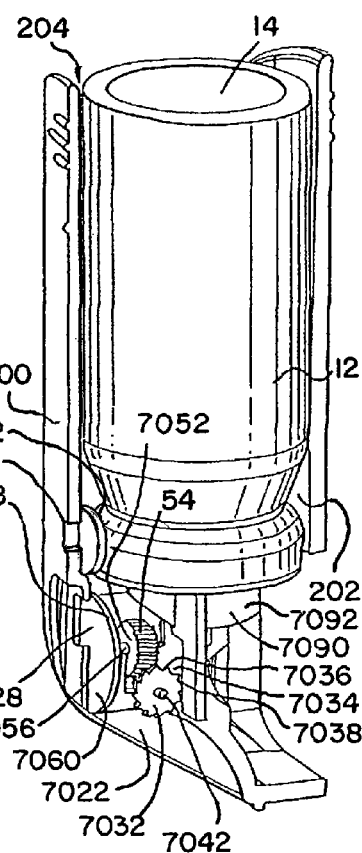
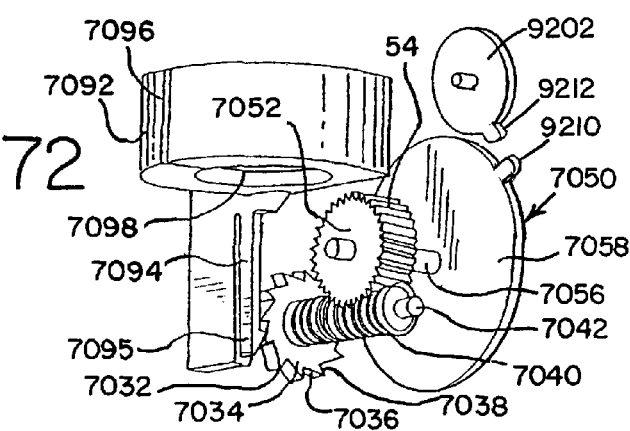

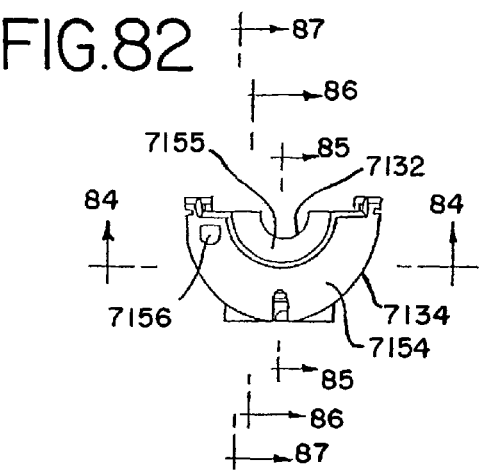
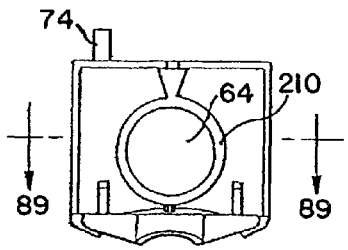
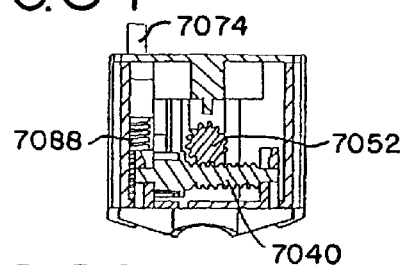
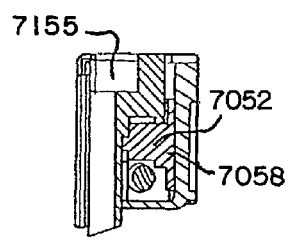
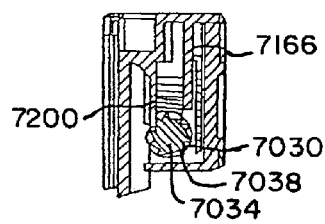
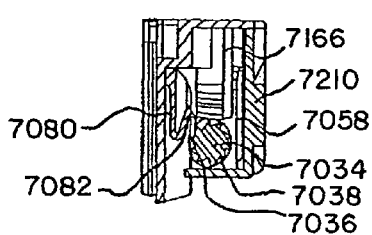
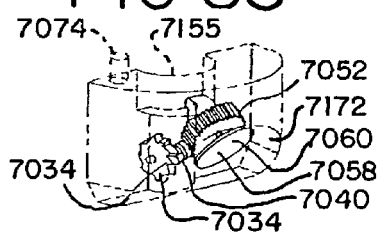
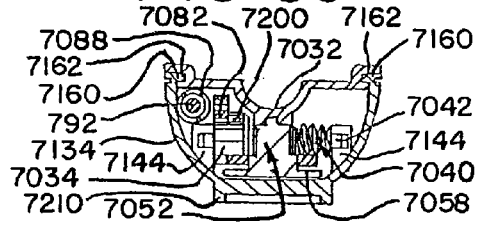

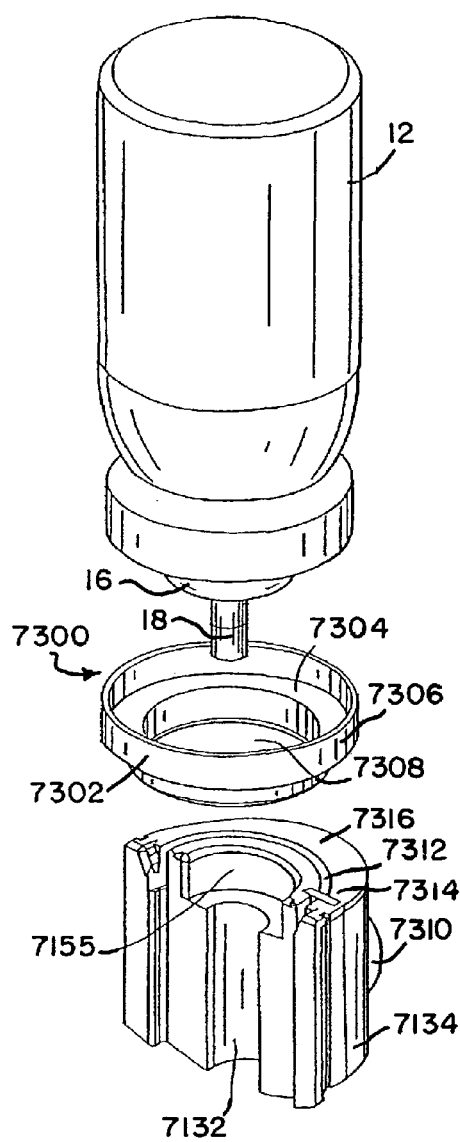
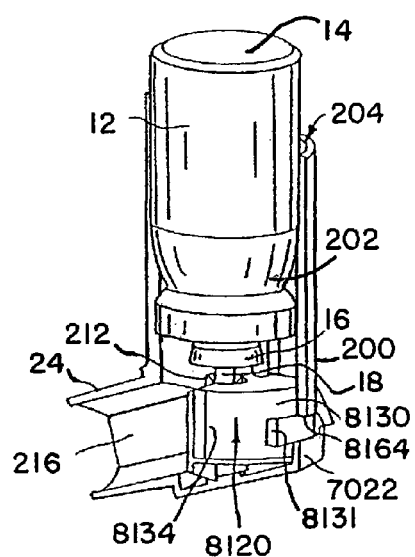
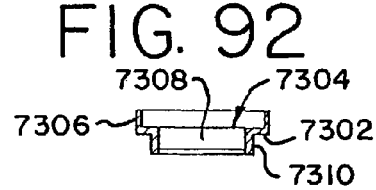
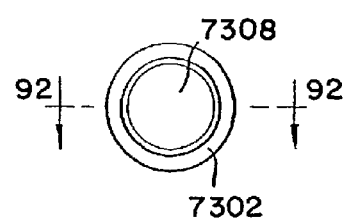

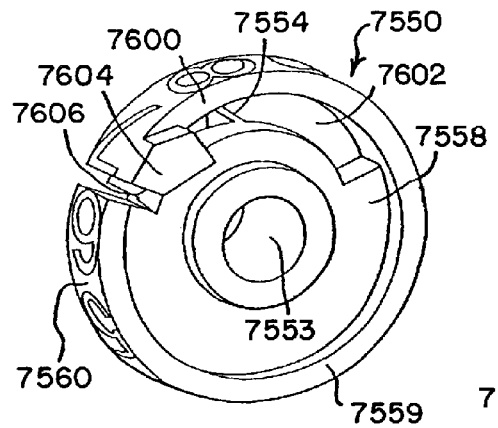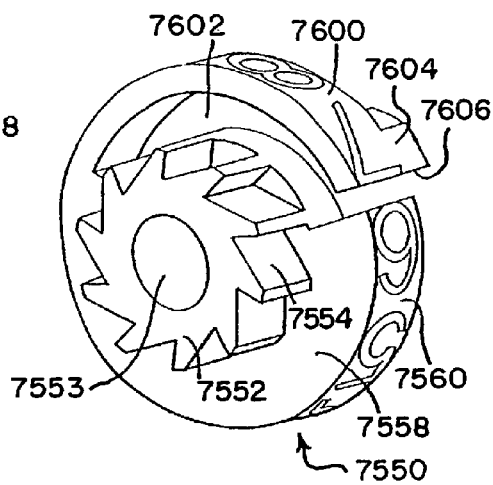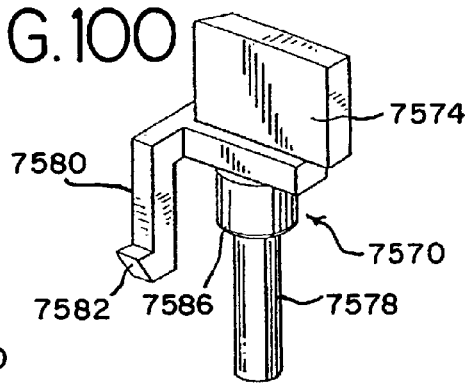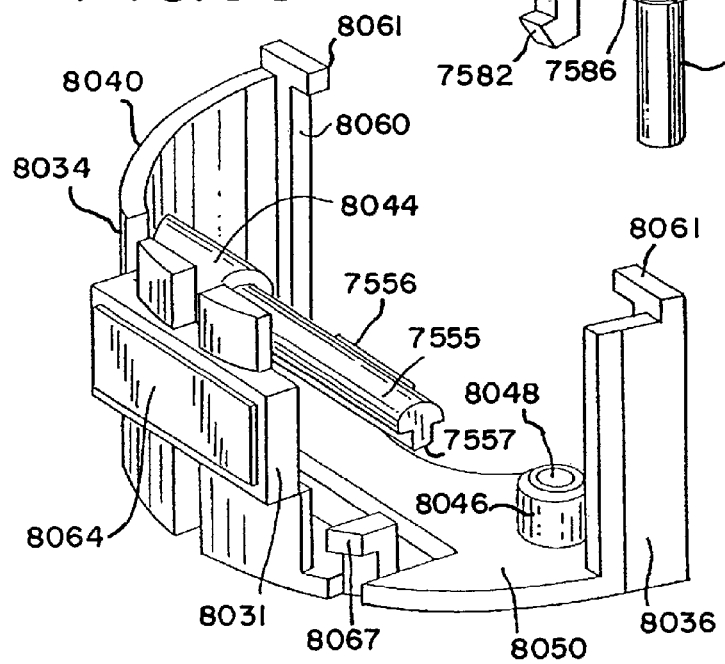

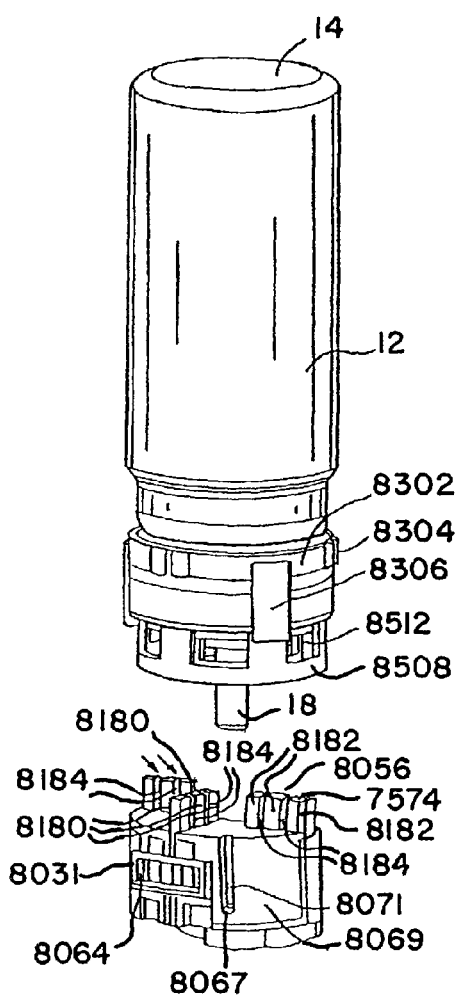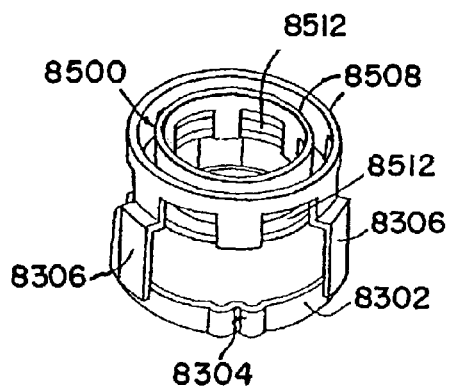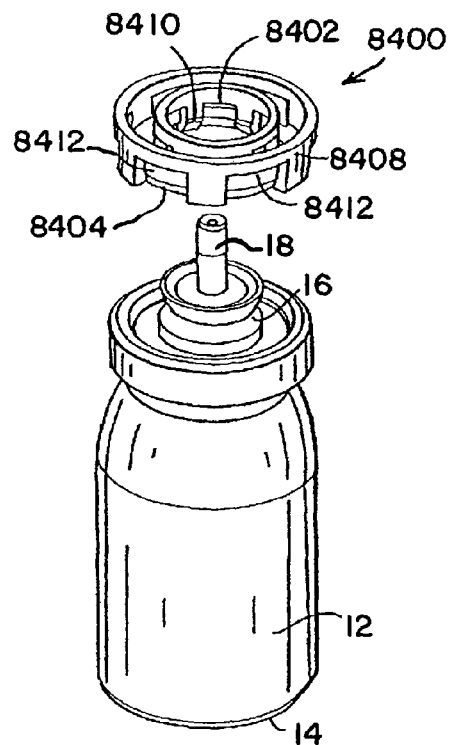

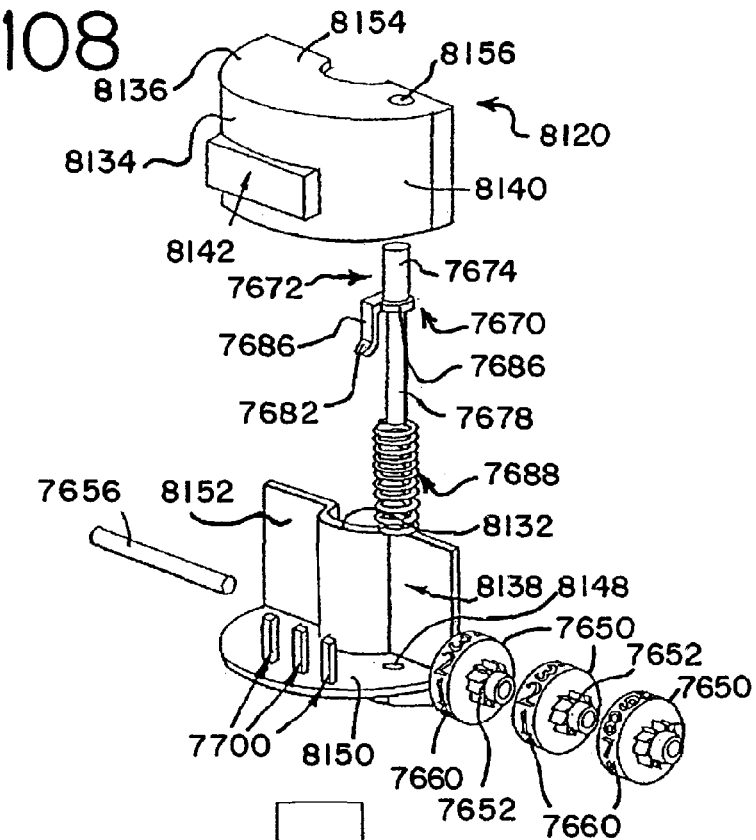
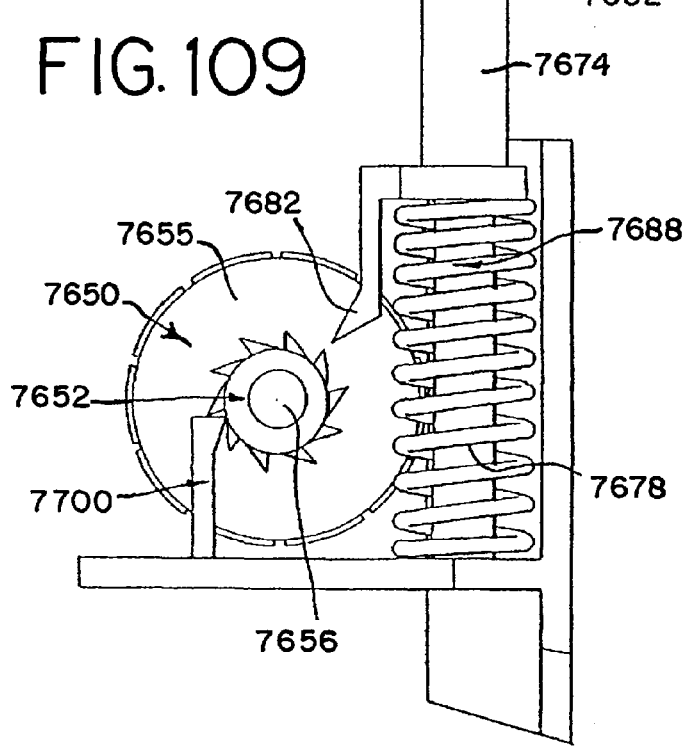

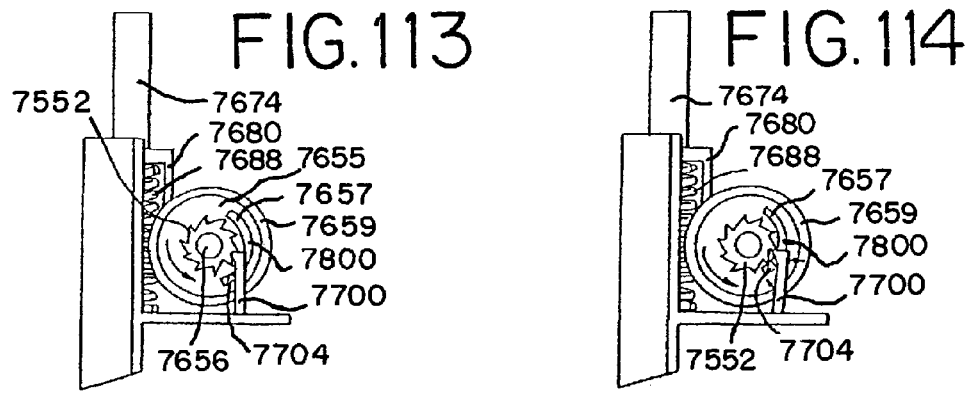
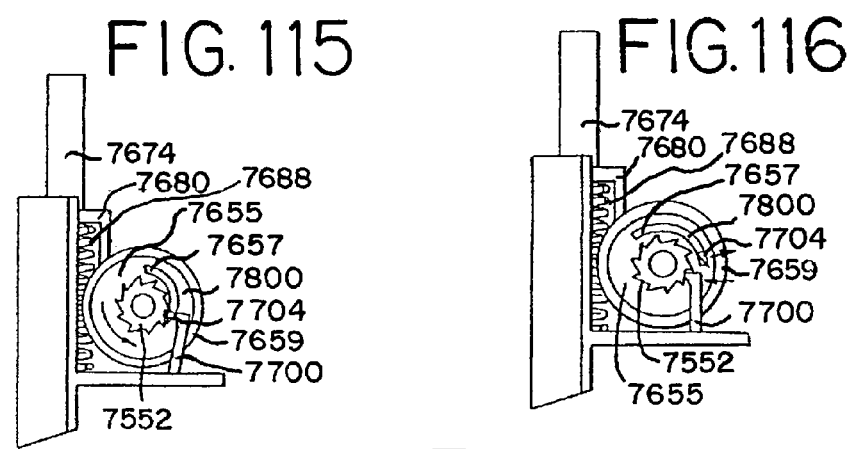
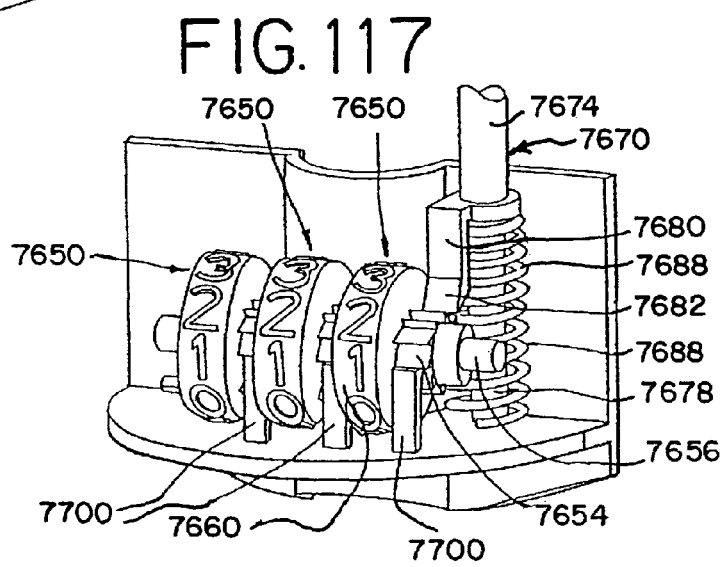

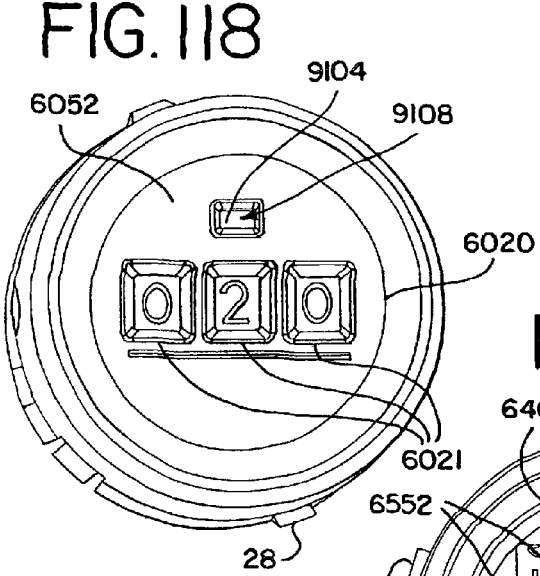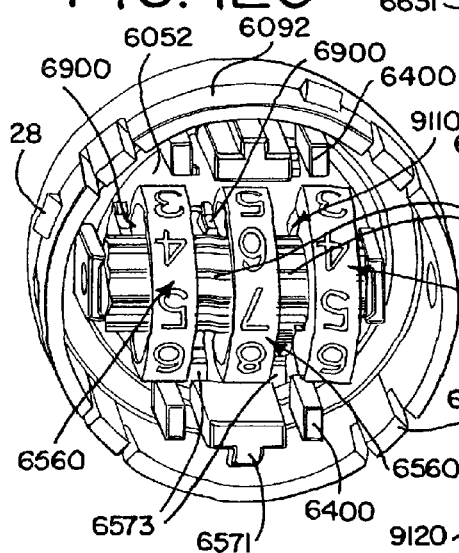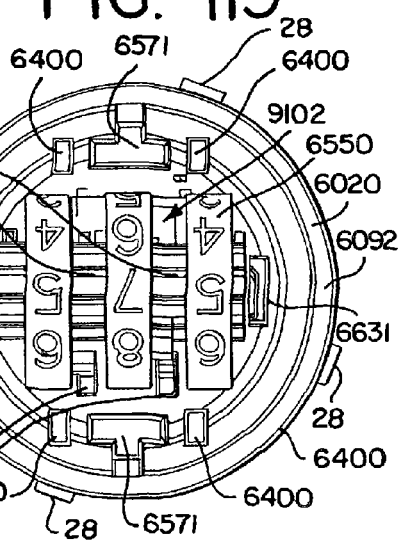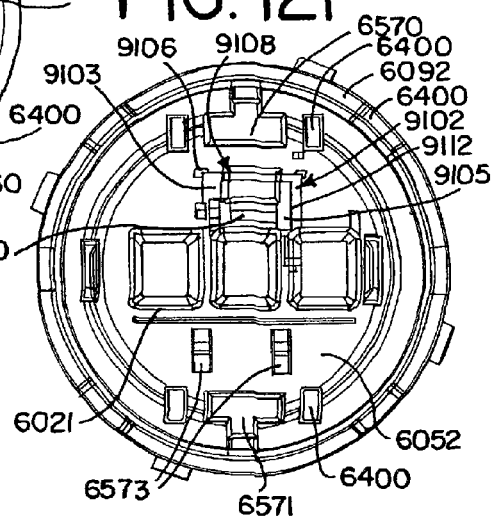

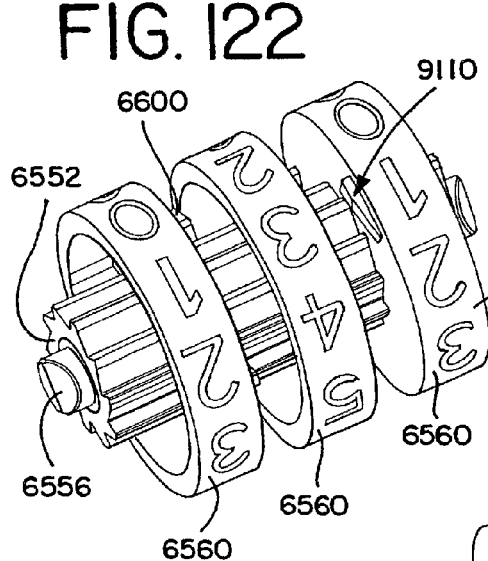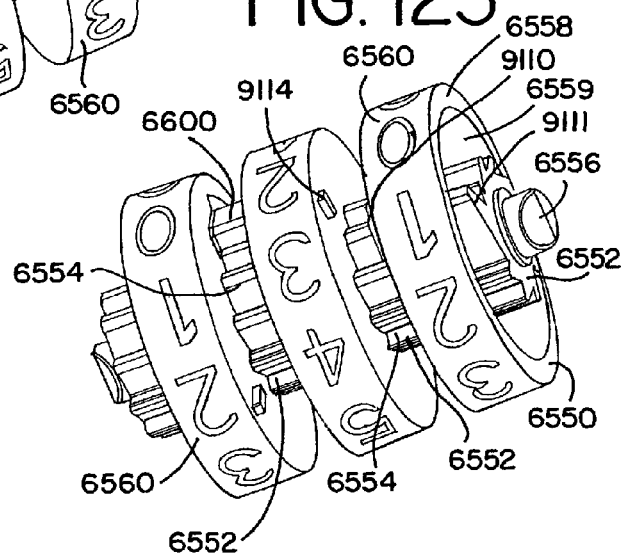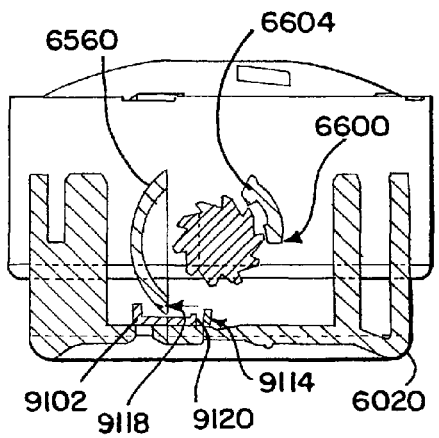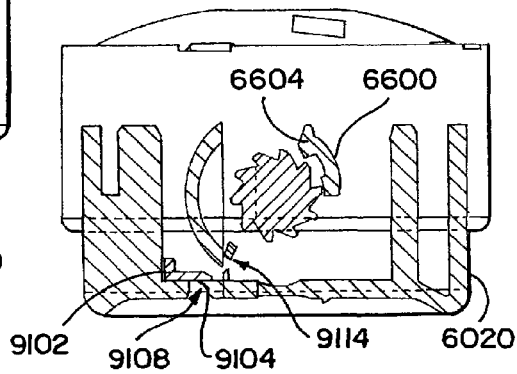

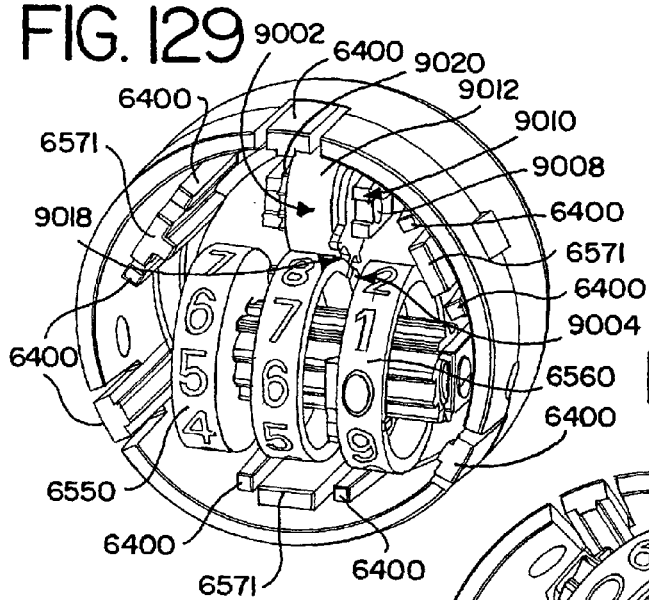
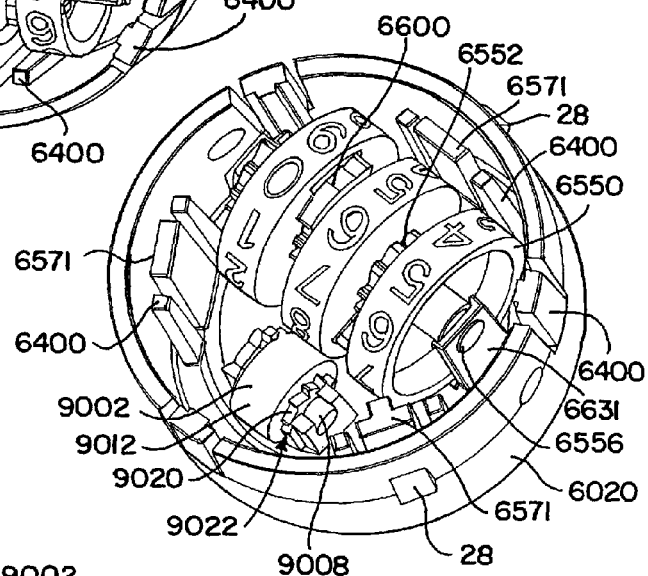
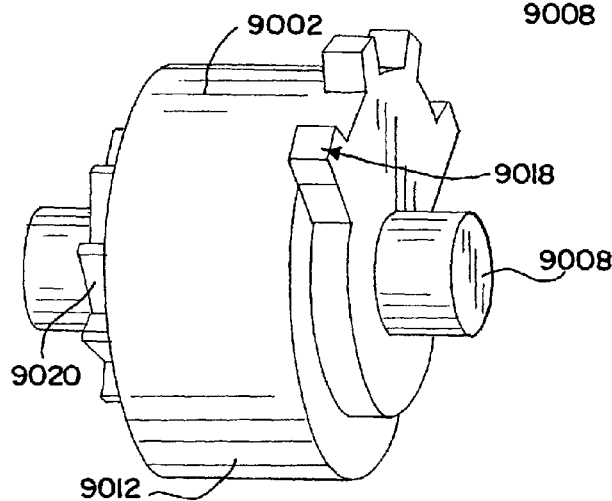

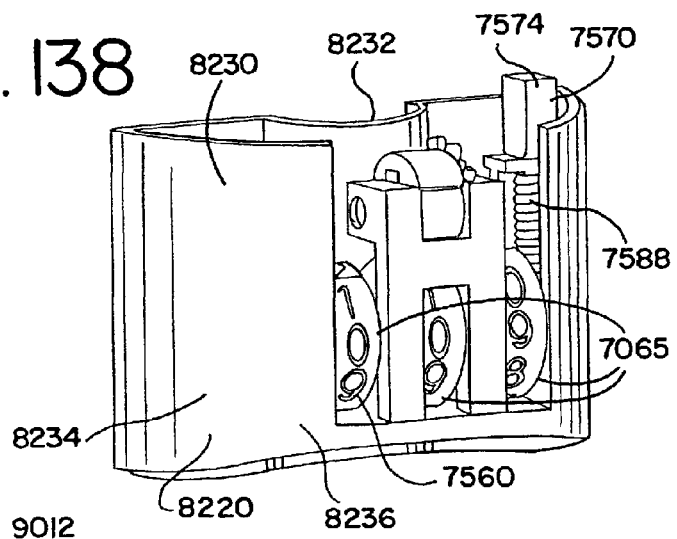
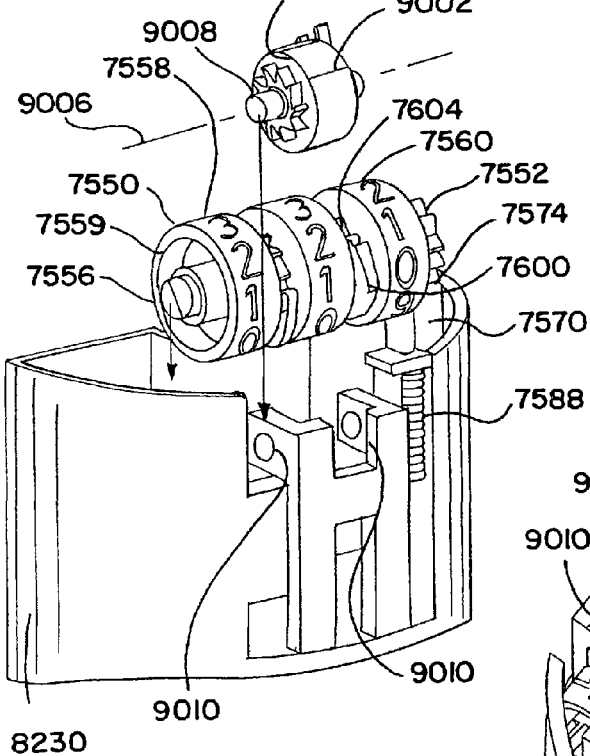
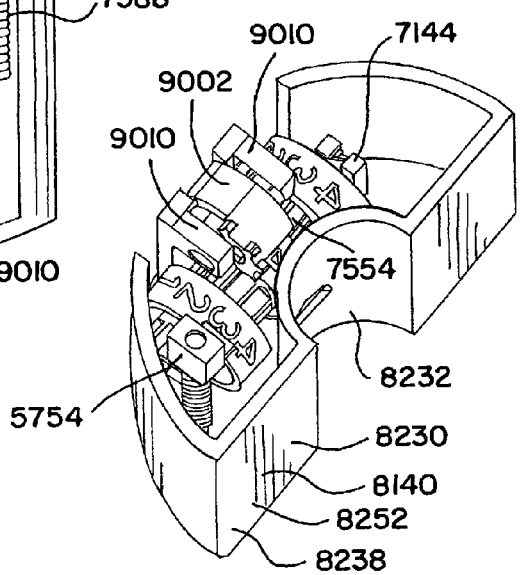
FIG. 138
FIG. 139
FIG. 140

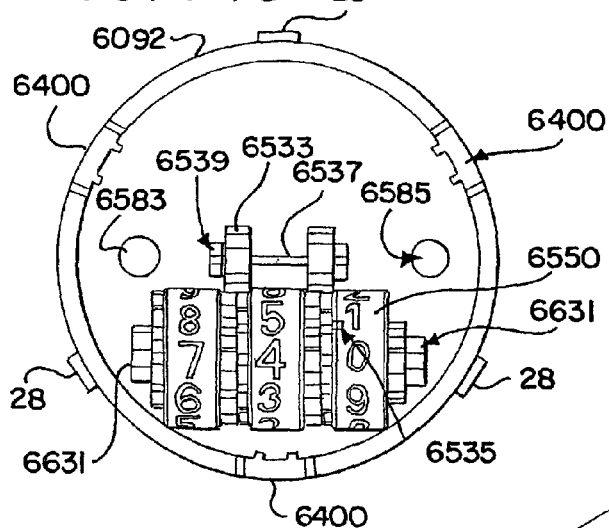
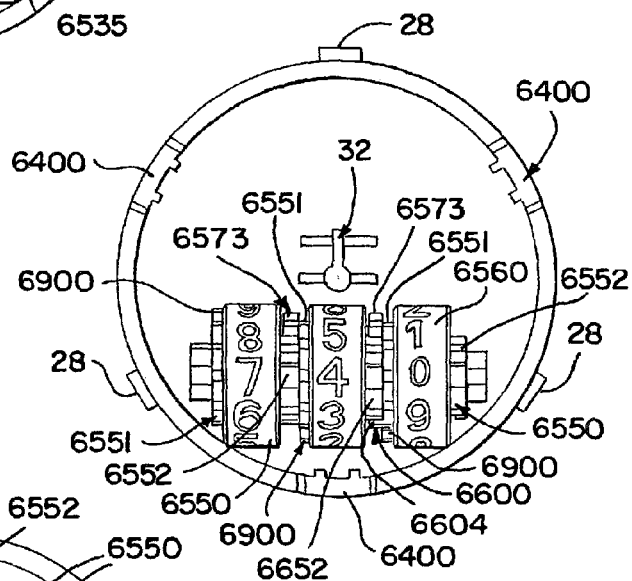
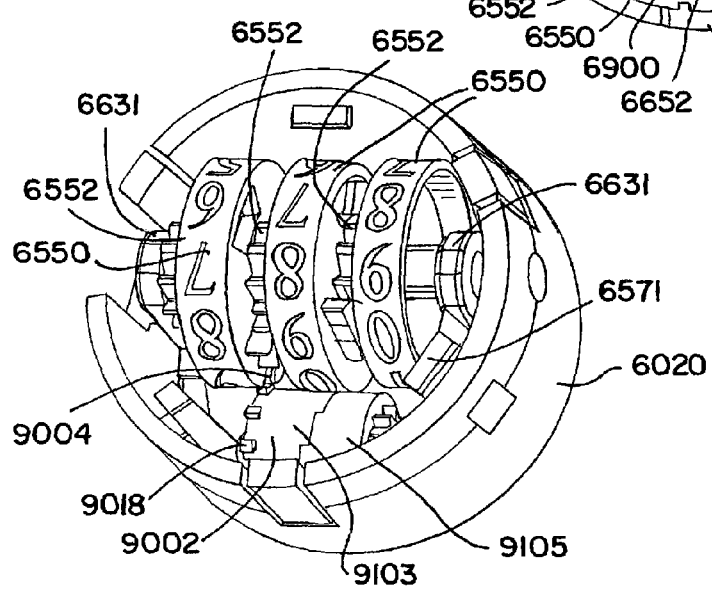
FIG. 145
FIG. 146
FIG. 147

INDICATING DEVICE WITH WARNING DOSAGE INDICATOR

This application is a continuation of U.S. application Ser. No. 12/579,129, filed Oct. 14, 2009, which is a continuation of U.S. application Ser. No. 10/968,815, filed Oct. 18, 2004, which claims the benefit of U.S. Provisional Application Ser. No. 60/515,316, filed Oct. 28, 2003, the entire disclosures of which are hereby incorporated herein by reference.

BACKGROUND

The present invention relates generally to an indicating device for indicating the number of dosages that have been dispensed from or remain in a container, and in particular, to an indicating device having at least a first and second indicator member with primary and secondary dosage indicia respectively.

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

Typically, a conventional aerosol container includes a body and a valve stem that can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered.

Although these actuator boots with indicators, or separate indicator devices, have provided the advantage of generally being able to keep track of the number of dosages, there remains room for improvement.

For example, many known indicating devices provide only a numerical indication of the number of doses of substance that have been dispensed from or remain in the container. As such, over the course of dispensing dozens and/or hundreds of doses of medicament, the user can become desensitized to the indicating device and may become caught unaware that the medicament in the container has been dissipated notwithstanding that the indicating device is working properly and provides an accurate accounting of the number of doses of medicament dispensed from or remaining in the container.

SUMMARY

Briefly stated, in one preferred embodiment, an indicating device suitable for indicating the number of dosages of a substance that have been dispensed from or remain in a container includes at least one first indicator member moveable to a plurality of positions and a second indicator member moveable in response to a predetermined number of movements of the at least one first indicator member. The at least one first indicator member includes primary dosage indicia adapted to indicate the number of dosages of substance that have been dispensed from or remain in the container. The second indicator member includes secondary dosage indicia adapted to indicate that less than a minimum predetermined number of dosages of substance remain in the container. In one preferred embodiment, the primary dosage indicia are configured as numerical indicia and the secondary dosage indicia are configured as color indicia.

In one preferred embodiment, the at least one first indicator member includes a plurality of coaxially mounted primary indicator members rotatable about a first axis of rotation. In various preferred embodiments, the second indicating member is rotatably mounted about a second axis of rotation, or is translatably moveable within a plane.

In another aspect, a device for dispensing dosages of a substance from the container includes a dispenser housing having a longitudinally extending cavity and a well located at a bottom of said cavity. The housing has an exhaust port communicating with the well. The container includes a valve stem extending longitudinally therefrom and moveable between a closed position and an open position. The valve stem dispenses one of the plurality of dosages of substance when moved to the open position. The container is disposed in the cavity of the dispenser housing with the valve stem being received within the well. The container is reciprocally moveable within the dispenser housing along the longitudinal extend of the cavity such that the valve stem is moved between the closed and open positions by engagement with the well.

In one preferred embodiment, the valve stem extends from the top of the container and the indicating device is disposed on the bottom of the container. In another embodiment, the indicating device is disposed in the bottom of the dispenser housing cavity adjacent the top of the container.

A method for indicating the number of metered dosages of medicaments dispensed from or remaining in the container is also provided.

The present invention provides significant advantages over other dispensing devices and indicating devices used therewith. In particular, the second indicator member, with its secondary dosage indicia, serves as an auxiliary indicator that provides the user with a warning that the container has less than a minimum predetermined number of dosages of substance remaining therein. For example and without limitation, the secondary indicia can include color indicia that changes once a predetermined number of actuations has occurred. In particular, user is provided with new indicia or stimulus that draws the user's attention and alerts the user that the container may be running low in the event that the user has become desensitized to the primary dosage indicia. In this way, the user is provided with advance warning that the container is running low, so as to thereby minimize the chance that they may be caught unaware with an empty container when in need of the substance, such as a medicament. Moreover, the auxiliary indicator can be incorporated with a minimal number of additional parts and is relatively robust in operation.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIG. 6 is an exploded perspective view of an alternative embodiment of the indicating device, including a base member, a cap member, an indicator member, a ratchet wheel and drive member and a spring.

FIG. 7 is a bottom perspective view of the cap member and indicator member of FIG. 6, with the indicator member mounted in the cap member.

FIG. 8 is an enlarged partial view of the indicator member and cap member of FIG. 7 showing an engagement of the indicator member by the cap member.

FIG. 9 is a bottom perspective assembly view of the cap member, indicator member, ratchet wheel, drive member and spring shown in FIG. 6.

FIG. 10 is an exploded perspective view of the base member and the cap member with the drive mechanism and indicator member mounted therein.

FIG. 11 is a perspective assembly view of the indicating device shown in FIG. 10.

FIG. 31 is an exploded side view of an indicating device and adapter being applied to the bottom of a container supported in a dispenser housing shown in cross-section.

FIG. 32 is a side view of an indicating device having an adapter applied to the bottom of a container supported in a dispenser housing shown in cross-section.

FIG. 33 is a side view of the indicator member and a lock member in a disengaged position.

FIG. 34 is a bottom view of the indicator member and lock member shown in FIG. 33.

FIG. 35 is a side view of the indicator member and lock member in an engaged position.

FIG. 36 is a bottom view of the indicator member and lock member shown in FIG. 35.

FIG. 38 is an exploded perspective view of the indicating device shown in FIG. 37.

FIG. 44 is an exploded perspective view of an alternative embodiment of an indicating device having indicator members with dosage indicia and an indicator member with usage indicia.

FIG. 45 is a bottom perspective view of the cap member shown in FIG. 44 with a usage indicator member installed therein and a dosage indicator member exploded out therefrom.

FIG. 46 is a bottom perspective view of a dosage indicator member shown in FIG. 44.

FIG. 47 is a perspective view of a reset assembly shown in FIG. 44.

FIG. 48 is a perspective view of the drive member shown in FIG. 44.

FIG. 49 is a bottom perspective view of the usage indicator member shown in FIG. 44.

FIG. 50 is a top perspective view of the usage indicator member shown in FIG. 44.

FIG. 54 is a side view of a first and second dosage indicator member with the reset member and drive member in a disengaged position.

FIG. 55 is a side view of a first and second dosage indicator member with the reset member and drive member in an engaged reset position.

FIG. 56 is a top perspective view of a first and second dosage indicator member, a usage indicator member and a drive assembly.

FIG. 57 is a bottom perspective view of the base member shown in FIG. 38.

FIG. 70 is a perspective view of a dispensing device with a viewing window revealing dosage indicia.

FIG. 71 is a perspective view of one embodiment of the dispensing device with a portion of the housing cut away.

FIG. 72 is a perspective view of one embodiment of the indicator assembly.

FIG. 82 is a top view of one embodiment of the indicator module.

FIG. 83 is a rear view of the indicator module shown in FIG. 82.

FIG. 84 is a cross-sectional view of the indicator module taken along line 84-84 of FIG. 82.

FIG. 85 is a cross-sectional view of the indicator module taken along line 85-85 of FIG. 82.

FIG. 86 is a cross-sectional view of the indicator module taken along line 86-86 of FIG. 82.

FIG. 87 is a cross-sectional view of the indicator module taken along line 87-87 of FIG. 82.

FIG. 88 is a perspective view of an alternative embodiment of the module.

FIG. 89 is a cross-sectional view of the indicator module taken along line 89-89 of FIG. 83.

FIG. 90 is an exploded view of a container, a key member and an indicator module.

FIG. 91 is a top view of the key member.

FIG. 92 is a cross-sectional view of the key member taken along line 92-92 of FIG. 91.

FIG. 93 is a perspective view of a container and an alternative embodiment of the indicator module mounted in a dispenser housing with a portion of the housing cut away.

FIG. 97 is a perspective view of one embodiment of an indicator member.

FIG. 98 is an opposite perspective view of the indicator member shown in FIG. 97.

FIG. 99 is a top perspective view of a second member of one embodiment of the indicator module with an axle installed therein.

FIG. 100 is a perspective view of an actuator member.

FIG. 101 is a perspective view of a container with an alternative embodiment of a key member installed thereon positioned above one embodiment of an indicator module.

FIG. 102 is a perspective view of an alternative embodiment of the key member.

FIG. 103 is an exploded perspective view of an alternative embodiment of a key member being applied to a container.

FIG. 108 is an exploded perspective view of an alternative embodiment of an indicator module and indicator assembly.

FIG. 109 is an enlarged side view of an actuator member in a disengaged position adjacent a first indicator member.

FIG. 113 is a cross-sectional view of an advancement member on a first indicator member, a second indicator member and an engagement member.

FIG. 114 is a cross-sectional view of the advancement member as it is first engaged by the engagement member.

FIG. 115 is a cross-sectional view of the advancement member as it is biased by the engagement member into engagement with the indicator member.

FIG. 116 is a cross-sectional view of the advancement member as it is further biased by the engagement member into engagement with the second indicator member.

FIG. 117 is a perspective view of an alternative embodiment of an indicator assembly disposed on a lower member of the module housing.

FIG. 118 is a perspective view of one embodiment of an indicating device having an auxiliary dosage indicator.

FIG. 119 is a bottom plan view of one embodiment of a cap member and indicator members.

FIG. 120 is a perspective view of the cap member and indicator members shown in FIG. 119.

FIG. 121 is a top plan view of the cap member and indicator members shown in FIG. 119.

FIG. 122 is a right perspective view of an assembly of a plurality of indicator members.

FIG. 123 is a left perspective view of the assembly shown in FIG. 122.

FIG. 124 is a partial side view of an indicating device, with various components shown in partial section cut and with a second indicator member shown in an intermediate display position.

FIG. 125 is a partial side view of the indicating device shown in FIG. 124 with the second indicator member shown in a final display position.

FIG. 126 is a partial side view of the indicating device, with various components shown in partial section cut and with a second indicator member being moved from an initial display position to an intermediate display position.

FIG. 127 is a top view of the indicating device with arrows illustrating the movement of the second indicator member from an initial display position to an intermediate display position and then to a final display position.

FIG. 128 is a top perspective view of another embodiment of an indicating device.

Figure 128:
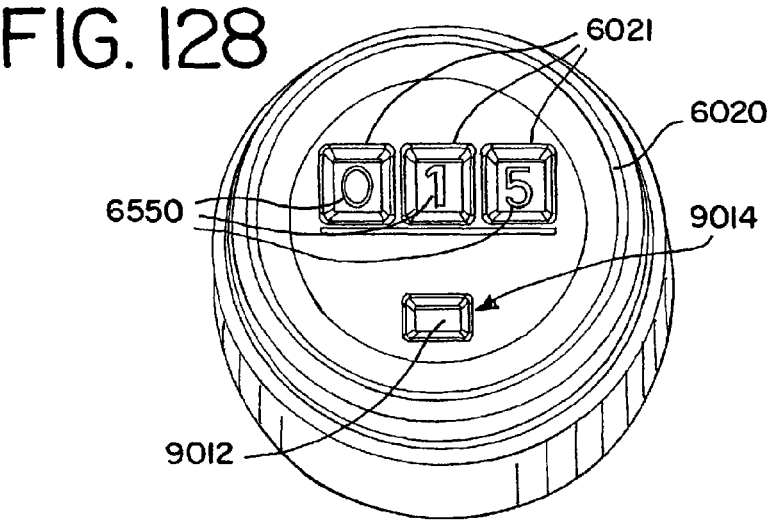

FIG. 129 is a left bottom perspective view of the cap member and indicator members shown in FIG. 128.

FIG. 130 is a right bottom perspective view of the cap member and indicator members shown in FIG. 128.

FIG. 131 is a perspective view of one of the indicator members shown in FIGS. 129 and 130.

Figure 132:
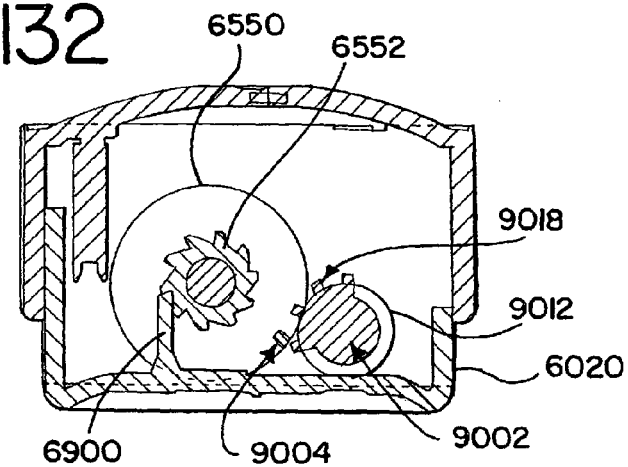

FIG. 132 is a partial side view of the embodiment of the indicating device shown in FIG. 128 with various components shown in partial section cut and with a second indicator member being advanced from a first position to a second position.

Figure 133:
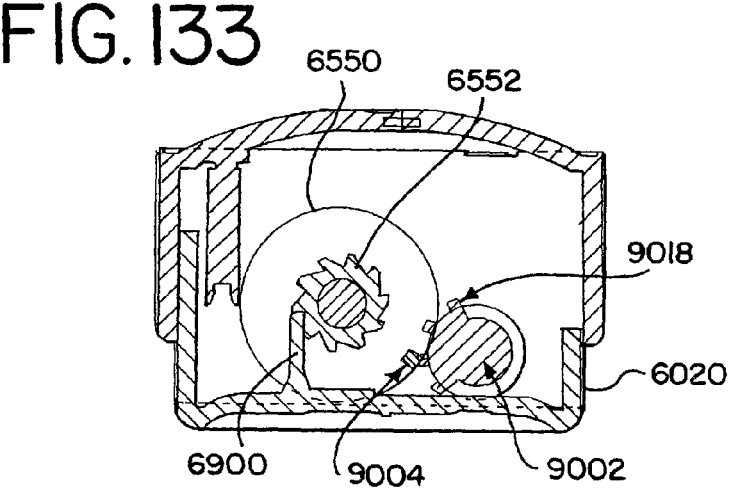

FIG. 133 is a partial side view of the indicating device shown in FIG. 130 with the second indicator member being advanced from a second position to a third position.

Figure 134:
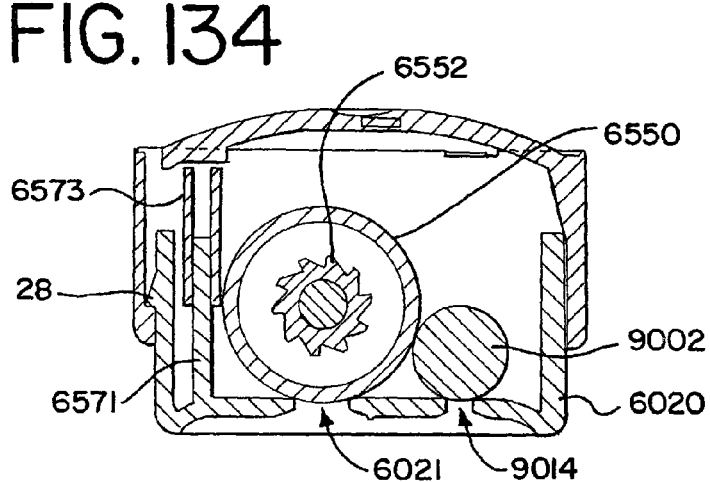

FIG. 134 is a partial cross-sectional side view of the indicating device shown in FIG. 128 with first and second indicator members visible through a pair of viewing windows.

Figure 135:
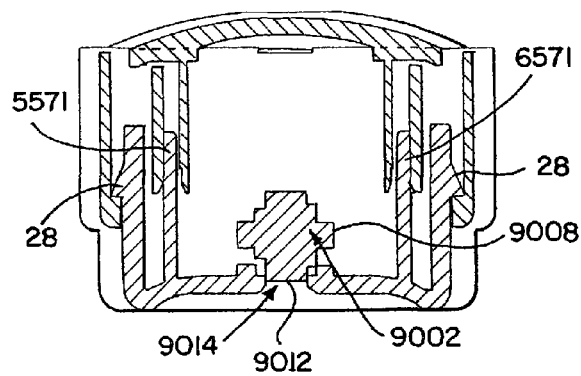

FIG. 135 is a partial cross-sectional side view of the indicating device shown in FIG. 128 with the second indicator member visible through a viewing window.

Figure 136:
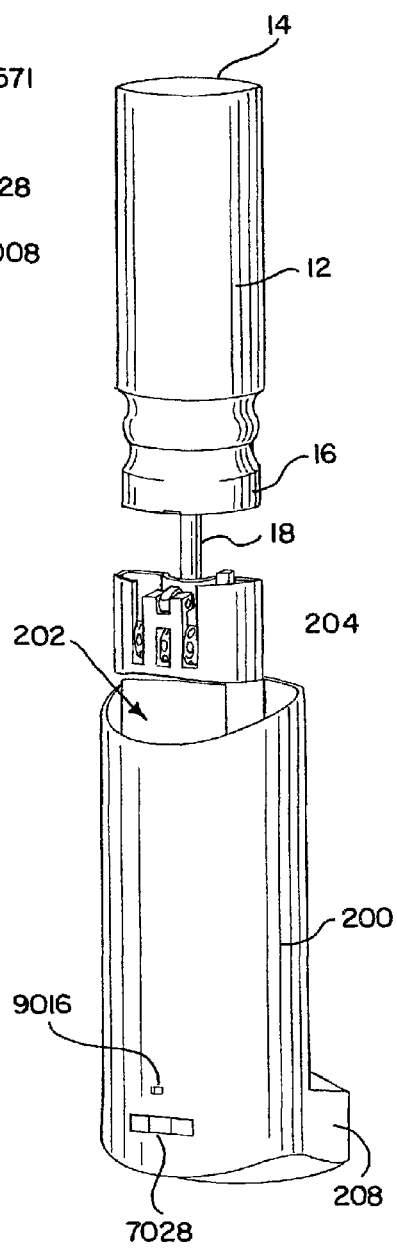

FIG. 136 is an exploded perspective view of a dispensing device including a dispenser housing, indicating device and container.

Figure 137:
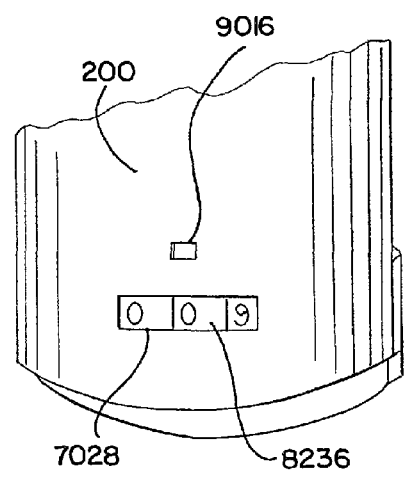

FIG. 137 is a partial perspective view of a first and second indicator members visible through windows provided in a dispenser housing.

FIG. 138 is a front perspective view of one embodiment of an indicating device.

FIG. 139 is an exploded perspective view of the indicating device shown in FIG. 138.

FIG. 140 is a top perspective view of the indicating device shown in FIG. 138.

Figure 141:
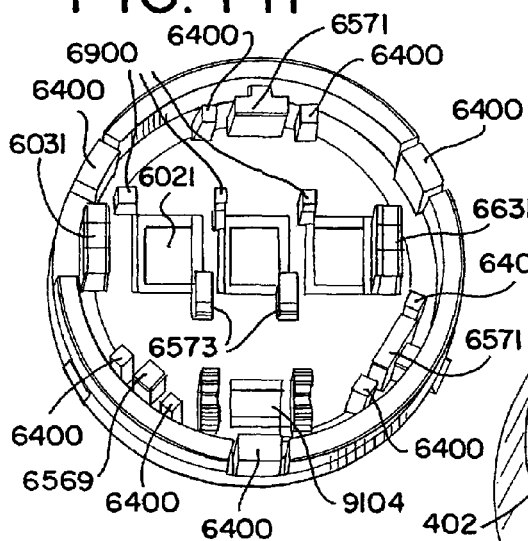

FIG. 141 is a top perspective view of one embodiment of a cap member.

Figure 142:
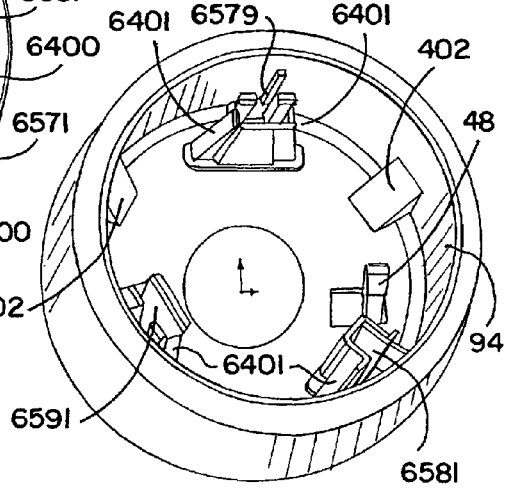

FIG. 142 is a top perspective view of one embodiment of a base member.

Figure 143:
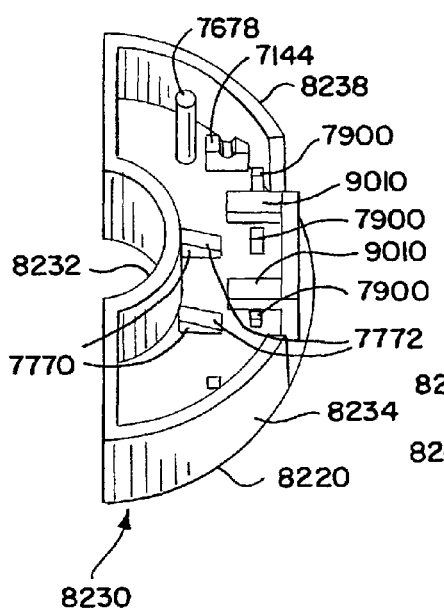

FIG. 143 is a top perspective view of one embodiment of one member of a module housing.

Figure 144:
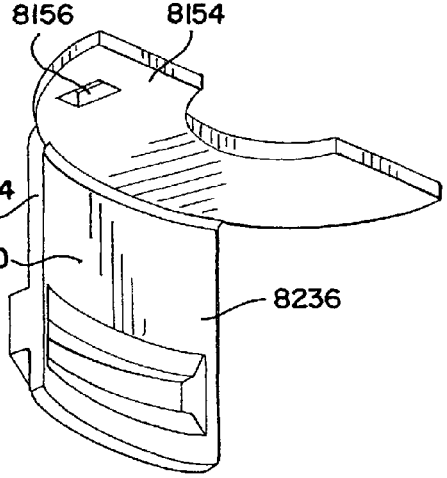

FIG. 144 is a bottom perspective view of one embodiment of a second member of a module housing.

FIG. 145 is a bottom plan view of an alternative embodiment of an primary indicating device installed in a cap member.

FIG. 146 is a bottom plan view of an alternative embodiment of a primary indicating device installed in a cap member.

FIG. 147 is a bottom perspective view of an alternative embodiment of a cap member and indicator members.

Figure 148:
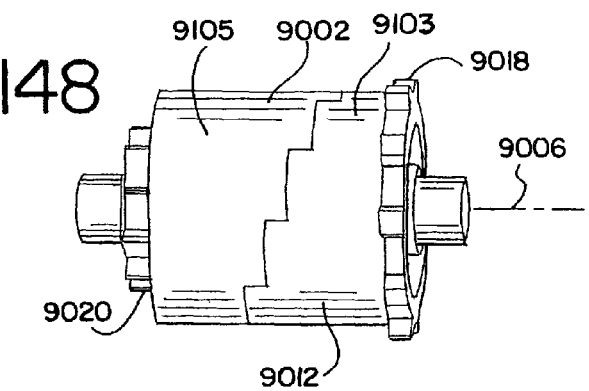

FIG. 148 is a perspective view of a secondary indicator member.

Figure 149:
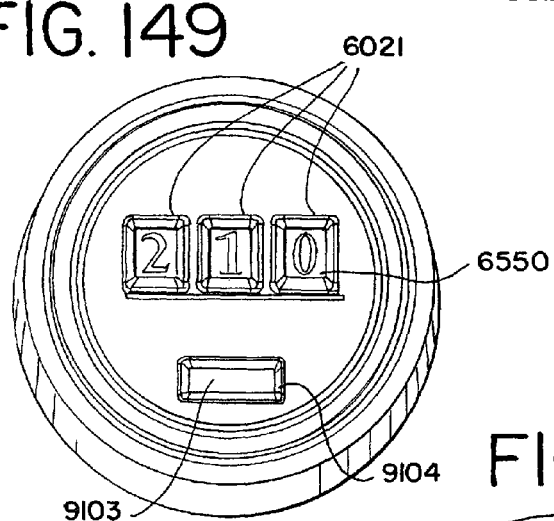

FIG. 149 is a top perspective view of an indicating device with primary and auxiliary indicating members indicating an initial number of dosages of substance remaining in a container.

Figure 150:
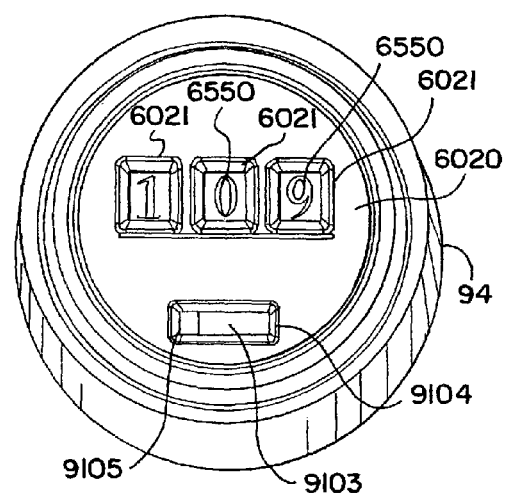

FIG. 150 is a top perspective view of the indicating device shown in FIG. 149 with primary and auxiliary indicating members indicating the number of dosages of substance remaining in a container.

Figure 151:
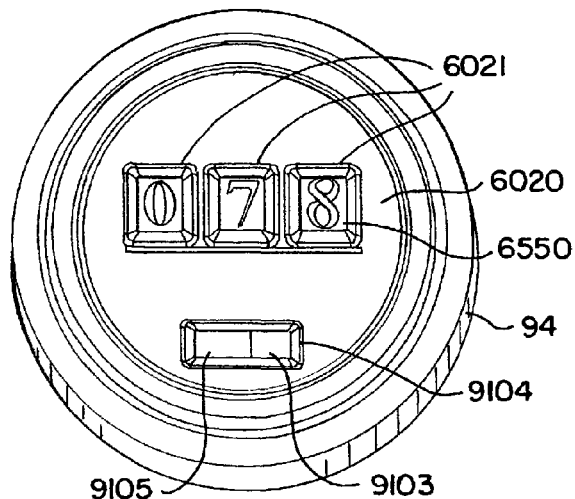

FIG. 151 is a top perspective view of the indicating device shown in FIG. 149 with primary and auxiliary indicating members indicating the number of dosages of substance remaining in a container.

Figure 152:
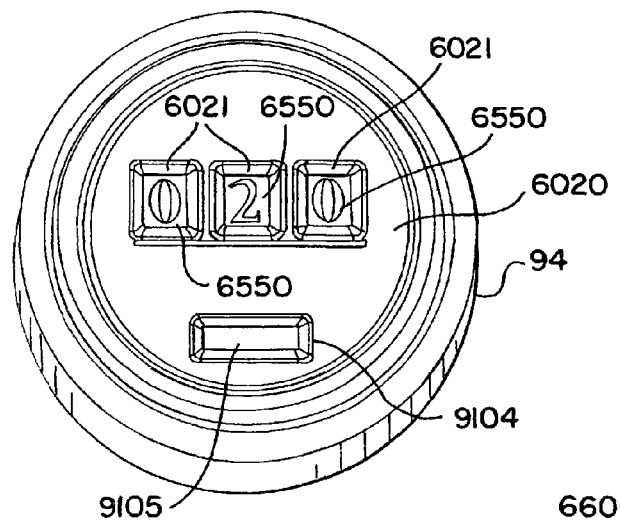

FIG. 152 is a top perspective view of the indicating device shown in FIG. 149 with primary and auxiliary indicating members indicating the number of dosages of substance remaining in a container.

Figure 153:
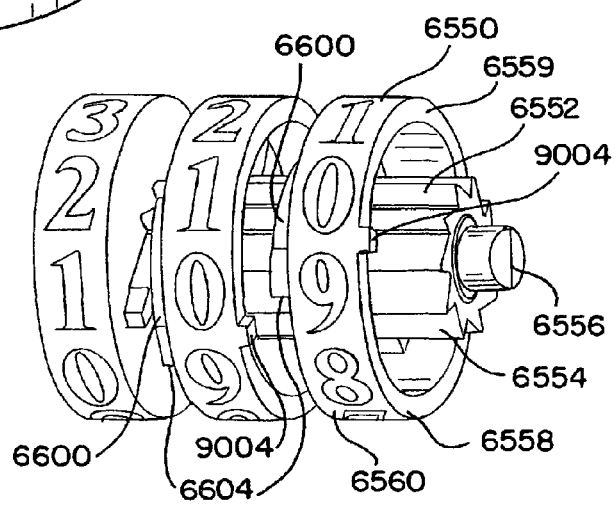

FIG. 153 is a perspective view of an alternative embodiment of an assembly of a plurality of indicator members.

DETAILED DESCRIPTION OF THE PRESENTLY PREFERRED EMBODIMENTS

General Description of Dispenser:

Referring to the drawings, and in particular FIGS. 31, 32, 136 and 137, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through an opening 204 and be installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIGS. 31 and 32. The terms "connect," "connected," "couple," and "coupled," and equivalents thereof, refers to the connection of two components directly, or indirectly, i.e., by way of one or more intervening components.

As shown in FIGS. 31 and 32, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

As shown in FIGS. 31, 32 and 136, the container 12 is cylindrical and has a hub 16 disposed on a top surface 17 thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a substance which is dispensed therefrom in specific metered doses by an actuation thereof effected by depressing or moving the valve stem 18 from an extended closed position to a depressed open position. Preferably the substance is a medicament, although it should be understood that the container may be used to hold a variety of non-medicinal substances, including, but not limited to, various liquids, foams or aerosols. In one preferred embodiment, the container is a pressurized, metered dose inhaler. A single metered dose is dispensed from the container by each reciprocal, longitudinal movement of the valve stem, or actuation of the container. It should also be understood that the valve system can be actuated by a variety of actuators, including, but not limited to, various pumps, levers, actuator boots, buttons and the like. In some embodiments, the container and valve system is breath-actuated, meaning they are actuated in response to the user inhaling, for example by inhaling through the mouthpiece. In such embodiments, the valve system can be actuated by an actuator moveable relative to the container and housing such that the container remains stationary relative to the housing.

In operation, the opening of the valve stem is effected by moving the container 12 reciprocally within the housing 200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of a substance through the well 214 and orifice 210. The substance, for example an aerosol and medicament, are then transmitted to the patient through the exhaust port 216 of the mouthpiece by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to any patent by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of a substance, such as a medicament, upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Figure 1:
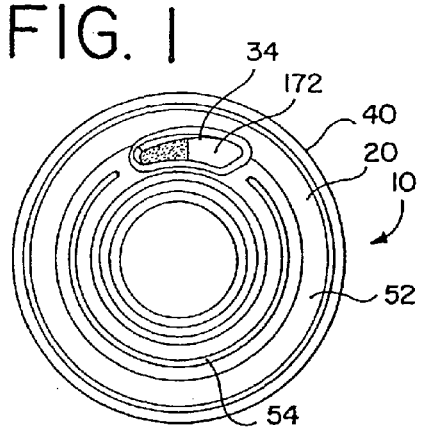
FIG. 1 is a top view of an indicating device having a viewing window.
Figure 69:
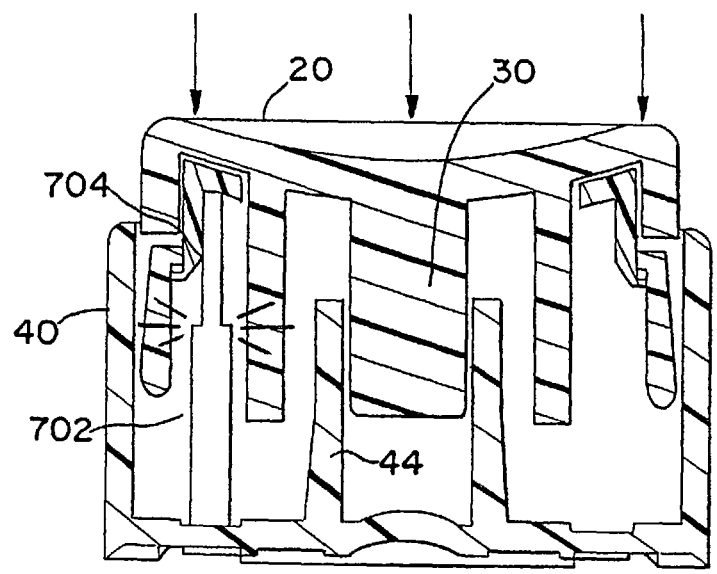
FIG. 69 is a cross-sectional view of another preferred embodiment of the indicating device with first and second lock members engaged after the final predetermined actuation of the container.

Description of Primary Indicating Devices Mounted to Bottom of Container:

Now generally referring to FIGS. 1-69, various primary dose indicating devices are shown. The primary indicating device 10 indicates the number of metered doses that have been dispensed from or remain in the container. As shown in the embodiments of FIGS. 1-3A and 10-11, respectively, the primary indicating device 10, 200, 500 includes an indicating device housing comprised of a cap member 20, 220, 520 disposed in a base member 40, 540. The base member 40 is configured such that it can be mounted to the bottom of the container 12. In a first embodiment, shown in FIGS. 2, 6 and 12-17, the base member includes a convex, or curved bottom portion 50, or floor, which is shaped to be received in and to mate with the bottom end 14 of the container, which has a concave or inwardly curved contour (see FIG. 2). The base member 40 is preferably connected to the bottom of the container, for example and without limitation by bonding with adhesive, double sided tape, or similar bonding agent. In one preferred embodiment, a label, or other wrapper, is wrapped around the side of the base and the container to join the base to the container. In one preferred embodiment, the outer circumferential surface of the base is substantially the same as outer circumferential surface of the container, which facilitates the joining thereof by way of a wrapper.

Figure 25:
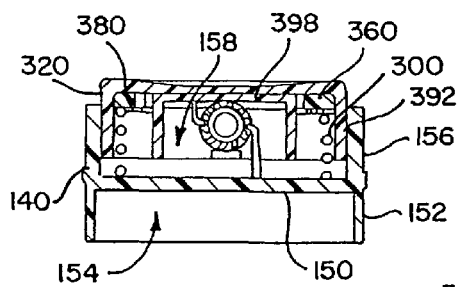
FIG. 25 is a cross-section view of the indicating device taken along line 25-25 of FIG. 24.

As shown in FIGS. 6 and 10-15, a circumferential skirt member 94 extends upwardly from the base portion to form a cavity 96. Alternatively, as shown in FIG. 25, the base member 140 includes a bottom portion 150, a downwardly depending circumferential skirt 152 and an upwardly depending circumferential skirt 156. Depending skirt 152 forms a recess or cavity 154 which is shaped to receive the bottom end of the container. The base member is fixedly mounted on the container by connecting one or more of the bottom portion or skirt to the container, for example and without limitation by bonding or by press fitting the container in the cavity 154 so as to provide an interference fit between the container and the depending skirt. The upwardly depending skirt 156 and bottom portion form an upper cavity 158 overlying the lower cavity 154.

In yet another embodiment, shown in FIGS. 29-32, an adapter member 90 is connected to one of the above-mentioned base members, for example and without limitation by way of bonding, an interference fit, a snap fit, or a threadable engagement. The adapter member 90 preferably has a cylindrical configuration and comprises a circumferential skirt 92 that is shaped to receive the bottom end of the container. Again, the adapter can be connected to the container, for example by way of bonding, an interference fit, or both. Adapters having different internal diameters can be provided such that a single indicating device having a modular base member can be mounted on various aerosol containers having a variety of outer diameters.

Alternatively, as shown in FIG. 57, the base member 1040 includes a downwardly depending circumferential skirt 1152 forming a recess 1154. The skirt 1152 includes one or more steps 1155 or shoulders, which form various inner diameters in the base member 1040. In this way, a single base member 1040 can be used with containers having different diameters. It should be understood that although only one step is shown, so as to thereby form two inner diameters on the skirt 1152, the base member could be configured with additional steps so as to provide a plurality of various inner diameters dimensioned to receive various containers by way of a friction fit. The skirt 1152 is also configured with a plurality of cut-outs, or slits 1153, which permit enhanced air flow around the base member in embodiments where the base member may be in close proximity to the area where the medicament or aerosol is being dispensed.

Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section.

Figure 1A:
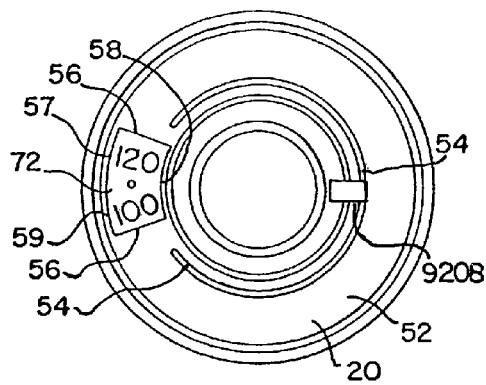
FIG. 1A is a top view of the indicating device showing an alternative embodiment of the viewing window with indicia visible therethrough.
Figure 1B:
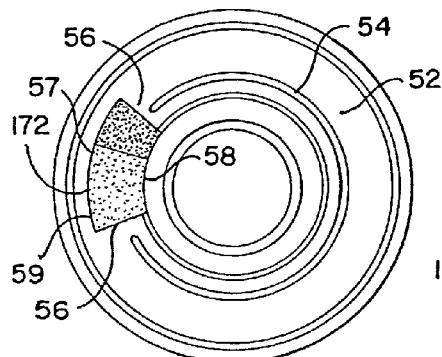
FIG. 1B is a top view of the indicating device showing an alternative embodiment of the indicia.
Figure 2:
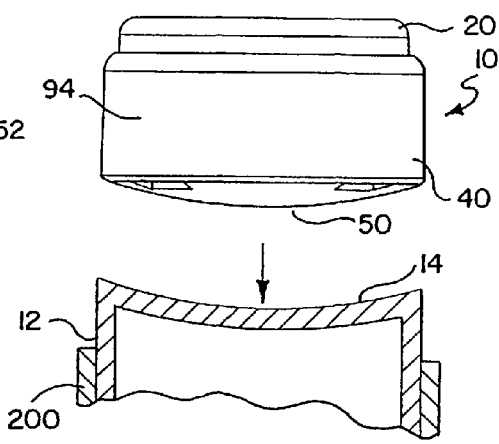
FIG. 2 is a side view of the indicating device being mounted to the top of a container shown in cross-section.

As best shown in FIGS. 1, 1A and 1B, the cap member 20 has a top portion 52 with a first viewing window 34, 59 formed therein. Preferably, the cap member 20 is circular and the viewing window is formed in the top portion adjacent the outer periphery of the cap member so as to overlie indicia applied to the top of an indicator member supported beneath the cap member. The viewing window can be configured in a number of various shapes. For example, the viewing window 34 can be tapered as shown in FIG. 1, or it can be an arcuate shaped window 59 bounded by coaxial inner and outer curved borders 57, 58 and radial side borders 56 as shown in FIGS. 1A and 1B. Of course, one of skill in the art should understand that any shaped window would work so long as the indicia is visible. The top of the cap member preferably has a plurality of raised portions 54 forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIGS. 4, 6, 38, 44 and 119 the cap member 20, 220, 1020, 2020, 6020 comprises a circumferential skirt 92, 292, 1092, 2092, 6092 depending downwardly from the top portion 52, 252, 1052, 2052, 6052. The skirt preferably has a smaller diameter than the upwardly depending skirt of the base member, such that the cap member skirt nests within the upwardly extending skirt of the base member. Alternatively, the cap member can be configured with a skirt having a larger diameter than the skirt of the base member such that the base member skirt nests in the cap member skirt. The cap member 20, 220, 1052, 2052 is moveably mounted to the base member 40, 1040, 2040 by way of a snap fit.

In particular, as shown in FIGS. 5, 6, 7, 9, 10, 16, 29 and 44, the cap member includes a plurality of engagement members 28, 228, 428 extending from an outer circumferential surface of the skirt. The cap member 20, 220, 420 is inserted axially within the recess or cavity 96 of the base member such that the engagement members 28, 228, 428, which have a tapered surface, slide past the rim 42 of the base member skirt until the engagement members are disposed in a plurality of pockets 43 formed along the inner circumferential surface of the base member skirt to form a snap-lock fit. In particular, the upper surface of the engagement member engages an engagement surface 45 defining the top of the pocket. In this way, the cap member is moveable with respect to the base member along an axial, or longitudinal, path. Alternatively, the rim of the base member can be curved slightly inward such that the engagement members engage the inwardly curved rim portion so as to prevent the cap member from being separated from the base member.

The axial movement of the cap member 20, 220, 1020, 2020 relative to the base member 40 is bounded or constrained by the engagement of the engagement members with the top of the base member pockets (or the base member rim) at a fully extended position and by engagement of a bottom rim 21, 221, 1021, 2021 of the cap member skirt with the upper surface of the bottom portion at the bottom of the stroke as shown for example in FIGS. 12-15. One of skill in the art should understand that the engagement members can alternatively be formed on the base member skirt so as to engage pockets or openings, or a rim (or like protrusion), formed on the cap member skirt.

As shown in FIGS. 6, 9, 16 and 17, a spring 100 is disposed between the cap member and the base member. The spring is preferably disposed in a downwardly extending hub portion 30, 230 of the cap member (shown in FIGS. 4 and 6) and an upwardly extending hub portion 44 (shown in FIGS. 10, 16 and 17) of the base member, which are received one in the other. Alternatively, as shown in FIG. 25, a spring 300 is disposed between the cap member and base member and is of such a size that the coils are positioned adjacent the inner circumferential surface of the cap member skirt 392. The spring 100, 300 functions as a return mechanism and biases the cap member 60, 260, 360 upwardly in the base member such that the engagement members 28, 228 of the cap member engage the upper portion of the pockets of the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

Figure 4:
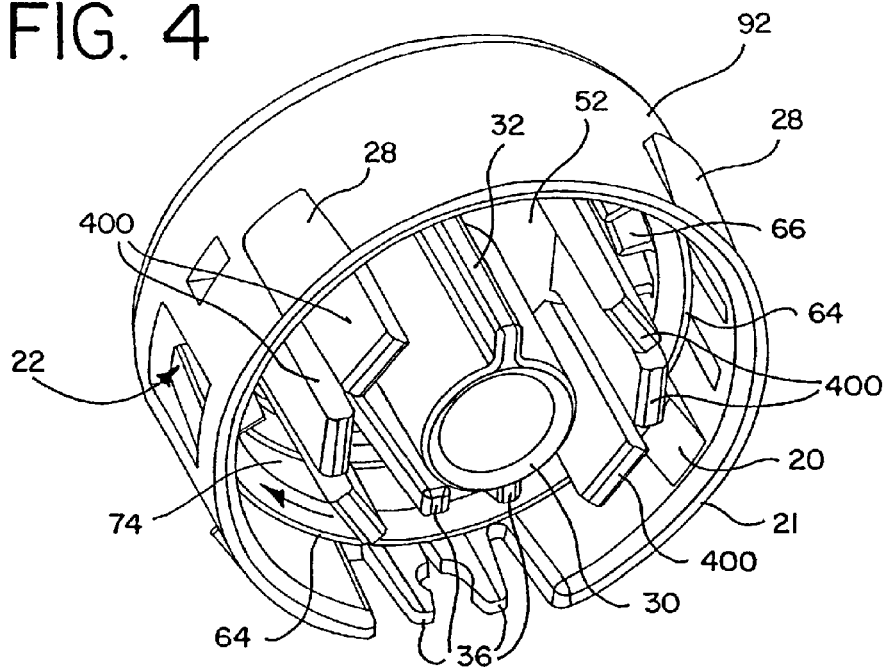
FIG. 4 is a bottom perspective view of the cap member with the indicator member mounted therein.
Figure 5:
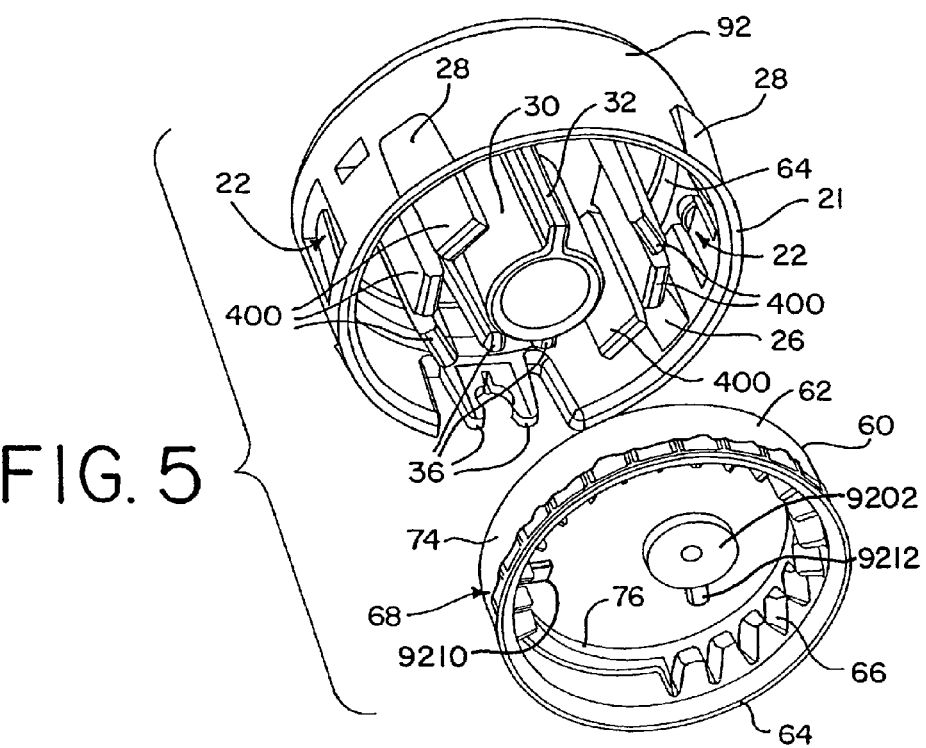
FIG. 5 is an exploded perspective view of the cap member and indicator member shown in FIG. 4.
Figure 39:
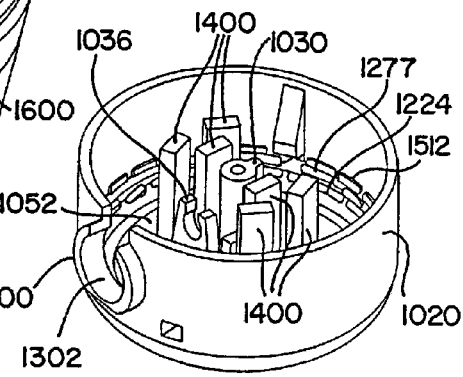
FIG. 39 is a bottom perspective view of the cap member shown in FIG. 38.

As shown in FIGS. 4, 5, 16, 17, 45, 119, 141 and 142, the return mechanism acting between the cap member and base member includes a plurality of resilient arm members 400, 2400, 6400 extending downwardly from the cap member. As the cap member is moved toward the base member, one or more of the arm members engages a ramped biasing surface 402, 6401 formed along an outer portion of the hub portion 44, or along the inside of the circumferential skirt 94. The ramped biasing surface biases one or more of the resilient arm members outwardly as the cap member moves toward the base member. As shown in the embodiment of FIGS. 4 and 5, six arm members 400 are arranged circumferentially around the hub portion 30. Alternatively, as shown in the embodiment of FIG. 39, six arm members 1400 are arranged in an "X" pattern around the hub 1030 so as to conserve space and provide additional room under the cap member 1020. Corresponding ramps, or ramped biasing surfaces are similarly arranged in the base member 1140. In yet another embodiment, shown in FIGS. 119, 141 and 142, the arm members 6400 are integrally formed in the circumferential skirt 6092 of the cap member and also adjacent various guide members 6571, 6569. The guide members are received in guides 6579, 6581, 6591 formed in the base member. Referring to FIGS. 141 and 142, one of the guide members 6569 is shaped to be received in only one of the guides 6581, such that the cap member can be properly installed with the various indicator members connected thereto aligned with the pawl 48 formed in the base member. The guides and guide members further act as key members to prevent the cap member from rotating relative to the base member. The guides can take any shape, for example rectangular or T-shaped. Alternatively, as shown in FIG. 145, a pair of guide members 6583, 6585 have different shapes, e.g., diameters, that are received in matingly shaped guides formed in the base member. Again, the unique shapes of the guide members and guides ensures that the cap member is properly aligned with the base member as those components are being secured one to the other.

Figure 16:
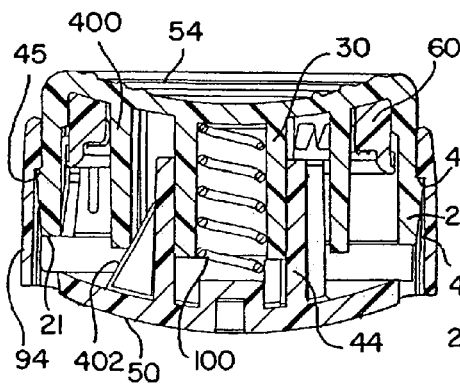
FIG. 16 is a cross-sectional view of the indicating device taken through the middle of the indicating device and showing engagement members disposed in pockets formed in the base member.
Figure 17:
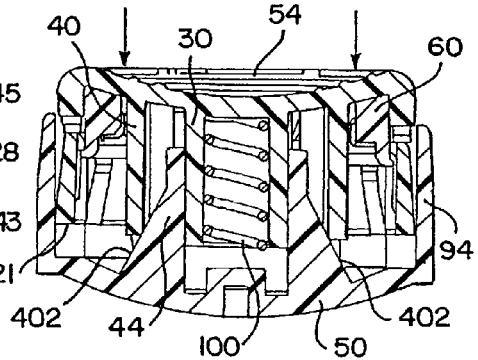
FIG. 17 is a cross-sectional view of the indicating device taken through the middle of the indicating device and showing an alternative return mechanism for the cap member.
Figure 18:
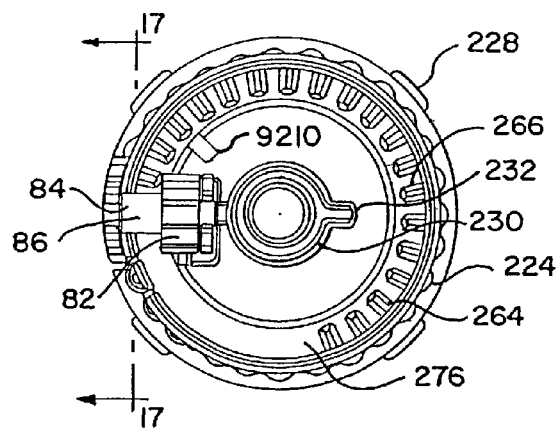
FIG. 18 is a bottom view of the assembly of FIG. 9 (without the spring) at initial setting before a first actuation of the indicator device and container.

The resilient arm member(s) act as cantilever springs to bias the cap member away from the base member when the cap member is released by the user. One of skill in the art should understand that the resilient arm members can also be formed on the base member so as to engage a ramped surface formed on the cap member. One of skill in the art should also understand that the spring and resilient arm members can be used together, as shown in FIGS. 16 and 17, or separately. In addition, it should be understood that one or more arm members and/or ramps may be used, with the size and shape of the arm member and/or ramp members being modified to provide more space between the cap member and base member.

As shown in FIGS. 4, 6, and 44 a key member 32, 232, or alignment rib, extends radially from the cap member hub portion 30, 230. As shown in FIG. 10, a key hole 47, or slot, is formed in a radially extending portion of the hub portion 44 of the base member. The slot extends radially from the opening in the hub portion. During assembly, the key member of the cap member is received in the key hole of the base member so as to prevent rotation therebetween.

Referring to the various embodiments of FIGS. 4-9, 12-15, 38, 40, and 44-46, a dosage indicator member 60, 260, 1060, 2060 is rotatably mounted in the cap member 20, 220, 1020, 2020 about an axis substantially parallel to the axial movement of the cap member relative to the base member. The indicator member is generally open in the middle and includes a top portion 76, 276, 1076, 2076 having an upper surface 62, 262 that rotatably slides along a bottom surface of the top portion of the cap member. Alternatively, the indicator member can be mounted on the outside of the cap member with a viewing window formed in the indicator member for viewing indicia applied to the top of the cap member.

As shown in the embodiments of FIGS. 5, 6, 38 and 44, the indicator member 60, 260, 1060, 2060 includes a circumferential skirt 74, 274, 1074, 2074 depending downwardly from the top portion. Referring to FIGS. 5 and 8, a plurality of protrusions 26, 226, or engagement tab members, extend from an inner circumferential surface of the cap member skirt and engage a rim 64, 264 formed on the bottom of the indicator member skirt. Alternatively, the indicator member can include an engagement member, or rim, that engages a groove or similar opening in the cap member. In this way, the indicator member is secured to the cap member so as to prevent axial movement therebetween but where the indicator member is permitted to rotate relative to the cap member. The indicator member is installed by snap-fitting the indicator member within the cap member. One of skill in the art should understand that the indicator member could alternatively be rotatably mounted on the cap member hub portion (having a portion of the key member cut away), or on a similar axle secured to the cap member.

Figure 26:
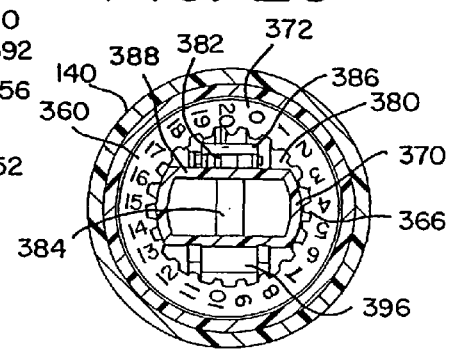
FIG. 26 is a cross-section view of the indicating device taken along line 26-26 of FIG. 23.

In yet another alternative embodiment, shown in FIGS. 25 and 26, a plate member 380 holds the indicator member 360 against the inner surface of the top portion of the cap member 320, wherein the spring 300 engages a bottom surface of the plate member 380 to bias a top portion 398 of the plate member against the cap member 320 and the cap member away from the base member. The indicator member 360 is nested in the recess formed between an outer flat portion of the plate member and the bottom surface of the cap member. Referring to FIG. 26, the drive assembly is mounted to the plate member 380 by inserting axle 384 through openings in downwardly extending walls 388 of the plate member. An enlarged portion 396 on the end of the axle engages one of the walls, while the ratchet wheel 382 and drive member 386 are mounted to the other end of the axle to complete the assembly. A top portion of the plate member abuts the cap member.

Figure 40:
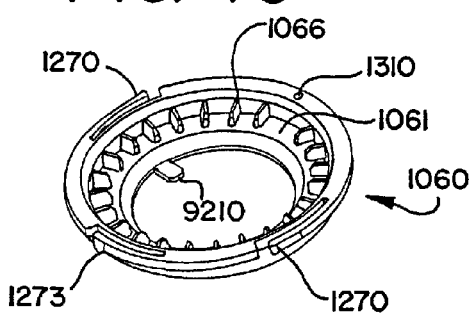
FIG. 40 is a bottom perspective view of a dosage indicator member shown in FIG. 38.

As shown in the embodiments of FIGS. 4-9, 40 and 46 the indicator member 60, 260, 1060, 2060 has a plurality of inwardly facing teeth 66, 266, 1066, 2066 formed around the inner circumference of the skirt. As shown in FIGS. 5, 6, and 40, the teeth are preferably formed about only a portion of the circumference, such that a gap 1061 is formed therebetween.

Alternatively, as shown in the embodiment of FIGS. 25 and 26, the indicator member 360 has a plurality of teeth 366 formed radially inwardly about an inner rim of an opening formed in the indicator member, which is configured as a relatively flat ring that does not include a skirt. In yet another embodiment, shown in FIG. 29, the plurality of teeth 466 extend axially downwardly from a ring-like indicator member 460.

As shown in the embodiments of FIGS. 5 and 44-46, the indicator member 60, 2060 includes a plurality of indentations 68, 2068 formed about the outer circumferential surface of the skirt 74, 2074. The cap member includes a pair of upwardly extending resilient indexing members 22, 2022 each having an end portion that engages one of the indentations so as to releasably engage the indicator member and prevent rotation therebetween. The angular distance between the indentations 68, 2068 is substantially the same as the angular distance between the plurality of indicator member teeth 66, 2066. In this way, the indexing member selectively engages the next indentation upon each incremental advancement of the indicator member defined by the distance between adjacent teeth. In the embodiment shown in FIG. 46, the indentations are preferably formed as ratchet teeth which only permit one-way rotation of the indicator member 2060 relative to the cap member.

Alternatively, as shown in the embodiments of FIGS. 6 and 38-39, the indentations and indexing member are reversed, i.e., the indentations 224, 1224 are formed about an inner circumferential surface of the cap member skirt and, and shown in FIG. 6, an indexing member 270 depends downwardly from the indicator member in a void formed in the skirt of the indicator member, or, as shown in FIG. 38, a pair of index members 1270 are configured as flexible arms formed along a rim portion 1078 along the bottom edge of the skirt 1074. In the embodiment shown in FIGS. 38, 39 and 40, the interaction between the index members 1270 and the indentations 1224, which are preferably shaped as ratchet teeth, function to index the indicator member by holding it in place between actuations of the cap member and also to prevent the backward rotation of the indicator member 1060. It should be understood that one or more index members can be engaged with a plurality of indentations, preferably formed as ratchet teeth, to control the rotational movement of the indicator member, regardless of whether the index members or indentations are formed on the cap member or the indicator member.

In yet another alternative, shown in FIG. 26, the plate member 380 includes a resilient indexing member 370 that engages one of the plurality of teeth 366 to selectively engage the indicator member so as to prevent the inadvertent rotation thereof. Alternatively, the indexing member can extend from the cap member.

Figure 24:
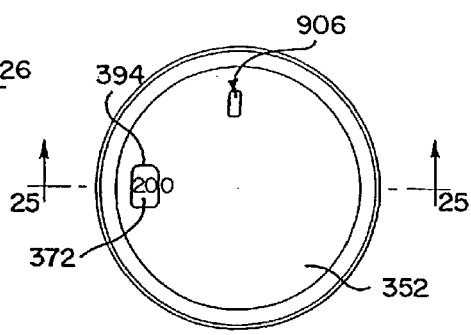
FIG. 24 is a top view of the indicating device shown in FIG. 23.

As shown in FIGS. 1A and 1B, primary dosage indicia 72, 172 in the form of numbers or color codings are provided on the top surface of the indicator member and are visible to the user through the viewing window 34, 59 provided in the top of the cap member. Alternatively, as shown in the embodiment of FIGS. 24 and 26, a zero is positioned adjacent a rectangular viewing window 334, preferably by permanent etching, to indicate a multiplication by ten of the indicia visible in the viewing window. One and two digit primary dosage indicia 372 are formed on the top of the indicator member 360 such that a three digit number is indicated to the user.

Figure 3:
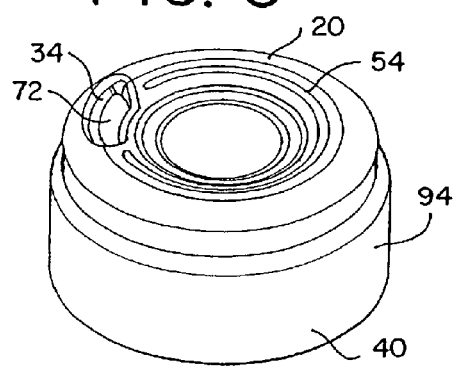
FIG. 3 is a top perspective view of the indicating device with the viewing window positioned in the top of the cap member.
Figure 3A:
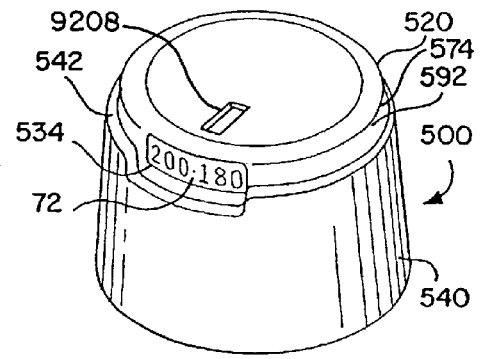
FIG. 3A is a top perspective view of the indicating device with the viewing window positioned along a side portion of the cap member.

In yet another alternative embodiment shown in FIG. 3A, the viewing window 534 is formed in an upper portion of the downwardly depending circumferential skirt 592 of the cap member. The primary dosage indicia are applied to the outer circumferential surface of the indicator member skirt 574 so as to be visible through the window. In this embodiment, a rim 542 of the base member is preferably scalloped in alignment with the viewing window 534 to provide an unobstructed view of the indicia and to inform the user as to the location of the viewing window.

One of the skill in the art should understand that other primary dosage indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid 172 displayed in the viewing window (as shown, e.g., in FIG. 1B) could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container should be replaced, or, conversely, to go from the starting predetermined number to 0 (or some ending number), which again indicates to the user that the container should be replaced.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel. In various preferred alternative embodiments, one or both of the base member and cap member can be made of polycarbonate.

Referring to FIGS. 5-9 and 12-18, a drive mechanism is shown as including a drive assembly 80. The drive assembly includes a ratchet wheel 82 coaxially mounted to a drive member 86 on an axle 84. The ratchet wheel, drive member and axle can be made separately, with the ratchet wheel and drive member then mounted on the axle, or all three parts can be integrally molded as a one-piece component. The drive assembly is preferably made of hard plastic material such as Acetel.

Figure 42:
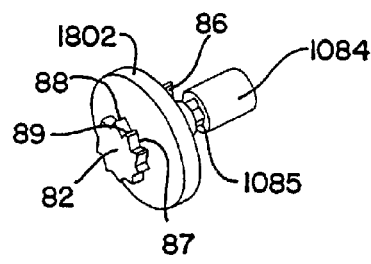
FIG. 42 is a perspective view of a drive assembly and dosage indicator member shown in FIG. 38.

In an alternative embodiment, shown in FIGS. 38 and 42, the drive assembly further includes a second primary dosage indicator member 1800 coaxially mounted with and between the drive member 86 and ratchet wheel 82. The indicator member 1800 is configured as a wheel and preferably includes primary dosage indicia positioned around the peripheral surface 1802 thereof. Preferably, the indicia are comprised of consecutive numerals running from 0 to 9.

In yet another alternative embodiment, shown in FIG. 44, the drive assembly includes a ratchet wheel 82 coaxially mounted with an indicator member 1800. The drive member 86 is formed separately from the ratchet wheel and indicator member and includes a single tooth 89 that is dimensioned to be received in a groove 1801 formed in a collar 1082 extending axially from the indicator member 1800. The tooth 89 of the drive member 86 is received in the groove 1801 of the collar and can be moved axially with respect to the collar, ratchet wheel and indicator member.

The ratchet wheel 82 includes a plurality of teeth 88 (preferably ten) formed around its periphery. Each of the teeth includes an engagement surface 89 and a tapered surface 87. As noted above, the drive member 86, whether integrally formed with the ratchet wheel or separately connected thereto, includes a single tooth 81 extending radially from the axle 84, or drive member collar.

In the embodiments shown in FIGS. 5, 6 and 45, the drive assembly is mounted to the cap member by engaging opposite ends of the axle 84 with downwardly extending hub portions 36, 236, 2236 such that the axle, ratchet wheel and drive member rotate about an axis substantially perpendicular to the axial movement of the cap member relative to the base member and to the axis of rotation of the indicator member. Alternatively, the drive assembly can be mounted to the base member, along with the indicator member, in a similar manner.

Alternatively, as shown in the embodiment of FIGS. 38-39, the axle 84 is received in a single hub 1036, or flexible snap enclosure rib. In this embodiment, the drive assembly further includes a ramp 1083, which ramps up to a plurality of radially extending teeth 1085 formed around the rotational axis of the drive assembly. A larger diameter axle 1084 extends outwardly from the teeth. A reset member 1106 includes a grippable wheel portion 1107 and a collar 1109 that is dimensioned to be received in a laterally facing opening 1302 formed in the skirt of the cap member. A bearing support 1300 is formed around the periphery of the opening so as to provide support for the collar. The reset member 1106 further includes four flexible, resilient fingers 1304 extending axially from the collar 1109. Each finger 1304 includes an engagement portion 1306 extending radially inward from the end of the finger. The engagement portion is shaped to engage one of the teeth 1085 formed on the drive assembly. A protrusion 1308, or rib, is formed on one of the fingers so as to extend radially outward therefrom. The protrusion 1308 acts as a drive portion and engages a downwardly depending protrusion 1310 formed on the bottom of the indicator member adjacent the gap 1061 formed between the teeth on the indicator member, as shown in FIG. 40. Preferably, the protrusion 1310 is positioned so as to be at the angular midpoint between the two teeth spanning the gap.

As shown in FIGS. 12-15, the drive mechanism further includes a pawl member 48, shown as a flexible rod or finger, which extends upwardly from the bottom portion of the base member and selectively engages one of the teeth of the ratchet wheel. The base member with the pawl are referred to and function as an actuator for the indicating device as the base is connected to and engaged by the container. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member 238, also shown as a flexible rod or finger, extends downwardly from the top portion of the cap member and selectively engages another of the teeth 88 of the ratchet wheel. It should be understood that the pawl member could alternatively extend from the cap member (and the non-return member from the base member) when the drive assembly is mounted to the base member, as described above. Of course, when formed integrally with one or the other of the cap member and base member, the pawl member and non-return member are preferably made of the same materials as the respective cap member and base member.

Referring to FIGS. 118-123, 132, 133, and 145-153, a plurality of primary indicator members (shown as three) 6550 are coaxially mounted on an axle 6556 and rotatable thereabout. The ends of the axle are supported on a pair of hearing supports 6631 formed in the cap member 6020. As best shown in FIGS. 122 and 123, each of the indicator members includes an indicator wheel 6558 having a circumferential skirt 6559 with an outer circumferential surface 6560 on which indicia (shown as numbers) are applied, and a ratchet gear 6552 coaxially mounted with the indicator wheel. Referring to FIGS. 118, 128, 134 and 149-152, a plurality of primary viewing windows 6021 are formed in the top portion of the cap member such that the indicia are visible in the windows. In one embodiment, first and second rings are visible in a viewing window, as shown for example in U.S. Pat. No. 6,283,365, which is hereby incorporated herein by reference. If should be understood that a single window could be provided, with all of the indicia visible through the window.

The indicator wheel and ratchet gear have an opening shaped to receive an axle. Alternatively, the middle indicator member is integrally formed with an axle portion extending from opposites sides thereof, with the other indicator wheels mounted thereon. The axle can be formed with an asymmetrical cross-section, e.g., a T-shaped cross-section, such that the axle is non-rotatably secured to the indicator wheels. The ratchet gear 6552 includes a plurality of teeth 6554 formed around its periphery. The ratchet gear is preferably integrally molded with the indicator wheel, although it should be understood that the gear and wheel can be made separately and thereafter attached one to the other by welding, adhesive and the like.

Referring to FIGS. 122-125, 130, 146 and 153, in one embodiment of the indicator member, a resilient advancement member 6600 extends from the indicator wheel. The advancement member 6600 includes a tooth portion 6604 having an engagement surface. The three indicator members are coaxially mounted such that the tooth portion 6604 of the advancement member of a first indicator member overlies the ratchet gear teeth 6652 of the second indicator member, and such that the tooth portion of the advancement member of the second indicator member overlies the ratchet gear teeth of the third indicator member. When only three indicator members are used, the third indicator member does not require an advancement member, although for the sake of simplicity in manufacturing, a modular indicator member with the same indicia applied thereto and the same advancement member formed thereon can be used for each of the first, second and third indicator members. It should be understood by one of skill in the art that one or more indicator members may be used to provide an indication of dosages used or available, and that the three indicator members shown in the Figures is meant to be illustrative, rather than limiting. In addition, it should be understood that a plurality of indicator members refers to any number of indicator members greater than one. In various alternative embodiments, the advancement member 6600 includes a first end connected to a planar side portion or hub of the indicator wheel. The advancement member includes a curved resilient portion having a free end with the tooth portion 6604 formed on the end thereof. Indicia, preferably in the form of numbers, are applied to the circumferential surface 6560 of the skirt. Of course, the indicia can take any form as herein described, including color coding, text, etc. It should be understood that the advancement member, indicator wheel and ratchet gear can take any of the forms described herein.

Figure 126:
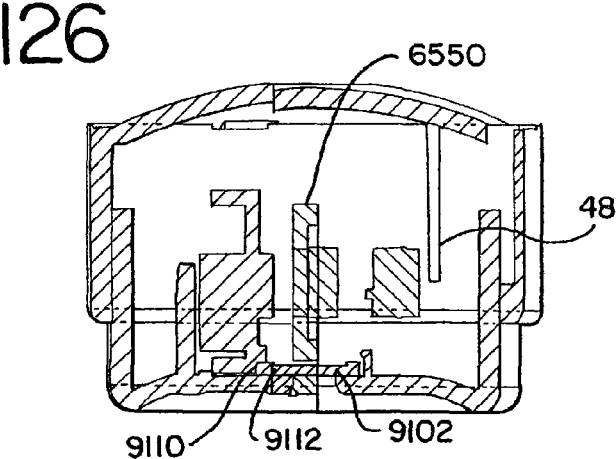
Figure 127:
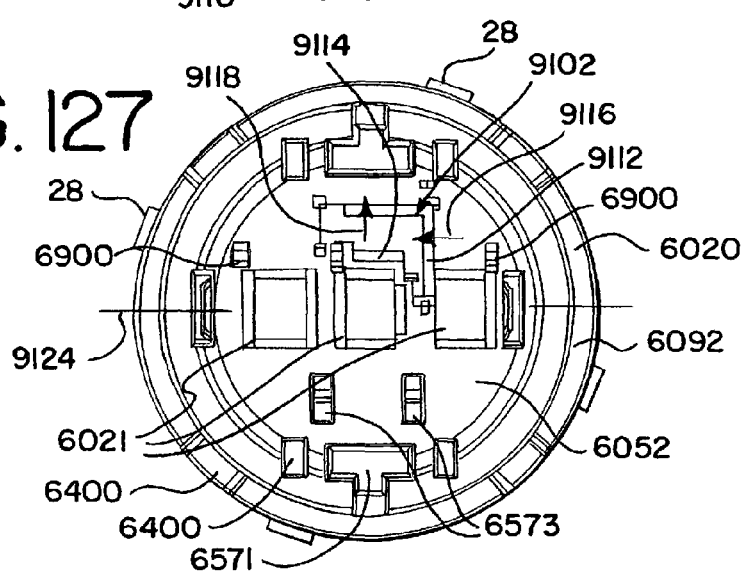

Referring to FIGS. 126, 141, and 142, an actuator member 48, otherwise referred to as a pawl or ratchet member, is configured as a resilient arm member that extends upwardly from the base member and terminates in an end portion shaped to selectively engage at least one of the teeth of the ratchet gear of the first indicator member. Referring to FIGS. 119, 120, 141, and 146 the cap member has at least a pair of engagement members 6573 formed integrally therewith and including ramped surfaces. A plurality of non-return members 6900 extend from the cap member and selectively engage the ratchet gears to ensure unidirectional rotation of the primary indicator members. Although the engagement members and non-return members are shown as being formed in the cap member, it should be understood that the primary indicator members could be mounted in the base member, with the engagement members and non-return members also formed therein, and with the actuator extending from the cap member.

In one embodiment, arm members serve as a combined engagement member and non-return member. In particular, the arm member functions as a non-return member and includes an end portion that is biased away from the teeth on the ratchet gear as the actuator member, or adjacent indicator member with its advancement member, is actuated to advance the ratchet gear. The arm member snaps back so that the end portion engages one of the teeth of the ratchet gear so as to ensure that the rotation of the ratchet gear is unidirectional. The arm member overlying the ratchet gears of the second and third indicator members also serves as an engagement member that selectively engages the advancement members connected to the indicator members.

In the embodiment of FIGS. 145 and 146, each indicator wheel 6550 includes a ratchet gear 6552 and an indexing gear 6551 disposed on opposite sides of the respective wheels. The indexing gear 6551 is engaged and indexed by the return member, otherwise referred to as the indexing member. In the embodiment of FIG. 145, a pair of advancing gears 6533 are rotatable mounted on an axle 6537 parallel to the axis of rotation of the indicator wheels. The gears 6533 are independently rotatable on the axle. The axle 6537 is supported by a pair of bearing supports 6539 extending from the cap member. The indicator wheels each include an advancement tooth 6535 that engages the advancement gear upon one rotation of the indicator wheel. The first advancement gear 6533 is meshed with the ratchet gear on the adjacent second indicator wheel. As the advancement gear 6533 is advanced by the advancement tooth 6535, the gear advances the adjacent indicator wheel an incremental amount. The advancement of the third indicator wheel is made by way of the second advancement gear being advanced by an advancement tooth of the second indicator wheel.

In the embodiments shown in FIGS. 122-123, 129, 145, and 146 the indicia are preferably formed around the circumferential surface 6560 of the indicator wheel in the form of numbers ranging from 0 to 9, with the ratchet gear on the indicator member having 10 teeth. In operation, it should be understood that the three, or more or less, indicator members can be preset to the maximum number of dosages contained within the container, with the indicia, or in this case numbers, arranged about the periphery of the indicator wheel, such that successive, sequential actuations of the container cause the indicator members to count down.

Alternatively, the indicator members are assembled such that the zero (0) of each indicator member is displayed in the viewing window to the user. The container is then actuated by the user such that the first indicator member rotates within the housing to sequentially display the number of doses that have been dispensed from 1 to 9. Upon the tenth actuation, the indicator member completes a single revolution, by virtue of the ten teeth preferably formed about the ratchet gear which correspond to the predetermined number of actuations, and causes the second indicator member to advance one number from 0 to 1 as the first indicator member again displays a 0 such that the two members together indicate that 10 dosages have been dispensed. The first indicator member is again rotated by successive actuations until another single rotation is completed to further rotate the second indicator to reveal the 2, so as to indicate that 20 dosages have been dispensed. Upon a complete rotation of the second indicator member, corresponding to 100 actuations, the third indicator member is advanced to reveal a 1 in the viewing window with the first and second indicator members revealing a 0, and so on.

Description of Operation of Various Embodiments of Primary Indicating Devices Mounted to Bottom of Container:

In operation, as shown in FIGS. 12-21, the user depresses the cap 220 member from a fully extended position (see FIG. 12) toward the base member such that the cap member bottoms out in the base member at the bottom of the stroke (FIG. 14) and such that the base member imparts an axial load on the container until a metered dosage is dispensed therefrom. In a preferred embodiment, the biasing force of the spring 100 (shown in FIG. 6), or alternative return mechanism such as the resilient arm members which act as springs, is less than the biasing force of the spring located in the metering valve of the container, such that the cap member first bottoms out in the base member with the container then being moved downwardly in the housing until a metered dose is dispensed.

Figure 12:
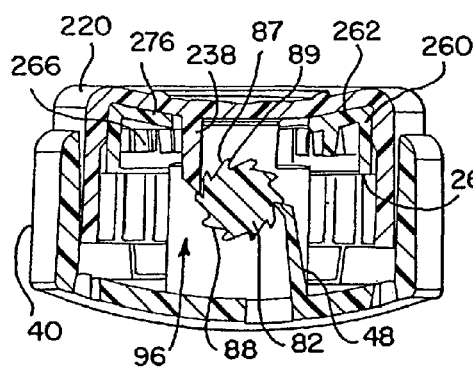
FIG. 12 is a cross-sectional view of the indicating device taken along line 12-12 of FIG. 11, wherein the cap member is in a fully extended position relative to the base member prior to the application of an axial force by the user.
Figure 13:
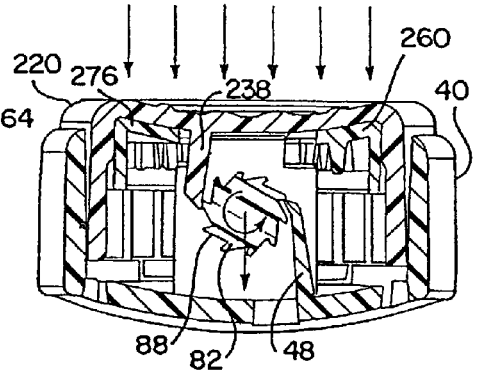
FIG. 13 is a cross-sectional view of the indicating device similar to FIG. 12 but with the cap member shown as moving toward the base member at an intermediate position of the stroke as indicated by the directional arrows.
Figure 14:
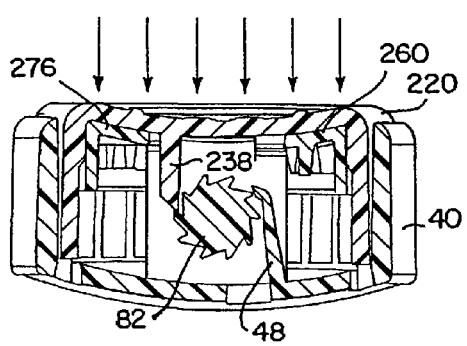
FIG. 14 is a cross-sectional view of the indicating device similar to FIG. 12 but with the cap member reaching the bottom of the stroke as indicated by the directional arrows.
Figure 15:
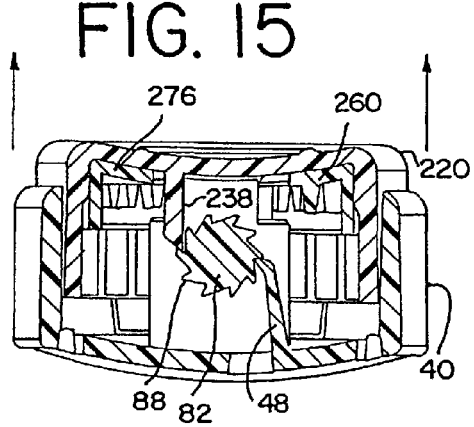
FIG. 15 is a cross-sectional view of the indicating device similar to FIG. 12 showing the cap member as it returns to the fully extended position relative to said base member as indicated by the directional arrows.

Referring to FIGS. 12, 13 and 14, as the cap member 220 is depressed toward the base member 40, the pawl 48 selectively engages the engagement surface 89 of one of the ratchet wheel teeth and rotates the ratchet wheel. The tapered surface 87 of one of the teeth formed on the ratchet wheel simultaneously biases the non-return member 238 outwardly until it selectively engages the next tooth near the bottom of the stroke. The return member provides an audible click as it engages the next tooth. The user then releases the cap member whereinafter the spring 100 (shown in FIG. 6), or similar return mechanism, biases the cap member 220 away from the base member 40 until the engagement member engages the base portion at the top of the stroke as shown in FIG. 15. When the cap member is released by the user, the container is biased upwardly within the housing along the longitudinal axis such that the valve stem is moved to the closed position within the container. Simultaneously, as the cap member is released and allowed to move away from the base member, the pawl 48 is biased outwardly by the tapered surface 87 of one of the teeth on the ratchet wheel as the non-return member 238 prevents a backwards rotation thereof so as to maintain a unidirectional rotation of the ratchet wheel. At the top of the stroke (shown in FIG. 15), the pawl 48 is again placed in position for selective engagement with one of the teeth of the ratchet wheel. Again, the pawl provides an audible click as it engages the next tooth. In summary, on the down stroke the non-return member makes a clicking sound as it slides over one or more ratchet teeth, while on the up stroke, the pawl member also makes a clicking sound as it slides over one or more ratchet teeth. In this way, the ratchet wheel 82, and connected drive member 86 (shown in FIGS. 18-21), are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel will make one full revolution for every ten actuations of the indicator device and container, or a tenth of a revolution for each actuation. One skilled in the art will appreciate that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl is biased outwardly by the tapered surface of one of the ratchet wheel teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

As shown in FIGS. 18-20, 38 and 44 the drive member 86 is shown as preferably having a single tooth 81 or segment. Therefore, upon every tenth actuation, the drive member 86 is rotated such that the tooth selectively engages one of the teeth 266 formed on the indicator member so as to rotate the indicator member an incremental amount. The incremental amount of rotation is defined by the distance between adjacent teeth, otherwise defined as the circular pitch of the teeth. In this way, the drive member is selectively engaged with at least one of the teeth of the indicator member after and upon a predetermined number of axial movements of the cap member relative to the base member so as to rotate the indicator member the incremental amount. The predetermined of number axial movements required to cause the indicator member to rotate is defined by and dependent upon the reduction ratio of the ratchet wheel and drive member, which, in turn, is defined by dividing the number of teeth formed on the ratchet wheel by the number of teeth formed on the drive member. For example, as shown in the preferred embodiment, a ratchet wheel having ten teeth and a drive member having one tooth will result in an incremental movement of the indicator member, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

Figure 19:
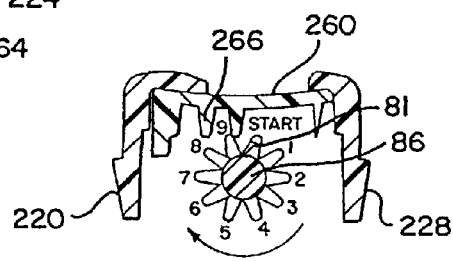
FIG. 19 is a cross-sectional view taken along line 19-19 of FIG. 18.
Figure 21:
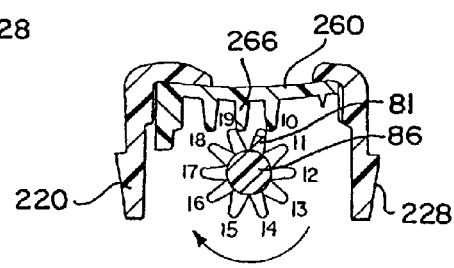
FIG. 21 is a cross-sectional view taken along line 21-21 of FIG. 20.
Figure 22:
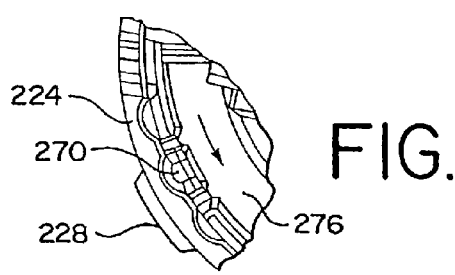
FIG. 22 is an enlarged partial bottom view of the cap member and indicator member showing the indicator member having an indexing member engaging an indentation formed on the cap member.
Figure 23:
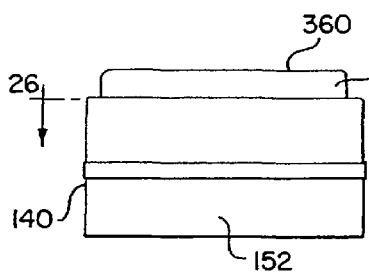
FIG. 23 is a side view of an alternative embodiment of the indicating device.

Referring to FIG. 19, the indicator member 260 and drive member 86 are shown prior to an initial actuation or use by the user. In particular, the drive member tooth is positioned adjacent the first tooth 266 on the indicator member. In this embodiment, wherein the ratchet wheel comprises ten teeth, ten actuations are required before the tooth 81 engages the first tooth 266 on the indicator member as shown in FIG. 21. At this point, the indicator has completed a single cycle equal to the number of predetermined number of axial movements, which results or culminates in the incremental movement of the indicator member. The cycle is then repeated (by again making the predetermined number of axial movements) so as to again culminate in the incremental movement of the indicator member. Preferably, as shown in FIGS. 1A, 3A, 24 and 26, numerical indicia (including numbers and dots) are applied in increments of ten to correlate to the preferred embodiment requiring ten axial movements for one incremental advancement of the indicator wheel.

The ratchet wheel and drive member with their reduction ratio provide a simple but reliable mechanism for advancing the indicator member. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member. As such, the indicator member can be made with coarser teeth at less cost. In addition, larger coarser teeth interacting with a relatively large drive member tooth helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses). This single revolution corresponds to a usage cycle, which is defined as the movement of the dosage indicator from an initial reading, which indicates that the container is full, to a final reading, which indicates that the container should be replaced. Of course, the indicator member, if initially set to a smaller number of dosages, may make less than a complete revolution in completing a usage cycle.

In the alternative embodiments shown in FIGS. 38 and 44, the viewing window 1034, 2034 is large enough such that the first and second dosage indicator members 1060, 2060, 1800 with their indicia are visible therein. In the operation of these embodiments, the indicator member 1800 rotates with each actuation of the cap member 1020, 2020 relative to the base member 1040, 2040 as the ratchet wheel 82 is driven by the pawl member. The indicator member 1800 rotates about an axis substantially perpendicular to the axial movement of the cap member relative to the base member and to the rotational axis of the indicator member 1060, 2060. In the preferred embodiment, with the indicator member 1800 having "ones" indicia and the ratchet wheel 82 having ten teeth, the indicator member 1800 is advanced upon each actuation and provides indicia visible to the user to notify them of such advancement. As the indicator member 1800 completes a cycle, or rotation, the indicator member 1060, 2060 is advanced one increment by the drive member 86 and the indicator member 1800 begins another cycle. In this way, the user is advised as to each actuation of the indicating device and the attendant dispensement of a dosage from the attached container.

Figure 58:
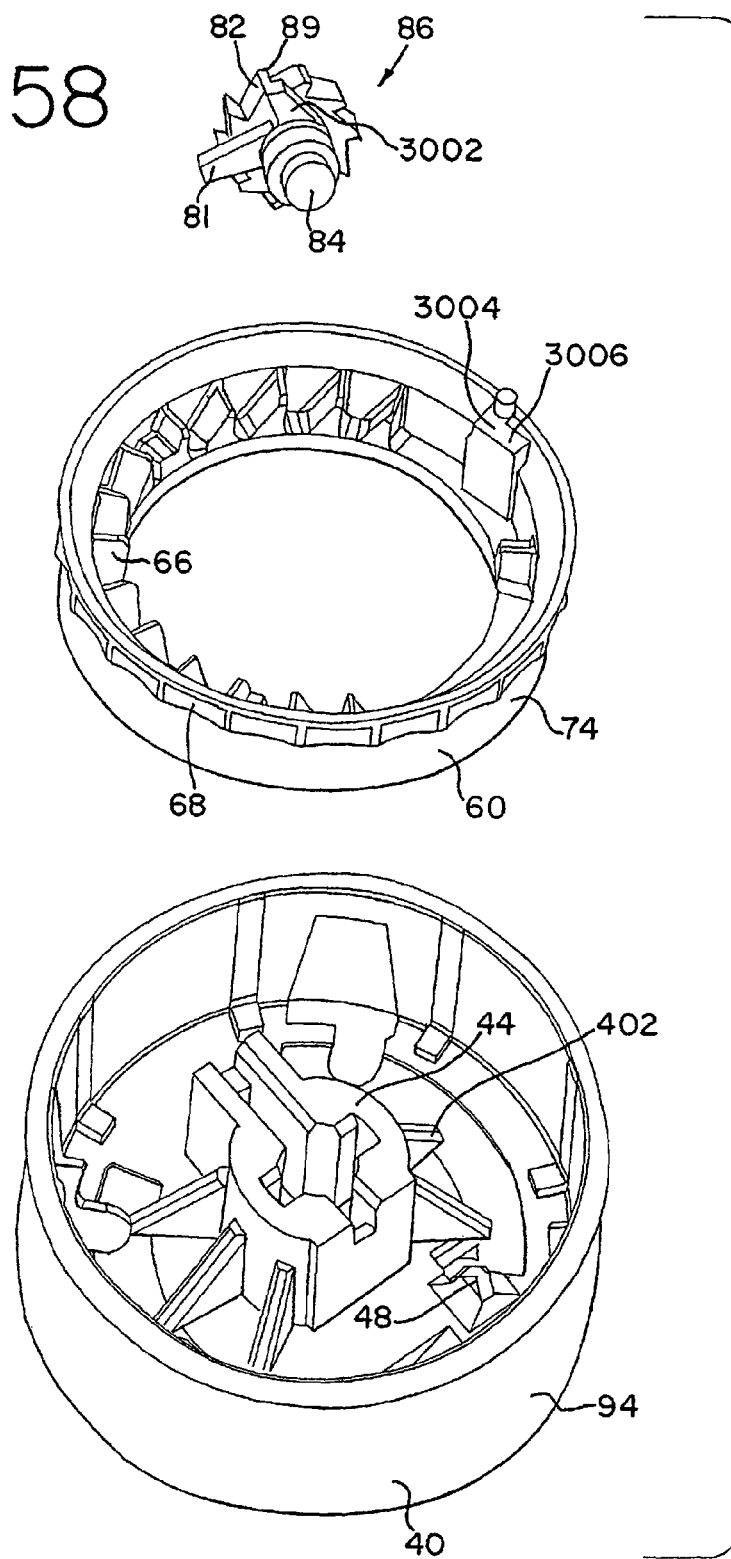
FIG. 58 is a bottom exploded perspective view of one preferred embodiment of the base member, indicator member, drive member and ratchet wheel.
Figure 59:
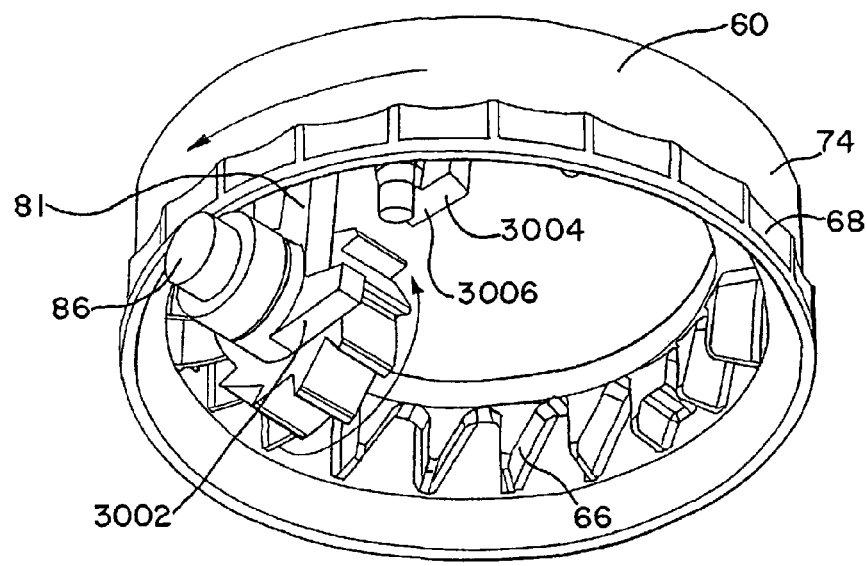
FIG. 59 is a bottom perspective assembly view of one preferred embodiment of the indicator member, drive member and ratchet wheel during the completion of a final predetermined actuation.
Figure 60:
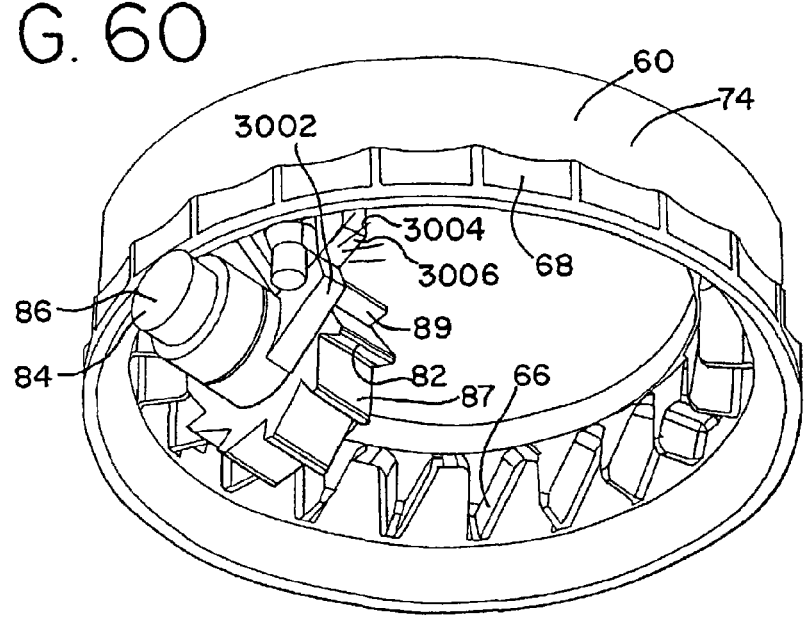
FIG. 60 is a bottom perspective assembly view of the embodiment of the indicator member, drive member and ratchet wheel shown in FIG. 59 following the completion of the final predetermined actuation.

Where, as shown in FIGS. 5, 40 and 58, the teeth 66, 266, 1066 extend only partially around the periphery of the indicator member, the indicator member 60, 260, 1060 is not advanced after the drive member engages the last tooth, even when the cap member is repeatedly moved to actuate the container. This ensures that the indicator member cannot be advanced past the last indicia indicating that the container is empty, or should otherwise be replaced, to a first indicia indicating that the container is full, so as to confuse the user.

In one preferred alternative embodiment, shown in FIGS. 58-67, the drive member has an additional finger 3002, or stop member circumferentially spaced from the single tooth 81. For purposes of simplicity and clarity, various feature and components previously described are referenced in the Figures with the same reference numbers. The stop member 3002 has a lesser radial length than the tooth 81 such that it clears the teeth 66 formed on the indicator member 60 as the drive member is rotated by actuations of the container, and as it is engaged with the indicator member after and upon the predetermined number of movements of the cap member relative to the base member.

As best shown in FIGS. 58-60, 65 and 66, the indicator member has a corresponding stop member 3004 spaced circumferentially from the last tooth 66. The stop member preferably extends downwardly from the upper surface a greater extent and is longer than the teeth 66. Preferably, the stop member 3004 has a stop surface 3006 formed at an angle of about 15 degrees from the horizontal, such that it slopes up and away from the drive member stop member 3002. Preferably, the angle is greater than 0 degrees from the horizontal such that the stop member 3002 on the drive member cannot slip past the stop surface 3006 and thereby allow subsequent rotations of the ratchet wheel 82.

Referring to FIGS. 61-67, in operation of the preferred embodiment of FIGS. 58-67, the user moves the cap member 20 toward the base member 40 a first predetermined number of times corresponding to the total number of metered dosages, such that the indicator member 60 is rotated between an initial position, wherein indicia indicate to the user that the container is full, and a final position, wherein the indicia indicate to the user that the container should be replaced. During the first predetermined number of actuations, the drive member, and in particular, the tooth 81, is successively engaged with at least one of the teeth 66 of the indicator member upon a second predetermined number of axial movements of the cap member 20 relative to the base member 40, wherein the indicator member is moved an incremental amount. Preferably, the first predetermined number of actuations is greater than and some multiple of the second predetermined number of actuations. However, it should be understood that the first and second predetermined number of actuations can be equal, preferably with the second predetermined number being greater than one.

Figure 65:
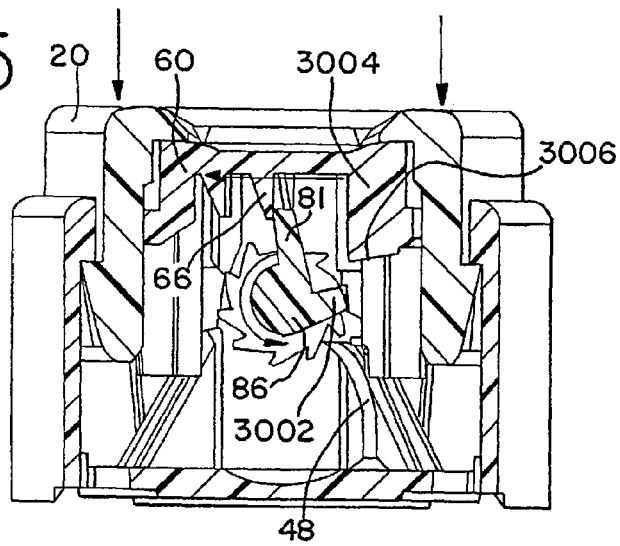
FIG. 65 is a cross-sectional view of the indicating device showing the drive member engaging the indicator member as the cap member is moved toward the base member during the final predetermined actuation of the container as indicated by the directional arrows.
Figure 66:
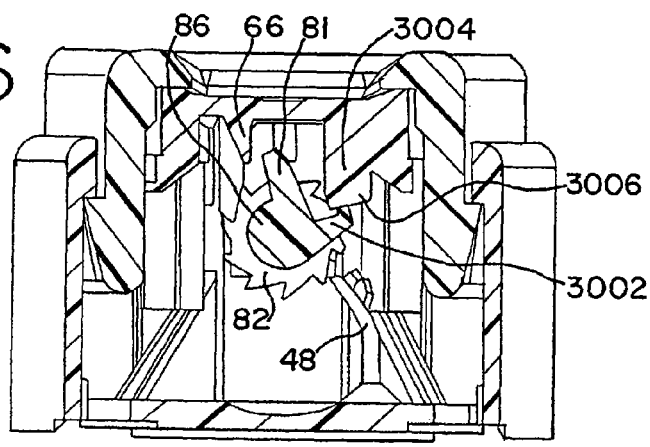
FIG. 66 is a cross-sectional view of the indicating device similar to FIG. 65, but with the cap member shown as it returns to the fully extended position relative to the base after the final predetermined actuation of the container.
Figure 67:
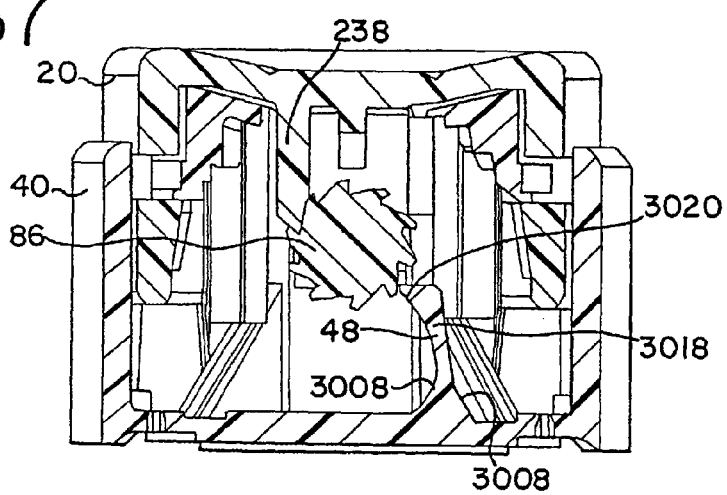
FIG. 67 is a cross-sectional view of the indicating device, wherein the cap member is in a fully extended position relative to the base member immediately after the application of a final predetermined actuation of the container by the user.

Referring to FIGS. 65 and 66, as the cap member 20 is moved toward the base member 40 on the final predetermined actuation of the container 12, the drive tooth 81 moves indicator member 60 a final incremental amount as the pawl 48 engages one of the teeth 89 and moves the ratchet wheel 82, and thereby rotates the stop member 3004 formed on the indicator member into vertical alignment over and with the stop member 3002 formed on the drive member. Accordingly, the stop members 3002, 3004 must be dimensioned and located on the drive member and indicator member respectively and relative to the other teeth on the drive member and indicator member so as to allow the stop member 3004 to pass over the stop member 3002 during the final actuation. In this location, with the stop members 3002, 3004 engaged, the drive member 86, and connected ratchet wheel 82, can no longer be rotated relative to the cap member 20 upon subsequent actuations.

Figure 61:
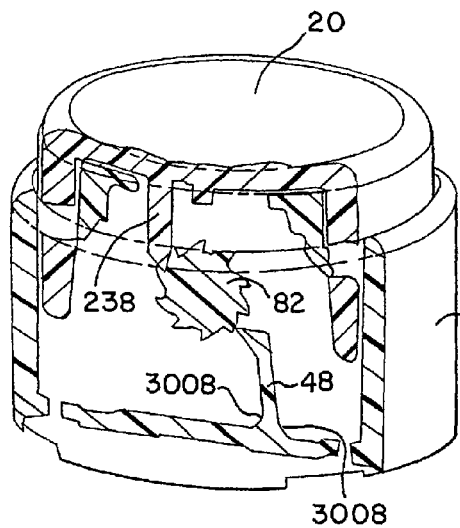
FIG. 61 is a cross-sectional view of the indicating device, wherein the cap member is in a fully extended position relative to the base member immediately after the application of a final predetermined actuation of the container by the user.
Figure 62:
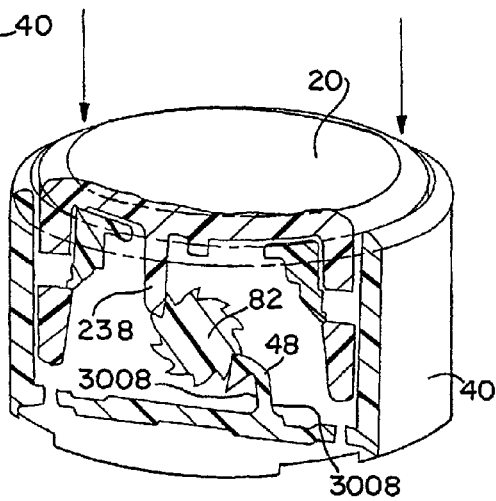
FIG. 62 is a cross-sectional view of the indicating device similar to FIG. 61, but with the cap member shown as moving toward the base member in an intermediate position of the next downward stroke of the cap member after the final predetermined actuation of the container as indicated by the directional arrows.

As best shown in FIGS. 61 and 62, upon the next subsequent actuation of the container 12 after the final predetermined actuation, the cap member 20 is again moved toward the base member 40. However, since the drive member is locked and unable to rotate, the engagement surface 89 of one of the teeth on the ratchet wheel engages the pawl 48 and deforms the pawl, preferably by bending, as the cap member 20 moves toward the base member 40. As such, neither the non-return member 238 nor the pawl 48 moves past any teeth of the ratchet wheel 82 and the audible click is thereby eliminated. In this way, an auxiliary warning system, or indicia, is provided to inform the user that the final predetermined dose of medication has been dispensed, and/or that the container should be replaced. At the same time, however, the container can still be actuated, such that if certain residual doses were available therein they can be dispensed in an emergency situation.

Figure 63:
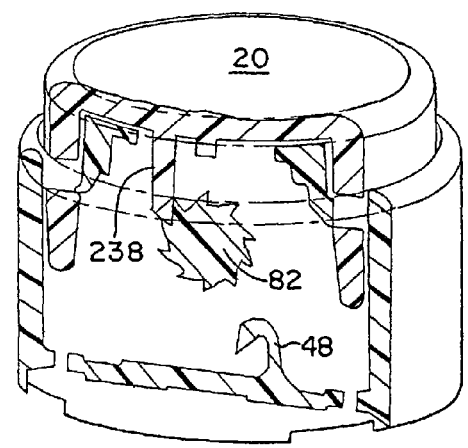
FIG. 63 is a cross-sectional view of the indicating device similar to FIG. 61, but with the cap member shown as it returns to the fully extended position relative to the base on subsequent strokes of the cap member after the final predetermined actuation of the container.
Figure 64:
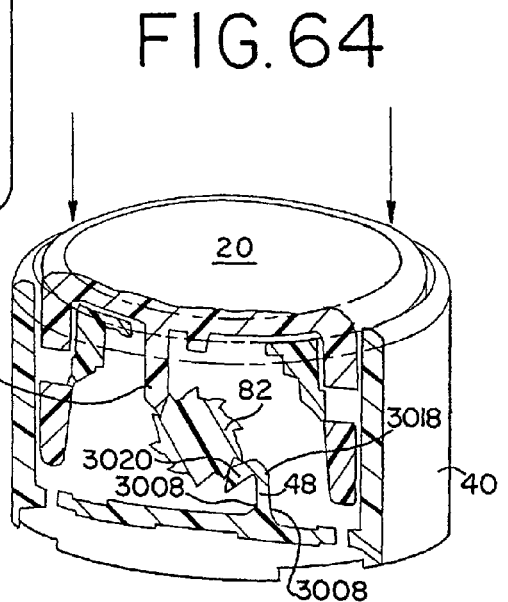
FIG. 64 is a cross-sectional view of the indicating device similar to FIG. 61, but with the cap member shown as moving toward the base member in an intermediate position during subsequent strokes of the cap member after the final predetermined actuation of the container as indicated by the directional arrows.

Referring to FIGS. 63 and 64, preferably, the pawl 48 is configured to bend over after the final predetermined actuation such that it does not provide a false audible indication that the container does not need to be replaced, e.g., that additional doses are available upon subsequent actuations after the next subsequent actuation following the final predetermined actuation. In addition, the bent pawl 48 prevents tampering and unintended resetting by the user.

In particular, the pawl 48 has fillets 3008 formed along its base each having a preferred radius of about 1.40 mm, or preferably a radius greater than a minimum value required to prevent stress concentrations in the plastic during the bending process that occurs during the next subsequent actuation or movement of the cap member after the final predetermined actuation of the container. The overall height of the pawl is preferably about 5.20 mm. The width of a pawl head 3020 is preferably about 1.80 mm, and the width of a stem 3018 is preferably about 0.65 mm. The overall height of the pawl 48 and the width or thickness (or diameter if round) of the stem 3018 are preferably greater than minimum permissible values that will provide the pawl with enough strength and resistance to buckling during normal operation, but which allows the pawl to bend during the next subsequent actuation of the container and movement of the cap member after the final predetermined actuation of the container. The width of the head 3020 of the pawl allows it to function during the normal operation of the device, and further allows it to be nested with the ratchet wheel 82 after the pawl is bent when the cap member 20 and ratchet wheel 82 are at the bottom of subsequent strokes after the final predetermined actuation. Obviously, the various preferred dimensions described herein can be scaled up or down depending on the size of the overall indicator and force required to actuate the container, and the corresponding force of the return springs.

In alternative preferred embodiments, shown in FIGS. 33-36, 68 and 69, the indicating device includes a lock device. In particular, in one preferred embodiment, the base member includes a first lock member 702, configured as a post member extending upwardly from the bottom of the base member. The indicator member 760 includes a second lock member 704, shown in FIG. 35 as a radial extension of one of the plurality of teeth 776 formed around the circumference of the indicator member, and shown in FIG. 69 as a separate post member. In operation, the cap member is moved towards and away from the base member between a fully extended position, wherein the cap member is distal to the base member, and a bottom of the stroke position, wherein the cap member is proximate the base member, so as to rotate the indicator member as described above. During this operation, as shown in FIGS. 33 and 34, the first lock member 702 is positioned inside the inner diametrical surface of the plurality of teeth so as to not interfere therewith as it is moved into the recess formed by the indicator member as shown in FIG. 33. After the indicator member has made one complete rotation, which preferably correlates to an emptying of the container, the second lock member 704 is rotated over the first lock member 702 as shown in FIGS. 35, 36 and 69. In this position, the cap member cannot be moved toward the base member. In particular, during the final downstroke of the cap member, one or both of the first and second lock members 702, 704 are biased against the other such that they snap into position, one over the other, upon completion of the final upstroke.

The immobility of the cap member provides visual and physical secondary indicia that the container should be replaced, and further prevents the mechanism from clicking or the indicator member from moving, thereby providing both a visual as well as an audible indication that the container should be replaced. One of skill in the art should understand that the size and shape of the first and second lock members can be varied. For example, a post member may extend from the cap member so as to engage a stepped surface in the base member, which functions as a stop member.

In addition, it should be understood that, in one alternative preferred embodiment, the pawl 48 can be made sufficiently robust, for example by thickening the stem, such that when it is used with the stop members 3002, 3004, the pawl 48 engages the ratchet wheel 82 and prevents the cap member 20 from being moved toward the base member 40, rather than bending or buckling as described above with respect to another preferred embodiment. As such, the immobility of the cap member 20 relative to the base member 40, and the elimination of any clicking sound, provides further indicia to the user that the container should be replaced. It should also be understood that the lock member can extend from the cap member and engage a corresponding lock member on the base member.

Figure 68:
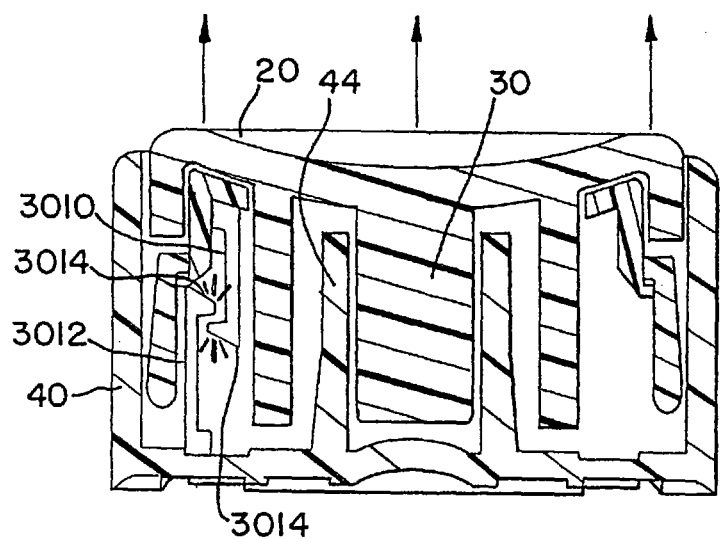
FIG. 68 is a cross-sectional view of one preferred embodiment of an indicating device with first and second lock members engaged after the final predetermined actuation of the container.

Referring to FIG. 68, an alternative preferred embodiment of the lock device is shown. In particular, the lock device includes a pair of catch members 3010, 3012 formed on the indicator member 60 and the base member 40 respectively. Alternatively, one of the catch members can extend from the cap member and engage a catch member formed on the base member. In the preferred embodiment, each catch member 3010, 3012 includes an end portion 3014, 3016 having opposing hooks, which engage at the bottom of the final predetermined stroke of the cap member 20 relative to the base member 40. In this position, the cap member 20 cannot be moved away from the base member 40. The immobility of the cap member provides a secondary indicia that the container should be replaced, and further prevents the mechanism from clicking or the indicator member from moving, thereby providing both a visual as well as an audible indication that the container should be replaced. One of skill in the art should understand that the size and shape of the first and second catch members can be varied. In addition, the catch members can be configured as any two members that engage, for example by using adhesives, hook and loop type fasteners, detents, etc.

Figure 29:
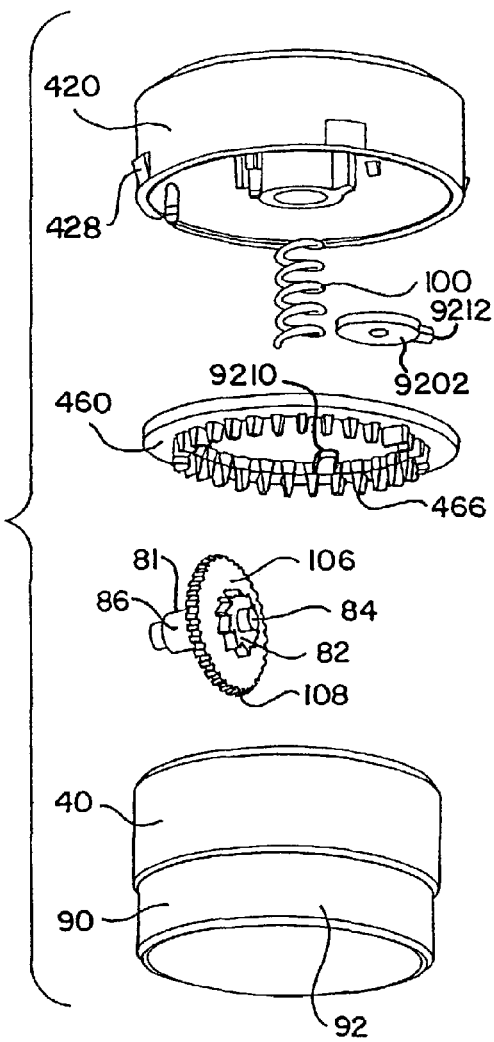
FIG. 29 is an exploded view of an alternative embodiment of the indicating device with an alternative embodiment of the reset device and an adapter.
Figure 30:
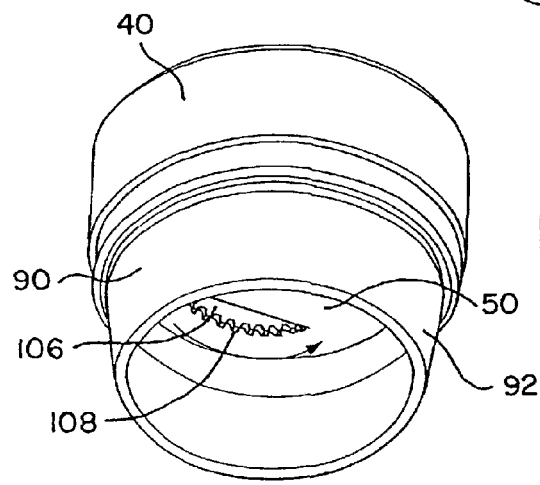
FIG. 30 is a bottom perspective view of the indicating device and adapter shown in FIG. 29.

As shown in FIGS. 29 and 30, a reset wheel 106 is coaxially mounted with the ratchet wheel 82 and drive member 86. The outer periphery 108 of the wheel, which includes a plurality of teeth for gripping by the user's thumb, is exposed as it extends through the bottom surface 50 of the base member. One of skill in the art should understand that the reset wheel can be exposed by extending from other portions of the indicator device for access by the user. The user rotates the reset wheel 106 to manually rotate the indicator member to its original starting position, or any other desired setting, without having to move the cap member relative to the base member. In this way, the indicator member can be recycled for use on a new container, or can be moved to the proper setting prior to installing the indicating device on the container. In this way, the same indicating device can be used with various containers containing varying numbers of metered dosages of medicament. During the movement of the indicator wheel relative to the cap member, the force of the indexing member against the indentations in one of the cap member and indicator member is overcome such that the indexing member repeatedly moves into and out of engagement with the indentations as the indicator member is rotated by the user to the desired setting. This movement is similar to the movement of the indexing member occurring upon each incremental advancement of the indicator member relative to the cap member.

Preferably, the reset wheel of FIGS. 29 and 30 is used with an indicator member having teeth formed about its entire periphery, such that the indicator wheel need only be moved a few teeth (one or more) to return it to the zero (or full, e.g., 200) position. The reset wheel can be used with or without the lock device described above, since the wheel can be used to move or rotate the indicator wheel independent of any axial movement between the cap member and base member.

Figure 28:
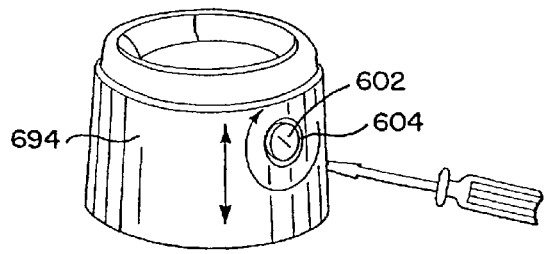
FIG. 28 is a perspective view of an indicating device with an alternative embodiment of the reset device.

In an alternative embodiment shown in FIG. 28, a reset selector member 602 is mounted to the end of the axle and is exposed in an opening 604 in the side or skirt 694 of the base member. The reset selector member 602 is mounted on the axle. The selector member 602 is provided with a slot adapted to receive the head of a screw driver or like tool, which can be actuated by the user to rotate the axle, coaxially mounted drive member and indicator member until the desired indicia are visible in the viewing window. This feature can be valuable for resetting an indicating device for use on a new container, or for initially setting the device for the proper number of doses contained in the container. One of skill in the art should understand that recesses and/or protrusions other than the disclosed slot can be exposed on the selector member to allow the user to grip or otherwise operably engage the selector member and to thereafter rotate the indicator member. One of skill in the art should also understand that the opening in the base member could be positioned anywhere along the longitudinal path of the axle as the cap member moves relative to the base member so as to expose the selector member when aligned with the opening.

Figure 27:
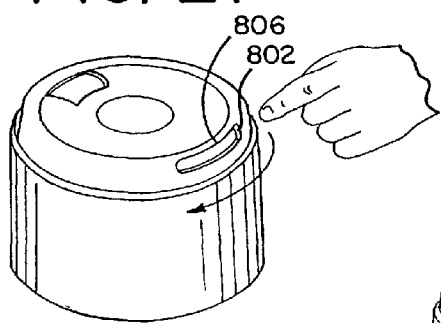
FIG. 27 is a perspective view of an indicating device with a reset device.

In yet another alternative embodiment, shown in FIG. 27, a selector window 806 is formed in the top of the cap member. A reset selector member 802, configured as a protrusion or like grippable member, is exposed in the window as the indicator member is rotated to the empty position. In one embodiment, as described above, the plurality of teeth are formed only around a portion of the periphery of the indicator member so as to leave a gap between the first and last tooth. In such an embodiment, the selector window 806 is preferably of such length that the user can move the reset selector member 802 within the window until the first tooth is again in position for engagement with the drive member. It should be understood, however, that the reset selector member can also be used with an indicator member having teeth formed around the entire periphery of the member.

In an alternative embodiment, a plurality of reset members, or a similar grippable surface, configured for example as a plurality of notches or teeth, can be formed around the entire periphery of the indicator member and exposed in a selector window, or alternatively, in the viewing window. In such an embodiment, the indicator wheel can be rotated to expose different indicia at any time simply by engaging the reset selector members on the indicator member with the user's thumb or like member.

In yet another embodiment, shown in FIG. 24, an opening, or selector window 906, is provided in the top of the cap member. A thin tool, such as a paper clip, is inserted through the opening to bias the resilient indexing member 370 out of engagement with the indicator member. The user can then operably engage the indicator member with their finger or the like, either through the viewing window or a selector window, to move the indicator member to the desired setting.

Figure 43:
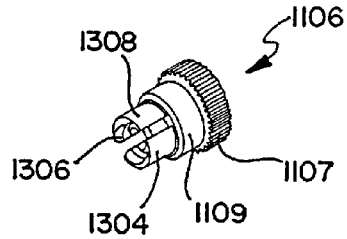
FIG. 43 is a perspective view of the reset member shown in the indicating device shown in FIG. 38.

In yet another alternative embodiment, shown in FIG. 43, the reset member, with the collar 1109 disposed on the axle 1084 of the drive assembly, is pulled axially outward with respect thereto from a disengaged position, where the engagement portions 1306 of the flexible fingers 1304 are positioned circumferentially around the axle 84, to an engaged reset position, such that the engagement portions 1306 of the flexible fingers are biased outwardly as they ride up the ramp 1083 and are thereafter moved into engagement with the teeth 1085 formed around the axle of the drive assembly. The user then rotates the reset member 1106 about a rotation axis, which is substantially perpendicular to the axial movement of the cap member relative to the base member. As the reset member is rotated, the protrusion 1308 on the flexible fingers is brought into engagement with the protrusion 1310 on the indicator member 1060 so as to rotate the indicator member an incremental amount and thereby bring the first tooth on the other side of the gap 1061 into position for engagement by the drive member, thus bridging the gap 1061 between the teeth of the indicator member. As the reset member 1106 is further rotated, the drive member tooth 89 engages the teeth 1066 of the indicator member, and the reset member can be rotated to manually drive the indicator member, or indicator members, to the desired preset condition. For example, the indicator members can be reset to indicate 200 dosages for use with a container having 200 dosages.

In a preferred embodiment, the engagement portions 1306 and/or teeth 1085 formed on the axle of the drive assembly are configured to allow rotation of the drive member in only one direction. Therefore, rotation of the reset wheel in an opposite direction will not effect a rotation of the drive member in that same direction as the flexible fingers, with their engagement portions, will simply slide over the teeth formed about the axle. This one-way rotation prevents the drive member from engaging and rotating the indicator member in an opposite direction, which direction is opposed both by the non-return member engaging the ratchet wheel, and the one-way indexing interface between the cap member and indicator member.

To install the reset member and drive assembly, the drive assembly is installed in a vertical manner such that the axle 84 is received in the flexible snap enclosure 1036. Once the drive assembly is snapped in place, the reset member 1106 is inserted through the opening in the cap member and over the axle 1084 until the fingers eventually are disposed around the axle 84 in the disengaged position. In this way, the reset member, which is supported by the bearing surface 1300 of the cap member, further supports the drive assembly.

In yet another embodiment, best shown in FIGS. 52-55, the indicator member 2060 has a plurality of teeth extending around the entire circumference thereof. At least one of the teeth 2067 has a cut-away portion 2069 aligned with the tooth 89 of the drive member. Accordingly, at the end of a cycle, the drive member is positioned in a disengaged position where even repetitive actuations of the indicating device do not lead to the advancement of the indicator member as the drive member, with its one or more teeth 89, merely passes through the cut-away portion 2069 of the tooth, with which it is aligned. In this embodiment, however, the drive member 86 is axially moveable with respect to the indicator member 1800 and ratchet wheel 82.

As best shown in FIGS. 44, 47 and 52-56, a reset member 2106 includes a grippable wheel 2107 connected to a drive shaft 2109. As shown in the preferred embodiment of FIG. 47, the end of the drive shaft includes a plurality of teeth 2306, that engage slots 2308 or openings dimensioned to receive the teeth formed in one end of the drive member 86. The drive member is installed on the shaft of the reset wheel such that the teeth 2306 formed on the end thereof engage the slots 2308 formed in the drive member. The drive member is then inserted into the groove 1801 of the collar 1082 extending from the indicator member.

In operation, the user pulls the reset member 1206 axially outward so as to move axially the drive member 86 from a disengaged position, where the drive member tooth 89, or teeth, is aligned with the cut-away portion 2069 of the tooth on the indicator member, to an engaged or reset position, where the drive member tooth is brought into engagement with the portion 2067 of the tooth that is not cut-away. In the reset position, the user rotates the reset wheel 2107 and connected drive member 86 so as to advance the indicator member 2060, or indicator members, to the desired setting independent of the axial movement of the cap member relative to the base member. In the disengaged position, the reset wheel is recessed between a pair of tapered flanges formed around the circumference of the base member.

As shown in FIGS. 44 and 52-56, the indicator member 2060 includes a cover portion 2087 that extends radially inward from the top portion of the indicator member. The cover portion is brought into alignment with the viewing window at the end of the usage cycle such that the indicator 1800, which can continue to be spun beneath the cover portion is not visible. Indicia, such as the number "0" or the words "end" or "empty" can be applied to the cover portion to inform the user that the container is empty, or should otherwise be replaced.

As shown in FIGS. 37-43, the indicating device also includes a usage indicator member 1500. The indicator member 1500 is configured as a ring and is disposed around the skirt 1074 of the dosage indicator member 1060 where it is trapped between the rim flange 1078 of the indicator member and the bottom surface of the top of the cap member. In this way, the usage indicator member 1500 is supported by and is moveable about the dosage indicator member 1060. The indicator member 1060 also is thereby rotatably mounted about an axis substantially parallel to the axial movement of the cap member relative to the base member. The indicator member 1500, which is configured as a ring, has a plurality of teeth 1502 formed around the outwardly facing radial periphery thereof. As the indicator member 1500 is advanced as explained above, a flexible finger 1273 formed along the circumferential rim 1078 of the indicator member 1060 is biased radially inward by a ramp 1277 formed on the inside of the cap member so as to engage at least one of the plurality of teeth 1502 formed on the indicator member and thereby advance the indicator member an incremental amount, defined by the distance between adjacent teeth. The number of teeth formed around the indicator member corresponds to the number of intended usage cycles of the indicating device.

In the preferred embodiment, which has only a single ramp 1277, the usage indicator member 1500 is advanced one tooth upon each complete rotation of the dosage indicator member 1060, which corresponds to one complete usage cycle for the indicating device. For example, the indicating device can be initially set to reveal an initial count of 200 dosages. As the indicating device is successively actuated to dispense the dosages, the indicator members 1060, 1800, with indicia, are actuated to count down until they reveal a final count of 0 dosages available for use. At that time, the drive assembly is positioned in the disengaged position, as explained above.

As the reset member 1106 is used to actuate the drive assembly to reset the device for another usage cycle, the indicator member 1060 with its resilient finger 1273 is biased into engagement by the ramp 1277 such that the usage indicator member is rotated. In this way, the usage indicator member 1500 is rotated, or advanced, upon the completion of each successive usage cycle. The number of teeth 1502 on the indicator member 1500 corresponds to the number of intended uses for the indicator. For example, in the embodiment shown in FIGS. 38 and 41, the indicator member 1500 has twelve teeth corresponding to an intended twelve uses of the indicating device with twelve different containers. As noted above, the reset member can be used to reset the indicia at any desired reading, such that one indicating device can be used with successive containers having different numbers of dosages contained therein. The indicator member 1500 also includes a stop member 1506 formed as a protrusion that extends radially inward from the top of the indicator member. The stop member 1506 engages a stop member extending downwardly from the top portion of the cap member upon completion of the final usage cycle. This engagement prevents the user from attempting to advance the dosage indicator member 1060 by way of the reset member and drive assembly, because the finger 1273 is biased into engagement with at least one of the teeth on the usage indicator member, which is immobilized. In this way, the entire device is immobilized. It should be understood that although the preferred embodiment is configured for twelve usage cycles, the usage indicator member could be provided with more or less teeth corresponding to more or less total available usage cycles.

Figure 41:
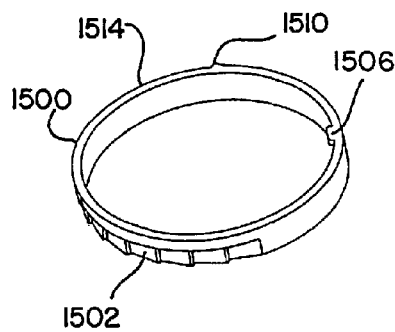
FIG. 41 is a top perspective view of a usage indicator member shown in FIG. 38.

Referring to FIG. 41, the usage indicator member 1500 further includes an indexing member 1510 configured as a protrusion extending radially outward from the outer circumferential surface of the indicator member. The indexing member 1510 selectively engages a plurality of teeth 1512 formed around the inner circumferential surface of the skirt of the cap member. The indexing member 1510 and teeth 1512 are configured as a ratchet to allow one-way rotation of the indicator member 1500 relative to the cap member 1020. In a preferred embodiment, the indexing member and teeth are tapered to interact and provide for the one-way action.

Figure 37:
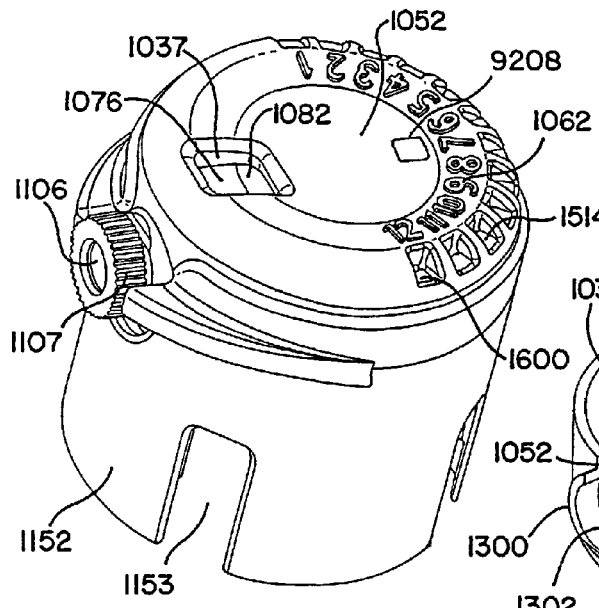
FIG. 37 is a perspective view of an alternative embodiment of an indicating device having at least one indicator member with dosage indicia and an indicator member with usage indicia.

As shown in FIGS. 37 and 38, a plurality of viewing windows 1600 are arranged around the outer periphery of the top of the cap member. A plurality of indicia 1602, shown as successive numbers, are affixed to the top of the cap member adjacent the viewing windows. The upper edge 1514 of the usage indicator member is provided with indicia that is visible through the viewing windows 1600, such that the user can ascertain which usage cycle the indicating device is currently functioning in. For example, in the embodiment shown in FIGS. 37 and 38, twelve viewing windows 1600 are provided with the numbers 1 to 12 arranged adjacent thereto, which correspond to the 12 usage cycles defining the life of the indicating device. The numbers, or other indicia such as various colors, can be applied to the cap member by printing, molding or any other of the techniques described above. Alternatively, a single viewing window can be provided to expose the indicator member, whereupon indicia can be applied to the top surface or upper edge 1514 thereof, or, if the window is provided in the side of the cap member, along the outer circumferential surface thereof.

In the embodiment shown in FIGS. 44-45 and 49-51, the usage indicator member 2500 includes a hub 2520 having an opening 2521 that is rotatably mounted on a post 2522 extending downwardly from the inner surface of the top portion of the cap member 2020. In this way, the usage indicator member 2500 is rotatably mounted to the cap member 2020 about an axis substantially parallel to and spaced from the rotational axis of the dosage indicator member 2060. The axis of rotation for the dosage usage indicator member is also substantially parallel to the axial movement of the cap member relative to the base member.

The indicator member 2500 includes a ring 2524 formed about the hub 2520 which is connected thereto with a rib 2526 and a bottom surface 2528. The indicator member 2500 has a plurality of inwardly, radially extending teeth 2514 formed about the inner periphery of the ring, and a plurality of outwardly, radially extending teeth 2502 formed on the bottom surface of the indicator member around the outer periphery thereof. Both pluralities of teeth are configured as ratchet teeth to allow only for one-way rotation of the indicator member 2500.

Referring to FIG. 46, an engagement member 2573 extends from the indicator member 2060 and engages an engagement surface of one of the ratchet teeth 2502 as the dosage indicator member 2060 completes one full cycle. As the engagement member 2573 engages the engagement surface of one of the teeth 2502, the indicator member is rotated an incremental amount.

Figure 51:
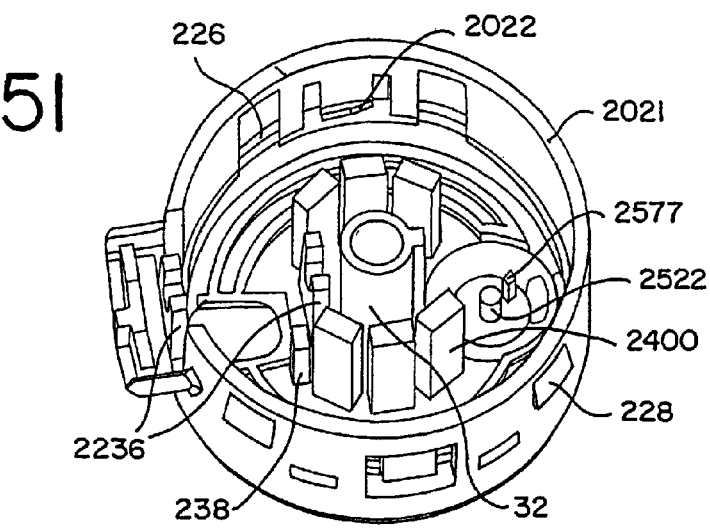
FIG. 51 is a bottom perspective view of the cap member shown in FIG. 44.
Figure 52:
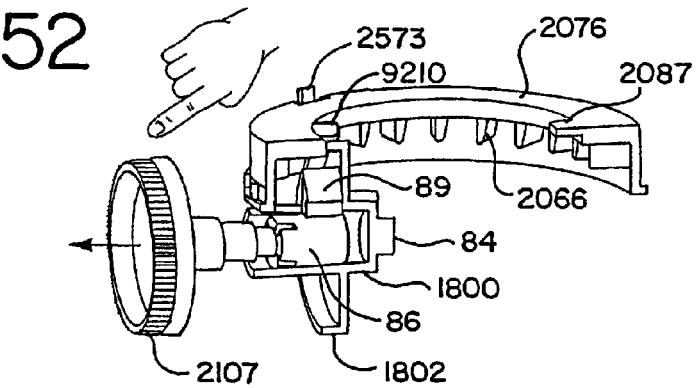
FIG. 52 is a cut-away perspective view of the reset member shown in FIG. 44 with the drive member in a disengaged position.
Figure 53:
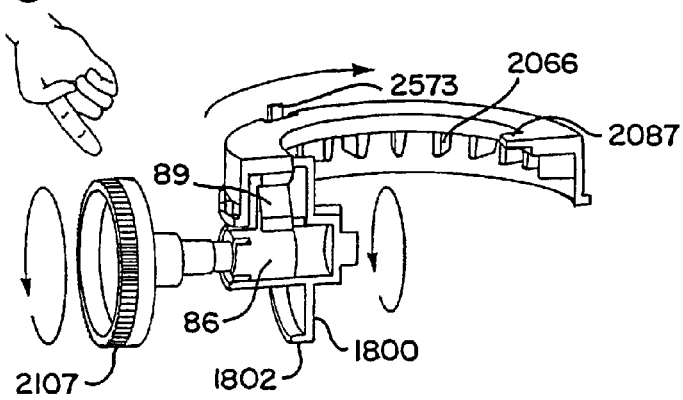
FIG. 53 is a cut-away perspective view of the reset member shown in FIG. 44 with the drive member in the engaged reset position.

Referring to FIG. 51, an indexing member 2577 extends downwardly from the cap member 2020 in a parallel and spaced apart relationship with the post 2522. The indexing member 2577 is disposed in the space between the hub 2520 and the ring 2524 and selectively engages the inner teeth 2514 formed around the inner periphery of the ring. Again, the indexing member 2577 and teeth 2514 are preferably configured to allow for only one-way rotation of the usage indicator member 2500 relative to the cap member 2020. The number and angular spacing between the inner and outer teeth 2514, 2502 correspond such that the advancement of the indicator member 2500 by way of engagement of the engagement member 2573 with one of the outer 2502 teeth further advances the indexing member 2577 one tooth 2514 along the inner periphery of the ring. The predetermined number of usages for the indicating device corresponds to the number of teeth formed around the inner periphery of the ring. After the completion of the final usage cycle, the indexing member 2577 is brought into engagement with the rib 2526, which functions as a stop member and does not permit the indicator member to be further rotated or advanced. At the same time, the engagement member 2573 is brought into engagement with one of the teeth 2502 formed about the outer periphery of the ring such that the indicator member also cannot be advanced. In this way, the device is immobilized. Again, the indicating device can be provided with a predetermined number of inner and outer teeth, which corresponds to the number of predetermined usage cycles for the indicating device.

The upper surface 2528 of the indicator member ring, which is preferably domed, is provided with usage indicia to indicate the number of usage cycles completed or remaining for the indicating device. The usage indicia is visible to the user through a viewing window 2600 provided in the cap member, as shown in FIG. 44. Again, the usage indicia can take the form of various alphanumeric characters, colors or any of the other varieties described above.

Referring to the embodiments shown in FIGS. 118-135, 141, 142 and 145-153 the operation of the indicator assembly includes moving the cap member toward the base member as the container is moved longitudinally within the housing 10 so as to depress the valve stem 110 to the open position so as to open the valve as explained above. As the cap member is moved toward the base member, in one embodiment, the pawl 48 is moved longitudinally toward such that the end portion thereof biased outwardly by the ratchet gear 6552 on a first outer indicator member. At the bottom of the stroke, the end portion, formed for example as a hook, slips into an overlying relationship with the teeth on the ratchet gear. When the cap member is released by the user, the spring biases the cap member away from the base member along the longitudinal axis. As the cap member moves away from the base member, the resilient arm member 6570 moves longitudinally such that the end portion rotates the first indicator member a predetermined angular or incremented amount corresponding to the pitch of the teeth disposed around the periphery of the ratchet gear. As the cap member and ratchet gear reach the top of the stroke, the pawl 48 is positioned for the next cycle. The term incremental is meant to refer to the angular amount the indicator member is moved by the advancement of one actuation, which corresponds to the movement of one tooth, regardless of whether the indicating device is indicating the number of doses left (e.g., counting down) or indicating the number of doses administered (e.g., counting up).

Alternatively, the operation of the pawl and ratchet gear can be reversed. In particular, the pawl engages and rotates the ratchet gear on the first primary indicator wheel as the cap member is moved toward the base member. On the return stroke, as the cap member moves away from the base member, the arm member is biased over the teeth until it is engaged with another tooth at the top of the stroke.

The reciprocal movement of the cap member relative to the base member is repeated until the first primary indicator member 6550, and its ratchet gear, are rotated one complete revolution. The predetermined number of reciprocal movements required to advance the first indicator member one revolution is equal to the number of teeth disposed about the periphery of the ratchet gear 6552. As the first indicator member is rotated by successive movements of the cap member relative to the base member, the advancement member 6600 of the first indicator member is brought into selective engagement with the engagement member, configured as either the ramped surface formed in the cap member or as an arm member extending from the cap member. In particular, the engagement member biases the tooth portion of the advancement member into engagement with one of the teeth of the ratchet gear on the second primary indicator member.

The second primary indicator member with its advancement member similarly interacts with a second engagement member overlying the teeth of the third indicator member so as to selectively engage and advance the third primary indicator member a predetermined incremental amount for each complete rotation of the second indicator member. It should be understood that more indicator members could be similarly assembled to provide an incremental indicating device.

Alternatively, as explained above with respect to the embodiment of FIG. 145, the advancement tooth rotates the advancing gear, which rotates the next adjacent indicator wheel.

Various indicating devices and components thereof are disclosed in U.S. Pat. Nos. 6,082,358, 6,336,453 and 6,328,037, all of which are hereby incorporated herein by reference.

Description of Primary Indicating Device Disposed in Bottom of Dispenser Housing:

Now referring to FIGS. 71 and 72, an aerosol dispenser is shown as including a housing, a container mounted therein as described above and an indicator assembly. The indicator assembly includes a ratchet gear 7032 coaxially mounted with a worm 7040 on an axle 7042 in a lower portion of the housing. A plurality of teeth 7034 are formed about the periphery of the ratchet gear. The teeth 7034 are cut or formed with a tapered surface 7036 and engagement surface 7038. In a preferred embodiment, the ratchet and worm are formed out of a hard durable plastic. It should be understood, however, that other materials such as metal would also work.

The ratchet and worm can be made as separate parts, or molded as a single integral member.

In a preferred embodiment, the axle 7042 and worm 7040 define an axis of rotation transverse, or perpendicular, to the longitudinal axis defined by the valve stem and reciprocal movement of the container relative to the housing. Opposite ends of the axle 7042 are rotatably supported in the housing.

Also as shown in FIGS. 71 and 72, an indicator member 7050 comprises a circular worm gear 7052 and indicator wheel 7058 coaxially mounted on an axle. In a preferred embodiment, the axle 7056 defines an axis of rotation transverse to the axis defined by the worm and also transverse to the longitudinal axis defined by the reciprocal movement of the container relative to the housing. The axle 7056 is rotatably supported in the housing. Teeth 7054 are formed around the periphery of the worm gear 7052 and are shaped to permanently engage the worm 7040. As shown in FIG. 71, the indicator wheel 7058 has a planar face 7060 which is exposed to the patient through a viewing window 7028 formed in the housing.

Figure 75:
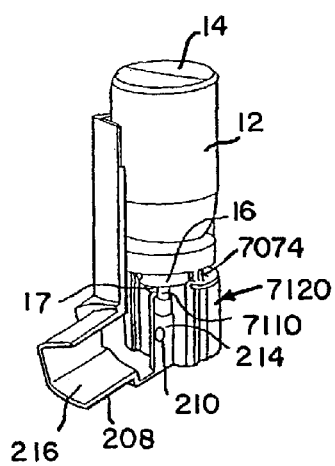
FIG. 75 is a perspective view of a container, a dispenser housing and one embodiment of an indicator module with a portion of the housing cut away.
Figure 81:
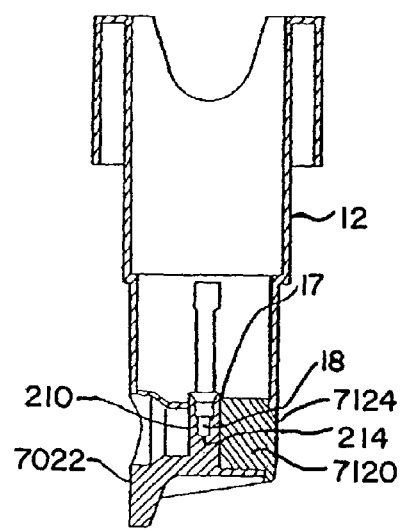
FIG. 81 is a section cut of a housing and an indicator module mounted therein.

The ratchet gear 7032, worm 7040, worm gear 7052 and indicator wheel 7058 provide an ideal arrangement for indicating the number of doses remaining in the container, or the number dispensed therefrom. In particular, relatively high reduction ratios are made possible through use of the ratchet, worm and worm gear without the corresponding requirement of providing extremely fine teeth on one or more of the ratchet gear and worm gear. Moreover, the worm and worm gear interface avoids the associated inaccuracies introduced by the mating, and potential skipping, of conventional spur gears having fine teeth. Furthermore, the installation of the indicator member is effected by the installation of a simple axle which can be supported in a plurality of positions and angular orientations within the housing. Importantly, the high reduction ratio realized with the worm 7040 allows for the worm gear 7052 to have a relatively small diameter, such that it can be easily mounted within small spaces within the housing. Indeed, as shown in FIGS. 75 and 81, the entire indicator assembly can be mounted behind the support block 7016 and below the upper surface 7017 thereof such that the assembly does not interfere with the dispensing of the medicament from the orifice or with the airflow generated by the patient in administering the medicament.

Figure 74:
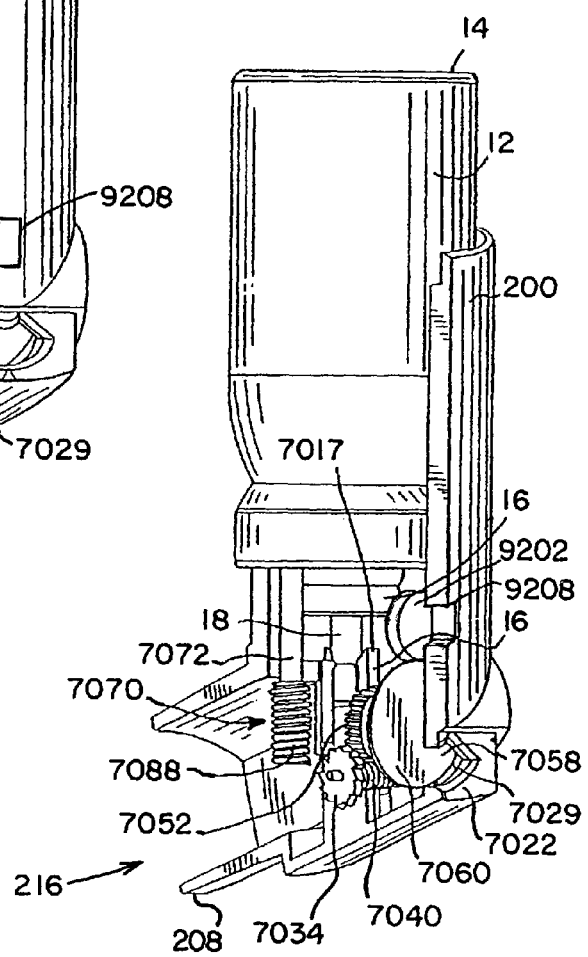
FIG. 74 is a perspective view of the dispensing device shown in FIG. 73 with a portion of the housing cut away.
Figure 76:
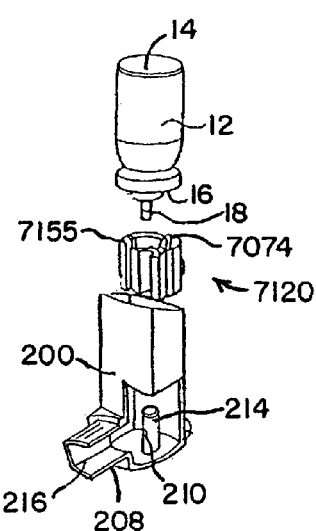
FIG. 76 is an exploded perspective view of a container, a dispenser housing and one embodiment of the indicator module with a portion of the housing cut away.

Referring to FIG. 74, an actuator member 7070 is configured as a post member 7072 moveably supported in the housing along an axis parallel to the longitudinal axis defined by the reciprocal movement of the container within the housing. In an alternative embodiment shown in FIGS. 76-78, the post member includes an upper portion 7074, a middle portion 7076 and a lower portion 7078. A resilient arm member 7080 extends from the middle portion of the post member and terminates in a tapered hook member 7082 shaped to selectively engage one of the ratchet wheel teeth. The middle portion 7076 is defined by upper and lower stop surface 7084, 7086. A spring 7088 is disposed about the lower portion 7078 of the post member and engages the lower stop surface 7086 so as to bias the actuator member upwardly against the top surface of the canister as shown in FIG. 76. Although a compression spring is shown in the Figures, it should be understood that cantilever, torsion, leaf and tension springs, and the like, would also work to bias the actuator member upwardly into engagement with the container. The springs can be made of metal or plastic.

In an alternative embodiment, shown in FIGS. 71 and 72, actuator member 7090 includes locking ring 7092 and a resilient arm member 7094 extending longitudinally downwardly therefrom. A longitudinal slit 7096 is formed in the locking ring so as to allow for the locking ring 7092 to be expanded and disposed around the hub 16 (shown in FIG. 74) of the canister in a snap fit configuration such that the valve stem of the container extends through opening 7098 of the locking ring. In this way the actuator member is fixedly attached to the container and is removable therewith. If the actuator member is further secured within the module housing, such that it cannot be disengaged therefrom, the entire indicator module is fixedly secured to the container and is removable therewith from the dispenser housing. A distal end of the resilient arm member terminates in a hook member 95 that is shaped to selectively engage the teeth of the ratchet wheel.

Referring to FIGS. 94 and 138-140, an alternative embodiment of an indicator assembly is shown. The indicator assembly includes three indicator members 7550 coaxially mounted on an axle 7556 and rotatable thereabout. As best shown in FIGS. 97, 98 and 138-140, each of the indicator members includes an indicator wheel 7558 having a circumferential skirt 7559 with an outer circumferential surface 7560 on which indicia (shown as numbers) are applied, and a ratchet gear 7552 coaxially mounted with the indicator wheel. The indicator wheel and ratchet gear have an opening 7553 shaped to receive the axle. Alternatively, the middle indicator wheel is integrally formed with an axle portion extending laterally from both sides thereof, with the other indicator wheels mounted thereon on opposite sides thereof. The ratchet gear 7552 includes a plurality of teeth 7554 formed around its periphery. The ratchet gear is preferably integrally molded with the indicator wheel, although it should be understood that the gear and wheel can be made separately and thereafter attached one to the other by welding, adhesive and the like.

In one embodiment of the indicator member, a resilient advancement member 7600 is formed from a portion of the circumferential skirt 7559 by providing an elongated cutout 7602 in the indicator wheel radially inward from and beneath the skirt. The advancement member 7600 includes a laterally extending tooth portion 7604 having an engagement surface 7606. The three indicator members are coaxially mounted such that the tooth portion 7604 of the advancement member of a first indicator member overlies the ratchet gear teeth 7554 of the second indicator member, and such that the tooth portion 7604 of the advancement member of the second indicator member overlies the ratchet gear teeth 7554 of the third indicator member. When only three indicator members are used (as shown in FIGS. 94 and 138-140), the third indicator member does not require an advancement member, although for the sake of simplicity in manufacturing, a modular indicator member with the same indicia applied thereto and the same advancement member formed thereon is preferably used for each of the first, second and third indicator members. It should be understood by one of skill in the art that one or more indicator members may be used to provide an indication of dosages used or available, and that the three indicator members shown in the Figures is meant to be illustrative, rather than limiting. In addition, it should be understood that a plurality of indicator members refers to any number of indicator members greater than one.

Figure 111:
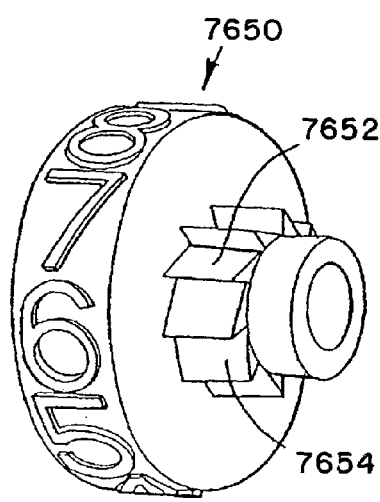
FIG. 111 is a perspective side view of an alternative embodiment of an indicator member.
Figure 112:
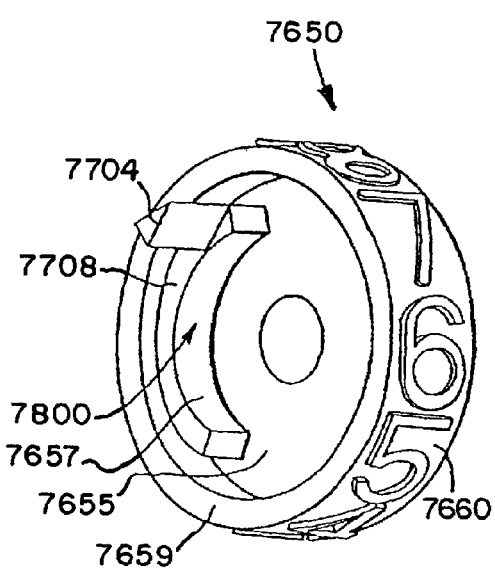
FIG. 112 is an opposite perspective side view of the indicator member of FIG. 111.

In an alternative embodiment of the indicator member 7650, shown in FIGS. 108, 111 and 112, an advancement member 7800 is disposed radially inward from a circumferential skirt 7659 and includes a first end 7657 connected to a planar side portion or hub 7655 of the indicator wheel. The advancement member includes a curved resilient portion 7708 having a free end with a tooth portion 7704 extending laterally outward therefrom so as to extend laterally from beneath the skirt 7659 of the indicator wheel such that it overlies the teeth of the ratchet gear of an adjacent indicator member coaxially mounted therewith as shown in FIG. 48. Indicia, preferably in the form of numbers, are applied to the circumferential surface 7660 of the skirt. A ratchet gear 7652, having a plurality of teeth 7654 is coaxially mounted with the indicator wheel. As shown in FIG. 117, three indicator members are coaxially mounted on axle 7656.

Referring to FIGS. 94, 108 and 138-140, an actuator member 7570, 7670, otherwise referred to as a ratchet member, is shown as having an upper portion 7574, 7674 extending upwardly from a lower portion 7578, 7678 and a resilient arm member 7580, 7680 extending outwardly therefrom and terminating in a resilient hook member 7582, 7682 shaped to selectively engage at least one of the teeth of the ratchet gear of the first indicator member. A spring 7588, 7688 is disposed around the lower portion of the actuator member and biases the upper portion 7574, 7674 of the actuator member into engagement with the container.

Figure 96:
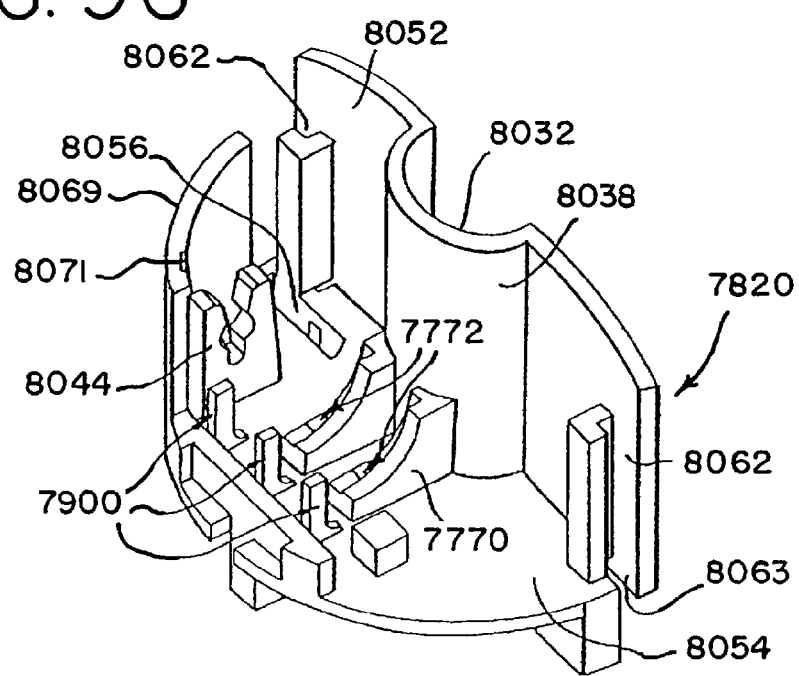
FIG. 96 is a bottom perspective view of the member shown in FIG. 95.
Figure 104:
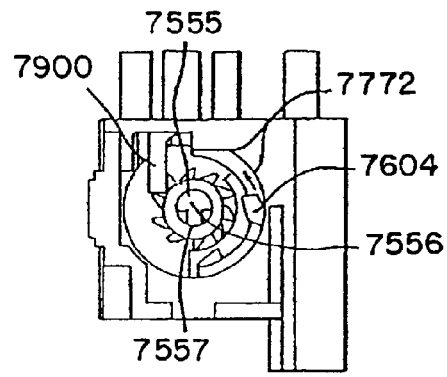
FIG. 104 is a cross-sectional view of an indicator module showing an advancement member of a first indicator member, an engagement member and a second indicator member.
Figure 105:
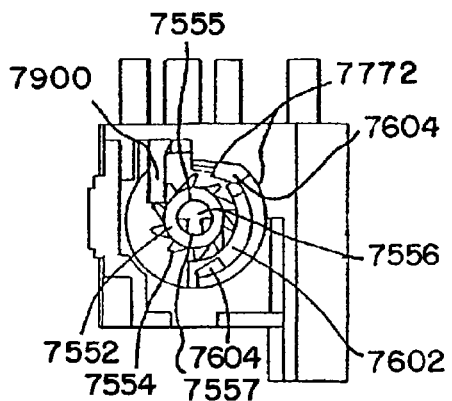
FIG. 105 is a cross-sectional view of the advancement member of the first indicator member as it is first engaged by the engagement member in the indicator module housing.
Figure 106:
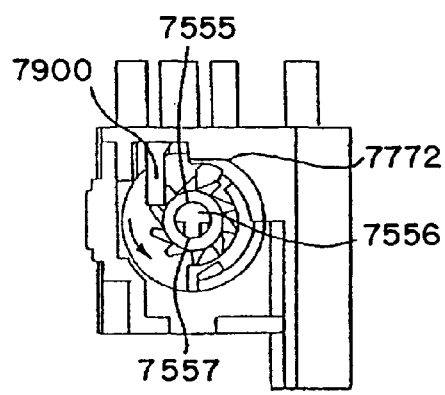
FIG. 106 is a cross-sectional view of the advancement member as it is biased by the engagement member into engagement with the second indicator member so as to rotate the second indicator member.
Figure 107:
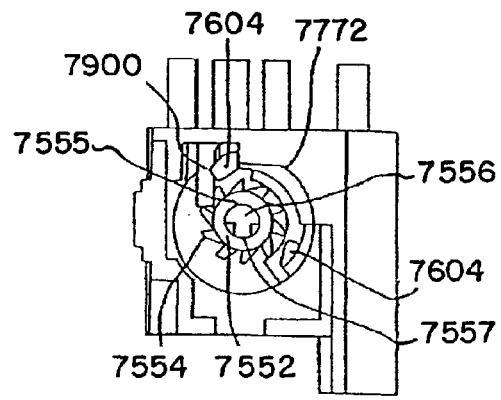
FIG. 107 is a cross-sectional view of the advancement member as it is released by the engagement member and disengages from the second indicator member.

Referring to FIGS. 96 and 143, a housing 7820 is shown as having a pair of engagement members 7770 formed integrally with the housing and including ramped surfaces 7772. A plurality of non-return members 7900 extend from the housing and selectively engage the ratchet gear to ensure unidirectional rotation of the indicator member as shown in FIGS. 104-107. Although the engagement members and non-return members are shown as being formed in or extending from a module housing, as described below, one of skill in the art should understand that those members or equivalent features could also be formed in or connected to the dispenser housing or actuator boot that supports the container, or disposed on or connected to the container itself.

Referring to FIGS. 94, 104-107 and 136-140, the operation of the indicator assembly is generally shown. In particular, the container is moved longitudinally within the housing 200 so as to depress the valve stem 18 to the open position so as to open the valve as explained above. As the container is moved downwardly within the housing, or downwardly with respect to the module housing described below, the actuator member 7570 is moved longitudinally downward such that the hook member 7582 is biased outwardly by the ratchet gear 7552 on a first outer indicator member. At the bottom of the stroke, the hook member 7582 slips into an underlying relationship with the teeth on the ratchet gear. When the container is released by the user, the spring (not shown) within the container biases the container upwardly within the housing along the longitudinal axis such that the valve stem 18 and valve are moved to the closed position within the container. As the container moves upwardly, the resilient arm member 7580 moves longitudinally upward such that the hook member 7582 rotates the first indicator member a predetermined angular or incremented amount corresponding to the pitch of the teeth disposed around the periphery of the ratchet gear. As the container and resilient arm member reach the top of the stroke, wherein the valve stem and valve are moved completely to the closed position, the resilient arm member 7580 is positioned over the ratchet gear for the next cycle. Alternatively, the operation of the actuator member and ratchet gear can be reversed as explained above with respect to the embodiment shown in FIGS. 75-78.

Figure 110:
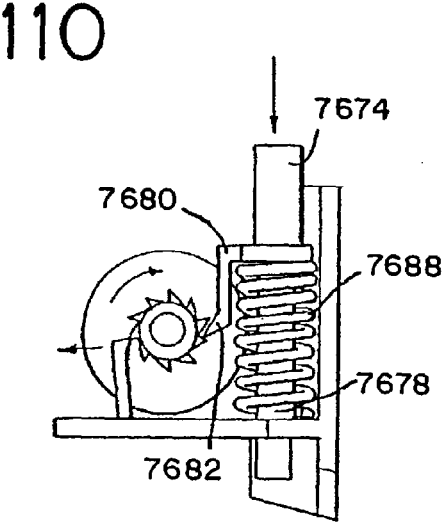
FIG. 110 is a side view of the actuator member engaging the first indicator member with the non-return being biased outwardly.

Referring to FIGS. 107-110 and 113-117, a plurality of resilient arm members 7700 are shown as extending from a module housing so as to be aligned with the ratchet gears on each of the indicator members. The arm members 7700 each serve as a combined engagement member and non-return member. In particular, as shown in FIGS. 109 and 110, the arm member 7700 functions as a non-return member and includes an end portion that is biased away from the teeth on the ratchet gear as the actuator member, or adjacent indicator member with its advancement member, is actuated to advance the ratchet gear. The operation of the actuator member 7670 and ratchet gear is similar to the operation of the ratchet gear shown in FIGS. 75-78 as explained above. The arm member 7700 snaps back so that the end portion engages one of the teeth of the ratchet gear so as to ensure that the rotation of the ratchet gear is unidirectional. As shown in FIGS. 113-117, the arm member 7700 overlying the ratchet gears of the second and third indicator members also serves as an engagement member that selectively engages the advancement members connected to the indicator members.

In a preferred embodiment of the dispenser, shown in FIGS. 75-79, 87, 89, 93, 94, 108, 136-40, 143 and 144, the indicator assembly is arranged in an indicator module 7120, 8020, 8120, 8220. The indicator module 7120, 8020, 8120, 8220 is shaped to be received within the housing where it is disposed around a portion of the support block 212. In particular, the support block is spaced apart from the wall of the dispenser housing, otherwise referred to as the actuator boot, so as to form a donut-shaped socket in the bottom of the housing. The module includes a module housing 7130, 8030, 8130, 8230 having an inner concave surface 7132, 8032, 8132, 8232 that is shaped to mate with an outer convex surface of the cylindrical support block and an outer convex 7134, 8034, 8134, 8234 surface that is shaped to mate with the inner concave surface of the housing which is also generally cylindrical. In this way, the module housing is shaped to be received within the socket formed around the support block. Preferably, the module housing has a semicircular shape and fits around a portion of the support block opposite the orifice opening so as to not interfere with the dispensing of the medicament, or the airflow transmitting the medicament to the patient. In this way, the module is maintained rearwardly of the midpoint of the support block. One of skill in the art should understand, however, that the module, or module housing, can be configured in any number of different sizes and shapes so as to be accommodated in a variety of housings or cap assemblies, with or without support blocks and the like.

Figure 77:
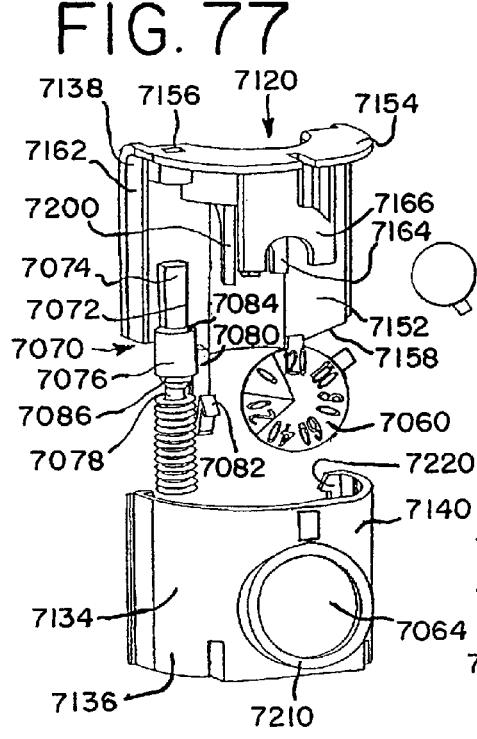
FIG. 77 is an exploded perspective view of one embodiment of the indicator module.
Figure 78:
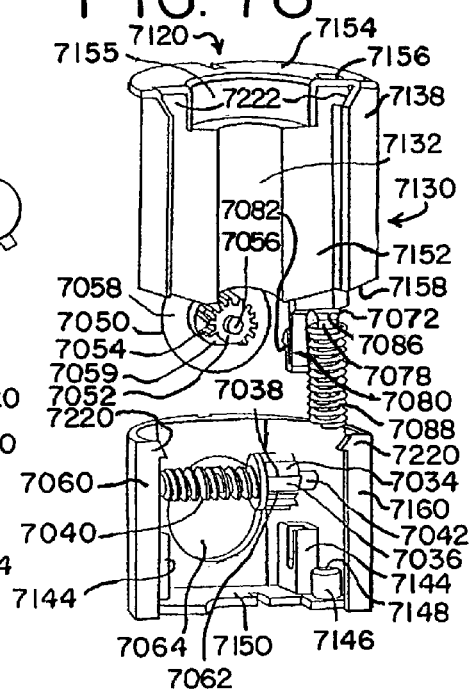
FIG. 78 is an exploded perspective view of the indicator module from the opposite side as shown in FIG. 77.

As shown in FIGS. 77-78, one embodiment of the module preferably includes a face portion 7210 that extends from the rear convex surface of the module and includes a module viewing window 7064. The face portion snaps into the housing viewing window opening (circular opening not shown) so as to secure the module thereto. As shown in an alternative embodiment in FIGS. 79-81, the face portion includes a vertically oriented rectangular viewing window 768 and a downwardly extending locking member 7122 which extends through the dispenser viewing window opening 7124 and engages a bottom wall of the housing. In yet other embodiments, shown for example in FIGS. 93 and 99, the face portion 8031, 8131 and viewing window 8064, 8164 have an elongated horizontal orientation so as to provide the user with a view of the plurality of indicator members mounted within the module. It should be understood, however, that the module can be secured within the housing by any number of conventional means, including the use of fasteners or adhesive. Alternatively, the module can simply be press fit into the socket formed between the support block and housing wall.

In the embodiment shown in FIG. 77, the circular viewing window 7064 is provided in the module housing so as to expose a substantial portion of the planar indicator wheel. Numerical indicia, corresponding to the number of doses in the container, are provided on the face 7060 of the indicator wheel. An arrow, or like indicator, is applied to the housing adjacent the viewing window and provides an indication of the number of doses remaining in the housing, or the number dispensed therefrom, as the indicator wheel is rotated.

In other alternative embodiments, shown for example in FIGS. 79, 80, 94, 108 and 136-138, the indicia are applied to a circumferential surface 7062, 7560, 7660 of the indicator wheel. The module viewing window 7068, 7064, 8164, which is preferably rectangular, and indicator wheel are arranged such that the circumference, or periphery, of the wheel, or wheels, is visible through the module and dispenser viewing windows. Alternatively, as shown in FIG. 138, a plurality of viewing windows are provides in the module housing. As with the other embodiments, the indicia can take the form of color coding, shading, alpha-numerical characters and the like.

In the embodiments shown in FIGS. 97-98, 111-112 and 138-140, the indicia are preferably formed around the circumferential surface 7560, 7660 of the indicator wheel in the form of numbers ranging from 0 to 9, with the ratchet gear on the indicator member having 10 teeth. In operation, it should be understood that the three, or more or less, indicator members can be preset to the maximum number of dosages contained within the container, with the indicia, or in this case numbers, arranged about the periphery of the indicator wheel, such that successive, sequential actuations of the container cause the indicator members to count down.

Alternatively, the indicator members are assembled such that the zero (0) of each indicator member is displayed in the viewing window to the user. The container is then actuated by the user such that the first indicator member rotates within the housing to sequentially display the number of doses that have been dispensed from 1 to 9. Upon the tenth actuation, the indicator member completes a single revolution, by virtue of the ten teeth preferably formed about the ratchet gear which correspond to the predetermined number of actuations, and causes the second indicator member to advance one number from 0 to 1 as the first indicator member again displays a 0 such that the two members together indicate that 10 dosages have been dispensed. The first indicator member is again rotated by successive actuations until another single rotation is completed to further rotate the second indicator to reveal the 2, so as to indicate that 20 dosages have been dispensed. Upon a complete rotation of the second indicator member, corresponding to 100 actuations, the third indicator member is advanced to reveal a 1 in the viewing window with the first and second indicator members revealing a 0, and so on.

As shown in FIGS. 75-79, 82-87 and 99, one embodiment of the indicator assembly, including the worm, worm gear, ratchet gear and indicator member, is mounted within the module housing 7130. Similarly, the embodiments of the indicator assembly shown in FIGS. 94, 108, 136-140, 143 and 144 are also preferably supported in a module housing 8030, 8130, 8230. The module housing is preferably formed from a first and second cover member 7136, 7138, 8036, 8038, 8136, 8138, 8236, 8238 although it should be understood that a single, integral piece of material would also work, as would any plurality of members joined together. Referring to FIGS. 75-79, 99, 108, 138-140, 143 and 144 the first cover member 7136, 8136, 8036, 8236 has a vertical wall 7140, 8140, 8040, 8240 defining at least a portion of the outer convex surface 7134, 8034, 8134, 8234 shaped to mate with the inner surface of the housing as described above. The secondary viewing window 764, 8064, 8164 of the module is provided in the vertical wall 7140, 8040, 8140 so as to be aligned with the viewing window of the housing when the module is installed therein. The viewing window is framed by the face portion. In the embodiment of FIGS. 136-140, 143 and 144 the cover member 8236 is made of a clear material, such that it is see-through. alternatively, the first cover member can be omitted altogether, with the module housing formed only from the second cover member 8238 such that the indicator members are exposed to the ambient environment. The cover has a protrusion 8231 that is shaped with and extends into an opening formed in the dispenser housing. The first cover member 8236 further includes a top wall 8154 or flange that extends from the wall 8240.

In one embodiment, shown in FIG. 78, the first member also includes a pair of opposing bearing seats 7144 formed on an inner surface of the vertical wall. The bearing seats 7144 are shaped to support the ends of axle 7042. Alternatively, as shown in FIGS. 96 and 99 a bearing seat or lug 8044 can be formed on each of the first and second cover members. Alternatively, as shown in FIG. 140, the bearing seats 7144 are formed in the cover 8236. As best shown in FIGS. 78 and 99, a post member 7146, 8046 extends upwardly from a base 7150, 8050 of the first member adjacent one of the bearing seats and has a socket 7148, 8048 formed coaxially therein. Alternatively, as best shown in FIG. 108, the base 8150 is formed as part of the second cover member and includes an opening 8148 shaped to receive the lower portion 7678 of the actuator member.

Referring to FIGS. 77-78, 140, 143 and 144, the second cover member 7138, 8038, 8138, 8238 mates with the first cover 7136, 8036, 8136, 8236 to form an enclosure therebetween. The second cover member includes a vertical wall 7152, 8052, 8152, 8252 a portion of which defines the concave surface 7132, 8032, 8132, 8232 shaped to mate with the outer surface of the support block. An upper horizontal flange 7154, 8054, 8154 extends from the vertical wall 7152, 8052, 8152 and mates with the vertical wall of the second member in overlying relationship therewith so as to close off the top of the module. In an alternate embodiment, shown in FIGS. 143 and 144, the upper flange 8154 is formed as part of the first cover member. The upper flange 7154, 8054, 8154 has an opening 7156, 8056, 8156 formed therein which is shaped to receive the upper portion 7074, 7574, 7674 of the post member. In one embodiment, the upper surface of the flange is maintained parallel with or below the top surface of the support block so as not to interfere with the container as it is depressed toward the support block. Alternatively, as shown in FIGS. 77 and 78, the module housing is provided with a semi-circular recess 7155 shaped to receive the hub as the container is actuated whereby a surface of the container engages the upper portion 7074 of the actuator member and the surface is positioned adjacent to the surface 7154 of the module housing when the valve is moved to the open position. A bottom edge 7158 of the vertical wall mates with the base 7150 of the first cover member to close off the bottom of the module. As shown in FIGS. 77-78, 94-96 and 99, the cover members are joined by slidably engaging vertical flanges 7160, 8060 on the first cover member with grooves 7162, 8062 formed on the second cover member. Inwardly extending tabs 7220, 8061 snap fit into slots 7222, 8063 formed in the second cover member. In the embodiment shown in FIGS. 95, 96 and 109, a tab member 8067 engages opening 8071 formed in a wall member 8069 that further defines a portion of the outer concave surface of the module housing. In the embodiment of FIGS. 143 and 144, the first and second cover members also are preferably connected by snap fit. Alternatively, it should be understood that the first and second cover members can be joined with fasteners, adhesive and the like.

As best shown in FIGS. 26, 84, 101, 117 and 138, when the cover members are assembled to form the module housing, the upper portion 7074, 7574, 7674 of the post member extends through the opening in the upper flange of the first cover member and engages the top surface of the container, which is inverted in the housing. Alternatively, the actuator member can be attached to the hub of the container with the locking ring as previously described. In such an embodiment, the arm member of the actuator member extends downwardly from the ring through the opening in the top of the first cover member and is positioned to selectively engage the ratchet gear. The insertion of the arm in the opening prevents the canister and attached locking ring from being rotated so as to move the arm member out of position for selective engagement with the ratchet gear.

Figure 94:
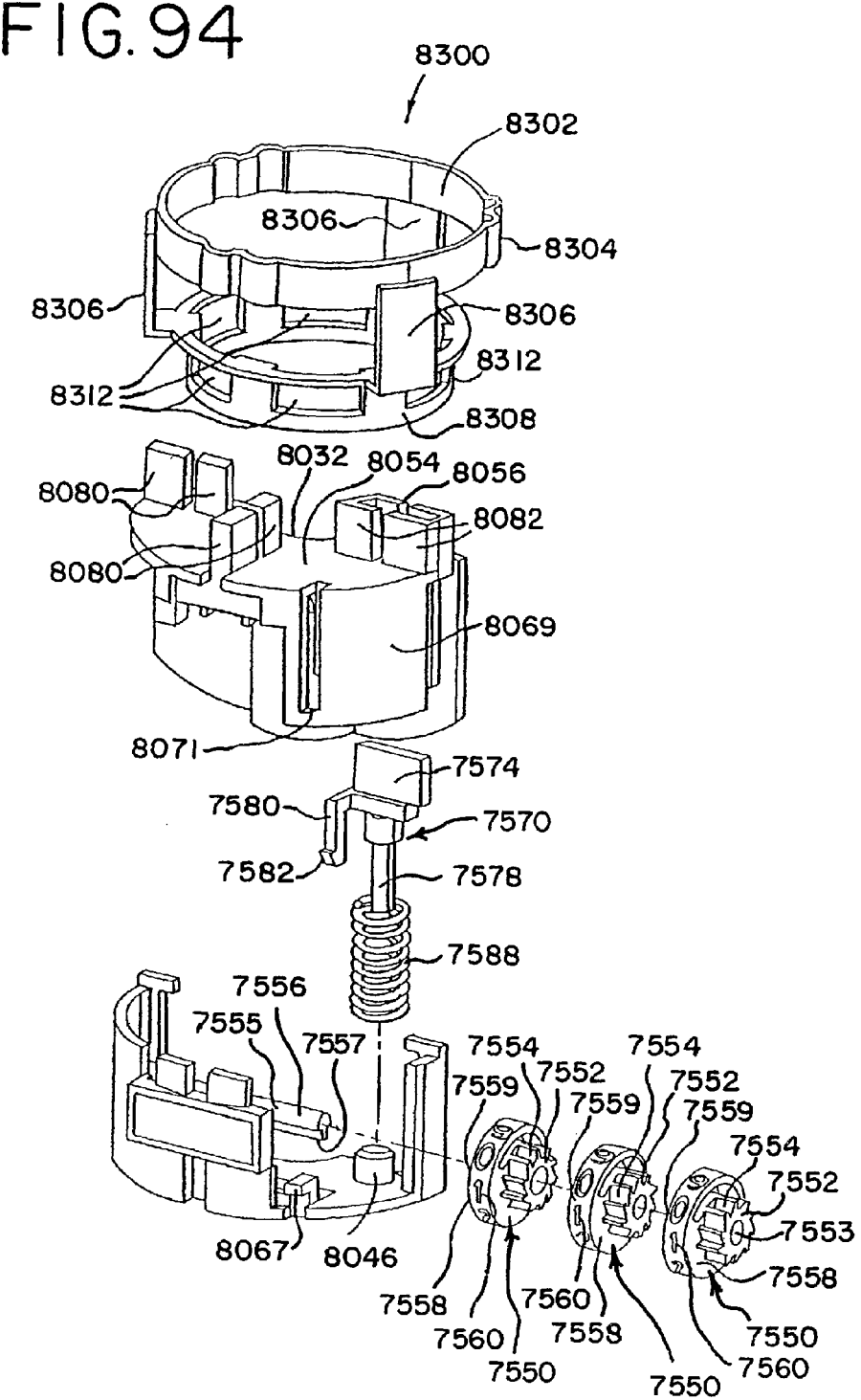
FIG. 94 is an exploded perspective view of an alternative embodiment of an indicator module, key member and indicator assembly.
Figure 95:
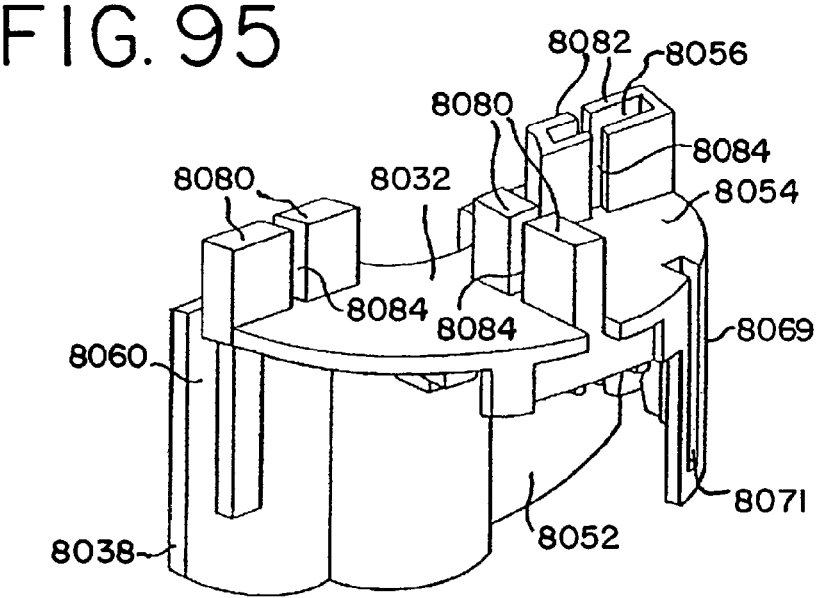
FIG. 95 is a top perspective view of a first member of one embodiment of the indicator module housing.

As best shown in FIGS. 78 and 94, the lower portion 7078, 7578 of the post member is moveably received within the socket 7148, 8048 formed in the post member 7146, 8040 extending from the base of the second cover member. Alternatively, the lower portion 7678 is received in the opening 8148 as shown in FIG. 108. Referring to FIGS. 78, 94, 108 and 138-140, springs 7088, 7588, 7688 is disposed about the lower portion 7078, 7578, 7678, and in certain embodiments includes a lower end mounted on the post member 7146, 8046. The upper end of the spring engages the lower stop surface 7086, 7586, 7686 of the post member 7072, 7572, 7672. The spring biases the post member upwardly within the housing such that the upper portion 7074, 7574, 7674 protrudes through the opening and into engagement with the top surface of the container.

In one embodiment, shown in FIGS. 77 and 78, the worm 7040 and ratchet gear 7032 are rotatably supported on the bearing seats 7144 formed in the second member. Preferably, opposite ends of axle 7042 are snap fitted into the bearing seats. The indicator member 7050 is rotatably supported by the second cover member such that the worm gear engages the worm when the cover members are joined together. In particular, the second cover includes a pair of downwardly opening lug members 7164, 7166. The axle 7056 of the indicator member is received in the first lug member 7164 and a hub portion 7059 positioned between the worm gear and the indicator wheel is received within the second lug member 7166. Preferably, the axle and hub are snap fitted into the lugs, but are permitted to freely rotate therein. When the cover members are joined, the indicator member, and in particular the worm gear, are trapped between the lug members and the worm.

In an alternative embodiment shown in FIGS. 94-96, 99, 140, and 143 the axle 7556 is supported on opposite ends by the lug portion 1044, 7144 extending from each of an upper and lower cover members 1036, 1038, 8238. In one embodiment, the axle 7556 has a T-shaped cross-section formed as a result of a molding process. When the axle can be integrally formed or molded with one or more of the module housing cover members. In one embodiment, the shape of the axle permits it to act as a key member when received in similarly shaped sockets formed in one or more of the lug portions. The axle extends outwardly from the lug portion. In one embodiment, the axle includes opposite curved surfaces 7555, 7557, as best shown in FIGS. 94-97 that provide a supporting surface for the indicator members that are rotatably mounted thereon. One of skill in the art should understand that the axle could have a circular cross-section and could be rotatably mounted to the housing. In such an embodiment, at least one of the indicator members can be integrally formed with the axle, or all of the member can be separately mounted thereon.

It should be understood that in the alternative embodiment of FIGS. 71-74, the supporting structure for the worm and ratchet, including the bearing seats or like supports, and the supporting structure for the indicator member, including the lug members, are similar to the structure provided in the module housing, but are integrally molded into the housing. Similarly, a post and socket member can be integrally molded into the bottom of the housing so as to support the actuator member and spring.

Similarly, although the indicator assembly embodiments of FIGS. 94, 108 and 136-140 are shown as preferably being mounted in the indicator module, one of skill in the art should understand that the assembly, including the axle, indicator members, actuator member and spring could be mounted directly in the dispenser housing or actuator boot that supports the container. Similarly, the engagement member, or members, and non-return member, or members, could be formed in the dispenser housing that supports the container, otherwise referred to as the actuator boot.

In an alternative embodiment shown in FIG. 88, a lower portion 7172 of the outer vertical wall of the module housing is angled so as to a mate with a housing having a similar angled planar bottom surface. As shown in FIG. 88, the axis of rotation of the indicator member is oriented at an angle of approximately 45 degrees from the longitudinal axis so that the face of the indicator wheel 7060 is substantially parallel to the angled surface of the housing. A viewing window is provided in the angled surface 7172 and is aligned with a similar viewing window provided in the angled wall of the dispenser housing.

Now referring to FIGS. 90-92, a key member 7300 is shown as including a base portion 7302 having a recess 7304 shaped to receive the top of the container. The base portion is circular shaped and is open in the middle. The key member is mounted on the container by press fitting a circumferential flange 7306, which forms the recess, about the container such that the valve stem and hub passes through an opening 7308 formed in the middle of the key member. Alternatively, the key member can be mounted to the container with adhesive or other fasteners. The key member also includes a key portion 7310 extending downwardly from the base portion. The key portion is preferably configured as a circular flange member, although other shapes would also work.

In alternative embodiments shown in FIGS. 94 and 101-102, the key member 8300 includes a mounting portion 8302, configured as a hoop member having a plurality of ribbed portions 8304. The mounting member 8302 is sized to fit over the end of the container such that the ribbed portions grip a portion of the container. A plurality of arm members 8306 secure a key portion 8308 to the mounting member.

In another alternative embodiment shown in FIG. 103, the mounting member 8402 has a smaller diameter than the key portion, and is coaxially disposed with the key portion. A base member 8404 connects the mounting member and key portion. The mounting member includes a plurality of inwardly facing tab members 8410 that engage an outer tapered surface of the hub portion 7106 of the container.

In the embodiments shown in FIGS. 94 and 103, the key portion 8308, 8408 is formed as a circular flange member having a plurality of openings 8312, 8412 formed therein about the circumference thereof so as to allow air to flow through the key member with less restriction. In the embodiment shown in FIGS. 101 and 102, the key portion 8508 includes two coaxially mounted key portions of different diameters, each with a plurality of openings 8512 to facilitate air flow therethrough.

Figure 20:
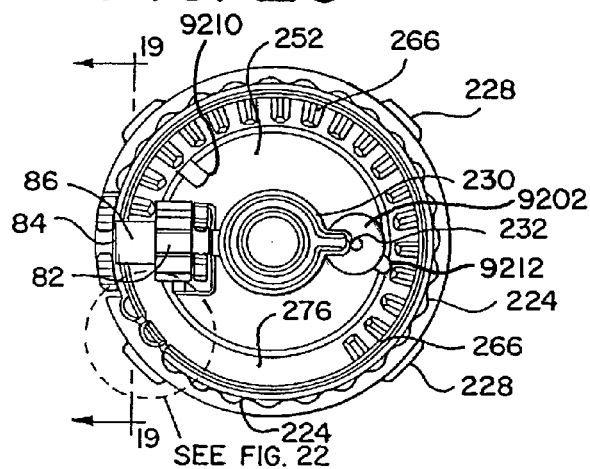
FIG. 20 is a bottom view of the assembly of FIG. 9 (without the spring) after the ratchet wheel and drive member have completed one revolution corresponding to a predetermined number of actuations.

The embodiment of the indicator module shown in FIG. 20 has a key entry passageway configured as a recess 7312 formed in an upper surface of the module housing. Preferably, in this embodiment, the recess is formed as an arcuate shaped, or semi-circular, slot. The actuator member 7314 extends upwardly from the module housing into the slot. The actuator member 7314 is maintained substantially flush with or below the upper surface of the module 7316. In this way, the actuator cannot be actuated by a user's finger or the like so as to inadvertently advance the indicator member and thereby provide an inaccurate reading of the number of dosages remaining in the container, or the number dispensed therefrom.

The shape or diameter of the key portion and corresponding entry passageway are configured so that the key portion communicates with and is received in the passageway formed in the module housing. When the container is mounted in the dispenser housing such that the valve stem is received in the well in the support block, the key portion is received in the passageway and engages the actuator member.

In this way, key members having differently shaped key portions can be applied to containers holding different types of substances, such as a medicament, so as to prevent the user from mixing up the containers and dispensers. In operation, a container having a certain key member with a specific key portion can be installed only in a dispenser housing having a passageway shaped to receive that key portion. If the key portion does not fit the recess, the key ring will engage the upper surface of the module housing so as to prevent the actuation of the container relative to the dispenser housing and the attendant opening of the valve. This in turn prevents a user from installing containers having different substances in different dispensers, which could thereby adversely affect the counting of doses dispensed from the container, or the counting of the number of doses remaining therein. For example, a key member having a key portion with a thickness of 1 mm and an inner diameter of 13 mm is prevented from being installed in a passageway having a width of 1 mm and an inner diameter of 15 mm, and vice versa.

In the alternative embodiment of FIG. 94, the module housing includes three pairs of upstanding members 8080, 8082 forming a slot or recess 8084 between each pair. In addition, the upstanding members of one pair 8082 are formed as channels opening towards each other. The elongated recess 8056 formed between the pair of members is shaped to receive the upper portion of the actuator member 7574. In operation, the key portion 8308 of the key member is shaped to be received in the various radially formed slots or recesses, or key entry passageways, so as to engage the actuator member disposed in the elongated recess. When the container is moved with respect to the module housing so as to move the valve to the open position, the hub of the container nests in a recess formed between the inner upstanding member of each pair.

In the embodiment shown in FIGS. 101 and 102, three sets of three upstanding members 8180, 8182 are provided, with each set of three having two slots 8184 formed between the members so as to be shaped to receive the two key portions 8508 of the key member 8500. Again, one set of three members 8182 forms an elongated passageway, or recess 8056, that is shaped to receive the actuator member. The two key portion configuration allows for multiple combinations of shapes and diameters of key portions so as to provide for a different key combination for each of the multiplicity of substances being dispensed from the various containers.

Although the circular configurations of the key portion and corresponding slots shaped to receive the key portion, as shown in the figures, are preferred since they allow the container to be rotated within the dispenser housing about its longitudinal axis, it should be understood that the key portion and slot, or like passageway or keyhole, can be shaped in any type of mating configuration and that the mating shapes are not limited to the circular configuration shown in the figures.

The indicator module provides an inexpensive and accurate device for counting dosages of medicament and the like. The module can be sized for easy installation as a separate unit in most conventional inhalation housings with minimal modification of the housing, including providing a viewing window in the housing in alignment with the module viewing window and the removal of any structure formed between the support block and outer wall of the housing. In addition, the module can be installed rearwardly of the support block so as not to interfere with or otherwise impede the air flow dispensing the medicament.

Description of Operation of Primary Indicating Device Disposed in Bottom of Dispenser Housing:

In the operation of the embodiment shown in FIGS. 75-78, 82-87 and 89, the container is moved longitudinally within the housing so as to depress the valve stem to the open position so as to open the valve as explained above. As the container is moved downwardly within the housing, the actuator member 7070 is moved longitudinally downward such that the hook member 7082 engages the ratchet wheel and rotates it a predetermined angular amount corresponding to the pitch of the teeth. When the container is released by the user, the spring (not shown) within the container biases the container upwardly within the housing along the longitudinal axis such that the valve stem 18 is moved to the closed position within the container so as to close the valve. As the container moves upwardly, the resilient arm member 7080 is biased laterally outward as a tapered end portion of the hook member 7082 slides against the tapered surface 7036 of one of the ratchet teeth. As the container and resilient arm member reach the top of the stroke, wherein the valve stem is moved completely to the closed position, the resilient arm member 7080 returns to its normal straightened configuration as the hook member 7082 slips past the tapered surface of one of the teeth so as to be positioned over the engagement surface 7038 of that tooth 7034 for the next cycle.

Alternatively, the operation of the ratchet wheel can be reversed as shown in FIG. 72. In this embodiment, the resilient arm member 7094 is biased outwardly by the tapered surface of one of the ratchet gear teeth on the downstroke. At the bottom of the stroke, the hook member 7095 slips into an underlying relationship with the engagement surface of the tooth. When the container is released by the user, the spring (not shown) within the canister biases the container upwardly within the housing along the longitudinal axis such that the valve stem is moved to the closed position within the container. As the container moves upwardly with respect to the housing, the resilient arm member 7094 moves longitudinally upward such that the hook member 7095 engages the engagement surface 7038 of one of the teeth and thereby rotates the ratchet wheel an incremental amount.

In the embodiment shown in FIGS. 75-78, 82-87 and 89, it is the force of the spring 7088 that moves the arm member 7080 upwardly so as to return the actuator member in preparation for another cycle. In the alternative embodiment shown in FIGS. 71 and 72, it is the movement of the container, as it is biased upwardly by the internal spring acting on the valve stem, that causes the locking ring 7092 and arm member 7094 to move upwardly and thereby rotate the ratchet gear.

Referring to FIGS. 77 and 86, a resilient non-return member 7200 engages the ratchet gear adjacent the hook member so as to ensure that the rotation of the ratchet gear is unidirectional. Alternatively, the non-return member can be positioned to engage the ratchet gear opposite the actuator arm member. The non-return member includes an end portion adapted to engage the engagement surface of the ratchet gear teeth. As the ratchet gear is rotated by the actuator, the non-return member slides along the tapered surface of one of the teeth of the ratchet wheel and does not interfere with the rotation thereof.

The rotation of the ratchet gear causes the worm 7040 to rotate a desired predetermined amount. It should be understood that the desired amount of rotation is dependent upon the diameter of the ratchet wheel and the number of teeth positioned thereabout. Rotation of the worm, which permanently engages the teeth of the worm gear, causes the worm gear and indicator wheel to rotate a predetermined incremental amount. The amount of rotation of the indicator wheel is dependent upon the pitch of the worm, the number of worm threads and the pitch of the worm gear and the number of worm gear teeth. In a preferred embodiment, the worm has a single thread.

For ease of manufacturing, it is desirable to provide as coarse a pitch on each of the ratchet and worm gears as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the canister, it is important for the ratchet, worm and worm gear to provide a relatively high reduction ratio, such that 200 linear reciprocal movements of the actuator member correspond to one or less revolutions of the indicator member. Because the ratchet gear and worm rotate together, it should be understood that the number of teeth on the ratchet gear and worm gear, and the number of threads of the worm, determine the ultimate reduction ratio between the rotation of the ratchet gear and the rotation of the indicator wheel.

For example, when the container holds 240 metered doses, an acceptable ratio is realized if the ratchet is made relatively coarse with 10 teeth and the worm gear is provided with 28 teeth. In operation, the dispensing of 10 metered doses will cause the worm to make one complete revolution so as to thereby move the worm gear one tooth. After 240 linear reciprocal movements, the worm gear has been advanced by 24 teeth. Extra teeth are provided so that the starting and ending indicia, indicating a relative fullness or emptiness of the container respectively, are not labeled one on top of the other.

In a preferred embodiment, shown in FIGS. 78 and 84, the worm gear 7052 has teeth formed around only a portion of its periphery so that a gap is formed between the teeth around the remaining portion of the periphery. In operation, the gears are configured so that the worm 7040 disengages from the last tooth of the worm gear as the final prescribed dose of medicament is dispensed. In this position, the indicia on the indicator wheel 7058 will indicate to the user that the canister is empty. Therefore, although the user can continue to move the container so as to open the valve, the resultant movement of the actuator 7070, ratchet gear 7032 and worm will not in turn rotate the indicator member as the gap in the teeth on the worm gear results in the disengagement of the worm and worm gear. In this way, the indicator wheel is prevented from being inadvertently rotated from a full to empty reading and then back again to a full reading, which could confuse the user about the number of doses remaining in the canister.

Figure 73:
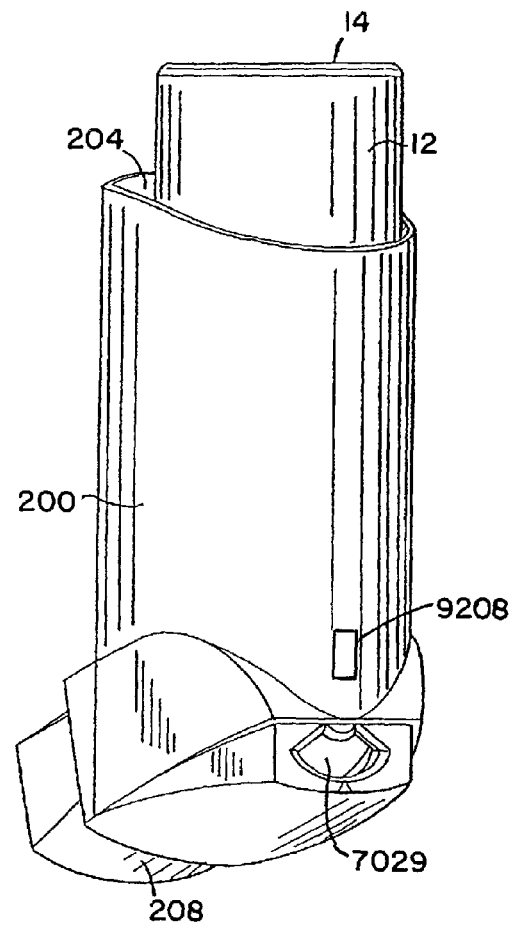
FIG. 73 is a perspective view of an alternative embodiment of the dispensing device.
Figure 79:
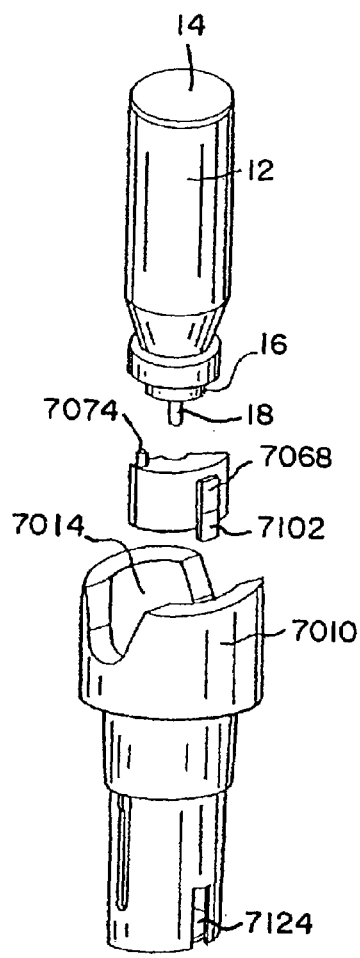
FIG. 79 is an exploded perspective view of a container, and an alternative embodiment of the dispenser housing and the indicator module.
Figure 80:
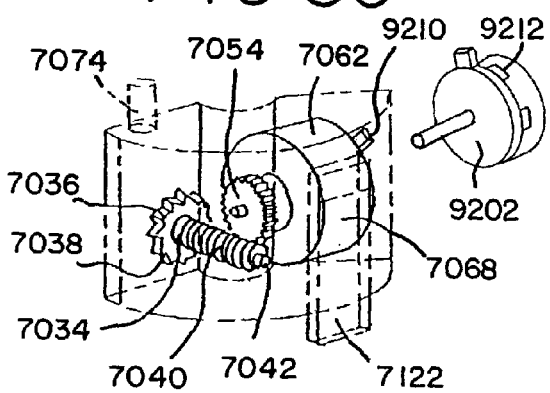
FIG. 80 is a perspective view of the alternative embodiment of the indicator module shown in FIG. 79.

The indicator wheel 7058, indicia 7066 and viewing window 7028 can be arranged in a variety of configurations for viewing by the user. For example, the viewing window 7028, 7124 can be configured as a rectangular shaped window as shown in FIG. 21 or 79 respectively, as an arcuate shaped window 7029 as shown in FIG. 73, wherein approximately ⅓ of the face of the indicator wheel is visible at any time, as a circular shaped window (not shown) or as any other shape allowing the user to view the indicator wheel and the indicia located thereon. In one embodiment, the indicia take the form of a color code, where, for example, a portion of the wheel is colored green to indicate the starting full position, a portion is colored yellow to indicate a medium fullness and a portion is colored red to indicate that the container is empty. Obviously, other colors, shading or alpha-numerical indicia can be provided on the indicator wheel to indicate the relative fullness or emptiness of the container.

In an alternative embodiment, the indicator wheel can be oriented within the housing such that either its planar face or its circumferential surface, with indicia applied thereto, are visible to the user through the exhaust port of the mouthpiece.

In operation of the embodiments shown in FIGS. 94-117 and 136-140, the reciprocal movement of the container relative to the housing is repeated until the first indicator member 7550, 7650, and its ratchet gear, are rotated one complete revolution. The predetermined number of reciprocal movements required to advance the first indicator member one revolution is equal to the number of teeth disposed about the periphery of the ratchet gear 7552, 7652. As the first indicator member is rotated by successive movements of the container relative to the housing, the advancement member 7600, 7800 of the first indicator member is brought into selective engagement with the engagement member, configured as the ramped surface 7772 formed in the housing or as the upwardly extending arm member 7700. In particular, the engagement member 7700, 7772 biases the tooth portion 7604, 7704 of the advancement member into engagement with one of the teeth 7554, 7654 of the ratchet gear on the second indicator member.

As the first indicator member is further rotated by successive movements of the container relative to the housing, whether it be the dispenser housing for the container or the module housing described below, the advancement member 7600 engages one of the teeth on the ratchet wheel of the adjacent indicator member and advances the indicator member a predetermined incremental angular amount corresponding to the pitch of the ratchet gear teeth. The term incremental is meant to refer to the angular amount the indicator member is moved by the advancement of one actuation, which corresponds to the movement of one tooth, regardless of whether the indicating device is indicating the number of doses left (e.g., counting down) or indicating the number of doses administered (e.g., counting up).

As the resilient advancement member 7600, 7800 clears the engagement member 7772, 7700, it springs away from the ratchet gear such that further advancements of the first indicator member do not effect a rotation of the second indicator member until the first indicator member completes yet another cycle so as to again bring the advancement member into engagement with the next tooth of the second indicator member ratchet gear, and so on. The second indicator member 7550, 7650 with its advancement member 7600, 7800, similarly interacts with a second engagement member overlying the teeth of the third indicator member so as to selectively engage and advance the third indicator member a predetermined incremental amount for each complete rotation of the second indicator member. It should be understood that more indicator members could be similarly assembled to provide an incremental indicating device.

Description of Various Embodiments of Secondary Indicator Devices Having Warning Indicator Member:

Referring to the FIGS. in general, the various indicating devices are configured with a secondary or warning indicator member 9002, 9102 that advises the user when the container has less than a minimum predetermined number of dosages of substance left therein, or stated another way, that a predetermined number of dosages have been dispensed therefrom.

Referring to the embodiments shown in FIGS. 129-140 and 147-153, a plurality of primary indicator members 6550, 7550 are arranged in either the module housing 8230, cap member 6020 or base member as explained above. One of the primary indicator members 6550, 7550, hereinafter referred to as a first indicator member and shown as either the first outer indicator member (ones counter) (FIGS. 147 and 153) or the middle indicator member (tens counter) (FIGS. 129 and 132), includes a drive member 9004, configured as a tooth extending from the circumferential skirt of the indicator member. It should be understood that either of the end indicator members can be configured with the drive member.

The secondary or warning indicator member 9002, hereinafter referred to as the second indicator member is rotatably mounted about an axis of rotation 9006 parallel to and spaced apart from the axis of rotation of the primary indicator members 7550, 6550, including the first indicator member. The second indicator member 9002 includes an axle 9008 that is rotatably mounted on a pair of bearing support members 9010 formed in one of the cap member, base member or module housing. The second indicator member 9002 has an outer circumferential surface 9012 with warning dosage indicia applied thereto. Preferably, the warning dosage indicia takes the form of a color coding, for example a portion or zone of the surface is green, while another portion or zone is red. Preferably a plurality of zones is used, for example and without limitation two zones of green and red respectively, or three zones of green, yellow and red. Alternatively, alphanumeric characters, text messages etc. as herein described can be used as indicia. It should be understood that a surface of the indicator member perpendicular to the axis of rotation also can be configured with the indicia. The surface 9012 of the indicator member is visible through a viewing window 9014 formed in the top of the cap member as shown in FIGS. 128, 134, 135 and 149-152. In the embodiment of FIG. 136, the indicia are visible through a viewing window 9016 formed in the dispenser housing. Preferably, the cap member, base member, module housing and/or dispenser housing are provided with at least a pair of viewing windows, one or more viewing windows for the primary dosage indicia and at least one viewing window 9012, 9014 for the secondary warning, dosage indicia, although it should be understood that both types of indicia can be viewed through a single window.

Referring to FIGS. 131, 132 and 148, the second indicator member 9002 further includes at least one driven member 9018, and preferably a plurality of driven members (shown as four in FIGS. 131 and 132 and as ten in FIG. 148), configured in one embodiment as a tooth extending radially outward from the second indicator member on one side of the circumferential indicia surface 9012. Taking into account the spacing between the axes of rotation for the first and second indicator members 7550, 9012, the drive member 9004 and driven members 9018 are configured and have sufficient lengths so as to mesh after a predetermined number of rotations of the first indicator member configured with the drive member. The second indicator member 9002 is also provided with a plurality of ratchet teeth 9020 formed circumferentially around the axis of rotation on the side of the indicator member opposite the driver member 9018. A non-return member 9022 extends from one of the cap and module housing and successively, selectively engages one or more of the ratchet teeth 9020 so as to allow the second indicator member to rotate in only one direction.

Referring to the embodiment of FIGS. 118-127, a second indicator member 9102 is configured as a plate member slidably or translatably mounted to the cap member, which includes guides 9106 or tracks, which can formed by tabs, for the indicator member. The second indicator member 9102 has a surface 9104 with indicia applied thereto. The surface 9104 and indicia are visible in a viewing window formed in the cap member. The second indicator member is translatable in a plane substantially parallel to the axis of rotation of the primary indicator members 6550. In this embodiment, a third primary indicator member is provided with a drive member 9110 having a ramped or tapered surface. The second primary indicator member is also provided with a drive member 9114.

Referring to FIGS. 5, 6, 7, 9, 20, 29, 36, 38, 44, 45, 71, 72, 74, 77 and 80, a secondary warning indicator member 9202 is provided to be advanced or moved in response to the movement of the primary indicator 7062 members 60, 260, 460, 760, 1060, 2060, 7050, 7062. In particular, each of the primary indicator members 7062 is provided with a drive member 9210, configured as a tooth in a preferred embodiment. The second indicator member 9202 is mounted to one of the cap member, base member, module housing or dispenser housing and is rotatable or pivotable about an axis. The axis is preferably parallel to the axis of rotation of the primary indicator members. The second indicator member can be configured with a circular shape, pie shape or any other shape that fills a viewing window 9208, and includes a driven member 9212, configured as a tooth in one preferred embodiment.

In an alternative embodiment, shown for example in FIG. 6, the second indicator member 9102 is configured as a plate or other member that is engaged by the drive member 9210 of the first indicator member and is translated relative to the first indicator member. Preferably, the second indicator member 9102 is translated within a plane either substantially perpendicular to the axis of rotation of the primary indicator member 60, 260, 460, 760, 1060, 2060, 7050 7062, or substantially parallel to the axis, although other orientations are possible.

Operation of Secondary Indicating Device Having Warning Indicator Member:

In operation of the embodiment shown in FIGS. 129-140, the container and actuator, configured either as an arm or cap member, are moved relative to the dispenser housing so as to dispense a dose of substance. After one rotation of a first one of the primary indicator members 6550, 7550 resulting in a plurality of actuations of the container, the middle primary indicator member is rotated an incremental amount as explained above.

In one illustrative and non-limiting example, and referring to FIGS. 130-135 and 147-153, the dosage indicator is provided with 200 or 210 dosages of substance. Referring to the embodiment of FIGS. 130-135, wherein the second indicator member 9002 is driven the middle primary indicator member, and after a predetermined number of actuations (e.g., 80), the drive member 9004 on the middle primary indicator member engages a first driven member 9018 on the second indicator member and rotates the second indicator member 9002 an incremental amount. In this embodiment, the drive member 9004 is positioned adjacent one of a numerical indicia (e.g., "8") on the first indicator member corresponding to the numerical indicia (e.g., "2") being displayed in the viewing window. After another predetermined number of actuations (e.g., 180), the drive member 9004 on the middle primary indicator member 6560 engages a second driven member 9018 on the second indicator member and thereby moves the second indicator member another incremental amount. The indicia on the second indicator member is configured such that the indicia visible to the user in the viewing window 9014 transitions from an initial display (e.g., green) to warning display (e.g., red) on the second rotational movement of the second indicator member, with the indicia remaining in the initial display (e.g., green) through the first rotational movement of the second indicator member. Accordingly, in this embodiment, the user is advised or warned by the change in indicia that less than a minimum predetermined number (e.g., 20) of dosages of substance remain in the container. The user can quickly reference the first indicator members to determine the exact numerical quantity of dosages (e.g., nineteen (19)) remaining in the container. Of course, it should be understood that if the container has only one hundred (100) dosages of substance, the indicia can be configured to change from an initial indicia display (e.g., green) to warning indicia display (e.g., red) in the viewing window 9014 upon the first advancement of the second indicator member 9002, e.g., when less than 20 dosages remain in the container. Conversely, if more than 200 dosages are contained in the container, the dosage indicia can be arranged on the indicator member such that the displayed indicia changes from the initial display to the warning display only in response to the advancement of additional driven members. For example, the indicia visible in the viewing window may remain green for two advancements of the second indicator member, and then turn red upon the third advancement. Of course, it should be understood that indicia other than the color can be used to warn the user, for example textual messages that the container is "low," "empty," etc. Likewise, the initial display can be nothing, e.g., blank, or textual, e.g., "full," "reserves," etc.

It should also be understood that the drive member 9004 and driven members 9018 can be configured such that the second indicator member 9002 is advanced after any number of predetermined number of actuations corresponding to a minimum number of dosages of substance remaining in the container, whether it be 180 actuations, 80 actuations, or any other number of actuations. Thus for example, if the container is provided with 240 dosages of substance, and it is desired to warn the user when less than 30 dosages remain, the second indicator member 9002 is positioned such that the driven member 9018 is engaged by the drive member 9004 on the middle primary indicator member 6560 each time the numerical indicia "3" on the middle primary indicator member appears in the viewing window 9014, and further such that it warns the user with the secondary indicia when 210 actuations have been made. In this example, the primary indicator members 6560 preferably initially display the number of dosages remaining in the container, rather than the number dispensed. One of skill in the art should understand that second indicator member 9002 can be positioned for the opposite sequence (i.e., a counting of the number of dosages dispensed from the container). The second indicator member 9002 is rotationally positioned relative to the primary indicator member 6560 in this example such that the three driven members 9018 are engaged, with three incremental rotations of the second indicator member, before the indicia visible in the window 9018 turns from green to red. Of course, the indicia can also be provided with a transition between multiple displays (e.g., green to yellow to red) to give the user further advance warning about the depletion of dosages of substance in the container.

Referring to the embodiment of FIGS. 147-153, the second indicator member is provided with two regions 9103, 9105 (e.g., initial and warning indicia) that are stepped around the circumference of the indicator member 9002. In this embodiment, the second indicator member is advanced or moved upon every tenth actuation of the container, since the driven members 9018 are aligned with the drive member 9004 formed on the first outer primary indicator member (ones counter), such that the predetermined number of movements of the first primary indicator member required to move the second indicator member is ten. Referring to FIGS. 148-150, the regions 9103, 9105 can be configured and stepped such that the second region 9105 is partially brought into view through the viewing window 9014 upon a predetermined number of actuations (e.g., 100). Additional portions of the second region 9105 are made visible in the window (see, e.g., FIG. 151), until the entirety of the second indicator member visible in the window consists of the second region 9105 of warning indicia (see, e.g., FIG. 152) upon a predetermined number of actuations (e.g., 190) such that the user is provided with a warning that less than a predetermined number of dosages of substance (e.g., 21) remain in the container. In this way, the secondary indicator member provides a progressive secondary warning to the user about the number of doses remaining in the container, with a final warning that less than a predetermined number remain therein.

Referring to the operation of the embodiment of FIGS. 118-128, as the third primary indicator member 6550 completes one rotation, the drive member 9110 formed thereon engages a first edge 9112 of the second indicator member 9102 and translates the second indicator member in a first direction 9116 parallel to the axis of rotation 9124 of the primary indicator members. During this movement, the indicia visible to the user remains in the initial display (e.g., green) as the second indicator member is moved in the first direction. As the second indicator member 9102 is moved in the first direction 9116, a second edge 9120 of the second indicator member, or driven portion, is moved into alignment with the drive member 9114 formed on the second primary indicator member.

Upon completion of a predetermined number of actuations, and a corresponding rotation of the second primary indicator member, the drive member 9114 on the second or middle primary indicator member is brought into engagement with the second edge and translates the second indicator member 9102 in a second direction 9118, preferably substantially perpendicular to the first direction. As the second indicator member 9102 is translated in the second direction 9118, the indicia visible to the user in the viewing window 9108 transitions from the initial display (e.g., green) to the warning display (e.g., red) thereby warning the user that less than a minimum predetermined number of dosages remain in the container. In this embodiment, the second indicator member 9102 is provided with two colored regions 9103, 9105, for example green and red, with the green region visible through the viewing window when the second indicator member is in the initial position and when it is moved in the first direction. The red region 9105 becomes visible in the window as the second indicator member is moved in the second direction.

For example, if the container initially contains 200 or less dosages of substance, the drive member 9110 on the third primary indicator member engages and translates the second indicator member in the first direction after 100 dosages have been dispensed (i.e., after the third primary indicator member completes one revolution), thereby positioning the second edge of the second indicator 1114 on the member for subsequent engagement by the drive member on the second, middle primary indicator member. The drive member on the second, middle primary indicator member is positioned such that it engages the second end after a predetermined number of actuations, with a predetermined number of remaining or dispensed dosages appearing in the viewing window. For example, if it is desired to warn the user when less than 20 dosages remain, the drive member 9114 is positioned on the second primary indicator member such that it engages the second edge 9120 as the second, middle primary indicator member is moved from 2 to 1 and as the first primary indicator member is moved from 0 to 9 (i.e., as the visible numerical indicia move from 20 to 19). One of skill in the art will understand that the drive member 9114 can be positioned such that the indicia transitions when the count moves from 90 to 89, from 80 to 79, from 70 to 69, from 60 to 59, from 50 to 49, from 40 to 39 from 30 to 29 or from 10 to 9.

In any of the embodiments, and referring for example to FIG. 123, after the primary indicator members reach a count of "000," thereby indicating that the container is empty, a stop arm 9111 on the third primary indicator member, which stop arm extends radially outward from the other teeth, engages a non-return member 6900 so as to prevent further rotation of the primary indicator members. A subsequent force applied to the cap member will bend or deform the pawl 48.

In an alternative embodiment, the second indicator member 9102 is provided with indicia that transition to warn the user as the third primary indicator member moves the second indicator member 9102 in either a first or second direction 9116, 9118, e.g., when less than 200, 100, etc., dosages remain in the container.

In operation of the embodiments shown in FIGS. 5, 6, 7, 9, 20, 29, 36, 38, 44, 45, 71, 72, 74, 77 and 80, as the indicator member 60, 260, 460, 760, 1060, 2060, 7050, 7062 is advanced a predetermined number of times to indicate the dispensing of a predetermined number of dosages, e.g., 180, such that a predetermined minimum number of dosages of substance remain in the container, e.g., 20, the drive member 9210 on the primary indicator member engages the driven member 9212 on the second indicator member 9202 and rotates or pivots the second indicator member an incremental amount, with the indicia on an outer surface of the second indicator member transitioning in the viewing window 9208 to indicate to the user that less than the minimum predetermined number of dosages of substance remain in the container. Alternatively, as explained above, the second indicator member is translated by the primary indicator member.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An indicating device for indicating the number of dosages of a substance that have been dispensed from or remain in a container, said indicating device comprising:
   a first housing member comprising a first peripheral wall extending in a longitudinal direction and laterally spaced apart first, second, and third guide members spaced radially inwardly from said first peripheral wall;
   a second housing member comprising a second peripheral wall extending in said longitudinal direction, wherein said first and second housing members are reciprocally moveable relative to each other along a longitudinal axis, said second housing member comprising laterally spaced apart first, second, and third guides spaced radially inwardly from said second peripheral wall, wherein said first, second and third guides are shaped to receive said first, second, and third guide members respectively, and wherein said first and second guides are not shaped to receive said second and first guide members respectively, wherein one of said first and second housing members has a generally open bottom and the other of said first and second housing members has a generally open top, wherein said first and second housing members define a cavity between said first and second housing members;
   a biasing member biasing said second member relative to said first member along said longitudinal axis; and
   an indicating member disposed in said cavity between said first and second housing members, wherein said indicating member is moveable in response to said reciprocal movements of said first and second housing members along said longitudinal axis, and wherein said first, second and third guide members are reciprocally moveable within said first, second and third guides in response to said reciprocal movements of said first and second housing members along said longitudinal axis.

2. The indicating device of claim 1 wherein said first and second guide members have differently configured cross-sections.

3. The indicating device of claim 2 wherein said cross-sections of said first and second guide members comprise circular shapes having different first and second diameters respectively.

4. The indicating device of claim 1 wherein at least one of the first and second guide members has a T-shaped cross-section.

5. The indicating device of claim 1 wherein said first and second guides have differently configured cross-sections.

6. The indicating device of claim 1 wherein said first, second and third guide members have differently configured cross-sections.

7. The indicating device of claim 1 wherein one of said first and second housing members comprises a pawl positioned to engage a drive gear supported by the other of the first and second housing members when said first and second guide members are disposed in said first and second guides.

8. The indicating device of claim 1 wherein one of said first and second housing member comprises an engagement member engaging the other of said first and second housing members.

9. An indicating device for indicating the number of dosages of a substance that have been dispensed from or remain in a container, said indicating device comprising:
- a first housing member having laterally spaced apart first and second guide members, wherein said first housing member comprises a first peripheral wall extending in a longitudinal direction, and wherein said first and second guide members are positioned interiorly of said first peripheral wall;
- a second housing member comprising a second peripheral wall extending in said longitudinal direction, wherein said first and second housing members are reciprocally moveable relative to each other along a longitudinal axis, said second housing member comprising laterally spaced apart first and second guides positioned interiorly of said second peripheral wall, wherein said first and second guides are shaped to receive said first and second guide members respectively, and wherein said first and second guides are not shaped to receive said second and first guide members respectively, wherein one of said first and second housing members has a generally open bottom and the other of said first and second housing members has a generally open top, wherein said first and second housing members define a cavity between said first and second housing members;
- a biasing member biasing said second member relative to said first member along said longitudinal axis; and
- an indicating member disposed in said cavity between said first and second housing members, wherein said indicating member is moveable in response to said reciprocal movements of said first and second housing members along said longitudinal axis, and wherein said first and second guide members are reciprocally moveable within said first and second guides in response to said reciprocal movements of said first and second housing members along said longitudinal axis.

10. The indicating device of claim 1 wherein indicating member is positioned between said first and second guide members.

11. An indicating device for indicating the number of dosages of a substance that have been dispensed from or remain in a container, said indicating device comprising:
- a first housing member having laterally spaced apart first and second guide members, wherein said first housing member comprises a first peripheral wall extending in a longitudinal direction, and wherein said first and second guide members are positioned interiorly of said first peripheral wall, and wherein said first and second guide members have differently configured cross-sections;
- a second housing member comprising a second peripheral wall extending in said longitudinal direction, wherein said first and second housing members are reciprocally moveable relative to each other along a longitudinal axis, said second housing member comprising laterally spaced apart first and second guides positioned interiorly of said second peripheral wall, wherein said first and second guides are received in said first and second guide members respectively;
- a biasing member biasing said second member relative to said first member along said longitudinal axis; and
- at least one indicating member disposed between said first and second housing members and positioned between said first and second guide members, wherein said indicating member is moveable in response to said reciprocal movements of said first and second housing members along said longitudinal axis, and wherein said first and second guide members are reciprocally moveable within said first and second guides in response to said reciprocal movements of said first and second housing members along said longitudinal axis.

12. The indicating device of claim 11 wherein at least one of the first and second guide members has a T-shaped cross-section.

13. The indicating device of claim 11 wherein said first and second guides have differently configured cross-sections.

14. The indicating device of claim 11 wherein said first housing member comprises a third guide member laterally spaced from said first and second guide members, and said second housing member comprises a third guide laterally spaced from said first and second guides, wherein said third guide member is received in said third guide.

15. The indicating device of claim 14 wherein said at least one indicating member is positioned between said first and third guide members.

16. The indicating device of claim 14 wherein said first, second and third guide members have differently configured cross-sections.

17. The indicating device of claim 11 wherein one of said first and second housing members comprises a pawl positioned to engage a drive gear supported by the other of the first and second housing members when said first and second guide members are received in said first and second guides.

18. The indicating device of claim 11 wherein one of said first and second housing member comprises an engagement member engaging the other of said first and second housing members.

19. The indicating device of claim 11 wherein said first housing member comprises a peripheral wall extending in said longitudinal direction, and wherein said first and second guide members are positioned adjacent said peripheral wall.

20. An aerosol delivery device comprising:
- a dispenser housing;
- a container comprising a medicament, said container coupled to said dispenser housing, wherein said container is moveable in a longitudinal direction relative to said dispenser housing to dispense a dosage of medicament; and
- an indicating device engaged with said container, said indicating device comprising:
  - a first housing member comprising a first peripheral wall extending in a longitudinal direction and laterally spaced apart first, second, and third guide members spaced radially inwardly from said first peripheral wall;
  - a second housing member comprising a second peripheral wall extending in said longitudinal direction, wherein said first and second housing members are reciprocally moveable relative to each other along a longitudinal axis, said second housing member comprising laterally spaced apart first, second, and third guides spaced radially inwardly from said second peripheral wall, wherein said first, second and third guides are shaped to receive said first, second, and third guide members respectively, and wherein said first and second guides are not shaped to receive said second and first guide members respectively, wherein one of said first and second housing members has a generally open bottom and the other of said first and second housing members has a generally open top, wherein said first and second housing members define a cavity between said first and second housing members;

a biasing member biasing said second member relative to said first member along said longitudinal axis; and an indicating member disposed in said cavity between said first and second housing members, wherein said indicating member is moveable in response to said reciprocal movements of said first and second housing members along said longitudinal axis, and wherein said first, second and third guide members are reciprocally moveable within said first, second and third guides in response to said reciprocal movements of said first and second housing members along said longitudinal axis.

21. The aerosol delivery device of claim 20 wherein said first and second guide members have differently configured cross-sections.

22. The aerosol delivery device of claim 20 wherein said first, second and third guide members have differently configured cross-sections.

23. The aerosol delivery device of claim 20 wherein one of said first and second housing members comprises a pawl positioned to engage a drive gear supported by the other of the first and second housing members when said first and second guide members are disposed in said first and second guides.

24. The aerosol delivery device of claim 20 wherein indicating member is positioned between said first and second guide members.

25. An aerosol delivery device comprising:
a dispenser housing;
a container comprising a medicament, said container coupled to said dispenser housing, wherein said container is moveable in a longitudinal direction relative to said dispenser housing to dispense a dosage of medicament; and
an indicating device engaged with said container, said indicating device comprising:
 a first housing member having laterally spaced apart first and second guide members, wherein said first and second guide members have differently configured cross-sections, and wherein said first housing member comprises a first peripheral wall extending in said longitudinal direction, and wherein said first and second guide members are positioned interiorly of said first peripheral wall;
 a second housing member comprising a second peripheral wall extending in a longitudinal direction, wherein said first and second housing members are reciprocally moveable relative to each other along a longitudinal axis, said second housing member comprising laterally spaced apart first and second guides positioned interiorly of said second peripheral wall, wherein said first and second guides are received in said first and second guide members respectively;
 a biasing member biasing said second member relative to said first member along said longitudinal axis; and
 at least one indicating member disposed between said first and second housing members and positioned between said first and second guide members, wherein said indicating member is moveable in response to said reciprocal movements of said first and second housing members along said longitudinal axis, and wherein said first and second guide members are reciprocally moveable within said first and second guides in response to said reciprocal movements of said first and second housing members along said longitudinal axis.

26. The aerosol delivery device of claim 25 wherein said first housing member comprises a third guide member laterally spaced from said first and second guide members, and said second housing member comprises a third guide laterally spaced from said first and second guides, wherein said third guide member is received in said third guide.

27. The aerosol delivery device of claim 26 wherein said at least one indicating member is positioned between said first and third guide members.

28. The aerosol delivery device of claim 26 wherein said first, second and third guide members have differently configured cross-sections.

\* \* \* \* \*